United States Patent
Rosinko et al.

(10) Patent No.: US 9,962,486 B2
(45) Date of Patent: May 8, 2018

(54) SYSTEM AND METHOD FOR DETECTING OCCLUSIONS IN AN INFUSION PUMP

(71) Applicant: Tandem Diabetes Care, Inc., San Diego, CA (US)

(72) Inventors: Michael J. Rosinko, Anaheim, CA (US); Geoffrey A. Kruse, San Diego, CA (US); Paul Harris, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 371 days.

(21) Appl. No.: 14/930,053

(22) Filed: Nov. 2, 2015

(65) Prior Publication Data

US 2016/0051758 A1    Feb. 25, 2016

Related U.S. Application Data

(63) Continuation of application No. 13/829,115, filed on Mar. 14, 2013, now Pat. No. 9,173,998.

(51) Int. Cl.
*A61M 5/168* (2006.01)
*A61M 5/142* (2006.01)

(52) U.S. Cl.
CPC .... *A61M 5/16831* (2013.01); *A61M 5/14216* (2013.01); *A61M 5/14244* (2013.01);
(Continued)

(58) Field of Classification Search
CPC .......... A61M 5/16831; A61M 5/14216; A61M 2005/14268; A61M 2005/16863
See application file for complete search history.

(56) References Cited

U.S. PATENT DOCUMENTS

| 318,856 A | 5/1885 | Bilz |
|---|---|---|
| 329,881 A | 11/1885 | Benton |

(Continued)

FOREIGN PATENT DOCUMENTS

| CN | 1229347 A | 9/1999 |
|---|---|---|
| CN | 2668155 Y | 1/2005 |

(Continued)

OTHER PUBLICATIONS

US 8,333,733, 12/2012, Lanigan et al. (withdrawn)
(Continued)

*Primary Examiner* — Nathan R Price
*Assistant Examiner* — Melissa A Snyder
(74) *Attorney, Agent, or Firm* — Patterson Thuente Pedersen, P.A.

(57) ABSTRACT

Occlusions in a delivery line of an infusion pump can be detected by measuring pressure differentials in the pump over short periods of time in order to minimize the effects of long term systematic sensor changes. In a delivery mode such as basal insulin delivery where a small portion of a volume of fluid is delivered, pressure readings can be obtained before and after the motor move to deliver each portion and compared. The differentials after one or more motor moves can be compared to determine whether an occlusion is present. In a delivery mode such as bolus insulin delivery in which an entire volume of fluid is delivered, pressure differentials can be obtained for consecutive deliveries at a common point in the delivery cycle of each delivery. Comparison of these pressure values can be used to determine whether an occlusion is present.

19 Claims, 14 Drawing Sheets

(52) U.S. Cl.
CPC ............. *A61M 2005/14268* (2013.01); *A61M 2005/16863* (2013.01); *A61M 2205/18* (2013.01); *A61M 2205/3331* (2013.01); *A61M 2205/3368* (2013.01); *A61M 2205/502* (2013.01)

(56) References Cited

U.S. PATENT DOCUMENTS

| | | |
|---|---|---|
| 332,402 A | 12/1885 | Leadley |
| 596,062 A | 12/1897 | Firey |
| 722,431 A | 3/1903 | Packard |
| 818,938 A | 4/1906 | Crane |
| 926,092 A | 6/1909 | Bright |
| 1,079,522 A | 11/1913 | Smith |
| 1,274,884 A | 8/1918 | Hudson |
| 1,304,036 A | 5/1919 | Eshelby |
| 1,314,987 A | 9/1919 | Smith |
| 1,643,021 A | 9/1927 | Luyties |
| 1,657,663 A | 6/1928 | Devereux |
| 1,718,596 A | 6/1929 | Smith |
| 1,866,061 A | 7/1932 | Schoel |
| 1,910,032 A | 5/1933 | Mills |
| 2,018,316 A | 10/1935 | Ownings |
| 2,029,630 A | 2/1936 | McMichael |
| 2,147,164 A | 2/1939 | Kent |
| 2,398,234 A | 4/1946 | Long |
| 2,412,397 A | 12/1946 | Harper |
| 2,444,677 A | 7/1948 | Rosenblum |
| 2,454,929 A | 11/1948 | Kempton |
| 2,462,596 A | 2/1949 | Bent |
| 2,495,693 A | 1/1950 | Byrd, Jr. et al. |
| 2,497,020 A | 2/1950 | Singer |
| 2,568,519 A | 9/1951 | Smith |
| 2,599,325 A | 6/1952 | Fritzberg |
| 2,629,376 A | 2/1953 | Pierre et al. |
| 2,629,402 A | 2/1953 | Cook |
| 2,667,900 A | 2/1954 | Cantalupo |
| 2,674,262 A | 4/1954 | Bradshaw |
| 2,679,954 A | 6/1954 | Barnes |
| 2,691,542 A | 10/1954 | Chenoweth |
| 2,701,583 A | 2/1955 | Rux |
| 2,706,612 A | 4/1955 | Ratelband |
| 2,728,355 A | 12/1955 | Dahl |
| 2,735,642 A | 2/1956 | Norman |
| 2,736,463 A | 2/1956 | Michael |
| 2,746,709 A | 5/1956 | Minor |
| 2,764,183 A | 9/1956 | Gollehon |
| 2,781,058 A | 2/1957 | Warhus |
| 2,834,379 A | 5/1958 | Fields |
| 2,841,237 A | 7/1958 | Slayter |
| 2,852,033 A | 9/1958 | Orser |
| 2,878,836 A | 3/1959 | Binks |
| 2,891,578 A | 6/1959 | Dahl et al. |
| 2,898,078 A | 8/1959 | Stephenson et al. |
| 2,898,088 A | 8/1959 | Alder |
| 2,899,979 A | 8/1959 | Dahl et al. |
| 2,936,788 A | 5/1960 | Dahl et al. |
| 2,939,487 A | 6/1960 | Fraser et al. |
| 2,960,109 A | 11/1960 | Wilson |
| 2,968,318 A | 1/1961 | Bauman |
| 2,971,466 A | 2/1961 | Corbett |
| 2,989,086 A | 6/1961 | Dahl |
| 3,017,903 A | 1/1962 | Walter |
| 3,023,750 A | 2/1962 | Baron |
| 3,035,613 A | 5/1962 | Beatty |
| 3,059,639 A | 10/1962 | Blackman et al. |
| 3,060,966 A | 10/1962 | Ratelband |
| 3,061,039 A | 10/1962 | Peters |
| 3,070,132 A | 12/1962 | Sheridan |
| 3,072,151 A | 1/1963 | Quercia |
| 3,095,120 A | 6/1963 | Steiner et al. |
| 3,095,175 A | 6/1963 | Iketani |
| 3,121,445 A | 2/1964 | Wisniewski |
| 3,123,900 A | 3/1964 | Millar |
| 3,133,678 A | 5/1964 | Marwell et al. |
| 3,143,861 A | 8/1964 | Dumas |
| 3,153,414 A | 10/1964 | Beall et al. |
| 3,174,694 A | 3/1965 | Kitabayshi |
| 3,187,562 A | 6/1965 | Rolfson |
| 3,189,125 A | 6/1965 | Windsor et al. |
| 3,195,586 A | 7/1965 | Vogt |
| 3,202,178 A | 8/1965 | Wolfe |
| 3,203,662 A | 8/1965 | Lau |
| 3,214,903 A | 11/1965 | Cochran |
| 3,216,451 A | 11/1965 | Smallpeice |
| 3,227,311 A | 1/1966 | Rowell |
| 3,298,394 A | 1/1967 | Chorkey |
| 3,302,578 A | 2/1967 | Anderson |
| 3,318,138 A | 5/1967 | Rolfson |
| 3,338,049 A | 8/1967 | Fernberger |
| 3,347,418 A | 10/1967 | Fefferman |
| 3,376,625 A | 4/1968 | McCulloch |
| 3,409,050 A | 11/1968 | Weese |
| 3,428,223 A | 2/1969 | Lewiecki et al. |
| 3,430,659 A | 3/1969 | Henderson |
| 3,455,147 A | 7/1969 | Peck et al. |
| 3,479,002 A | 11/1969 | Hirs |
| 3,493,496 A | 2/1970 | Bray et al. |
| 3,508,587 A | 4/1970 | Mauch |
| 3,532,125 A | 10/1970 | Everett et al. |
| 3,556,159 A | 1/1971 | Bleasdale |
| 3,568,847 A | 3/1971 | Carr |
| 3,583,603 A | 6/1971 | Freckmann et al. |
| 3,586,040 A | 6/1971 | Urback |
| 3,596,939 A | 6/1971 | Gibson |
| 3,620,500 A | 11/1971 | Santomieri |
| 3,621,882 A | 11/1971 | Kuplec |
| 3,654,959 A | 4/1972 | Kassel |
| 3,665,967 A | 5/1972 | Kachnik |
| 3,673,853 A | 7/1972 | Griswold et al. |
| 3,674,183 A | 7/1972 | Venable et al. |
| 3,675,672 A | 7/1972 | Freeman |
| 3,648,694 A | 8/1972 | Mogos et al. |
| 3,693,484 A | 9/1972 | Sanderson, Jr. |
| 3,696,958 A | 10/1972 | Lee |
| 3,699,812 A | 10/1972 | Masnik |
| 3,717,174 A | 2/1973 | Dewall |
| 3,724,234 A | 4/1973 | Garavelli |
| 3,756,459 A | 9/1973 | Bannister et al. |
| 3,833,019 A | 9/1974 | Diggs |
| 3,836,113 A | 9/1974 | Johnson |
| 3,837,363 A | 9/1974 | Meronek |
| 3,838,794 A | 10/1974 | Cogley et al. |
| 3,847,178 A | 11/1974 | Keppel |
| 3,860,353 A | 1/1975 | Lukasik et al. |
| 3,894,538 A | 7/1975 | Richter |
| 3,899,135 A | 8/1975 | O'Brian |
| 3,918,674 A | 11/1975 | Sutter |
| 3,946,761 A | 3/1976 | Thompson et al. |
| RE28,890 E | 7/1976 | Ingram et al. |
| 3,970,105 A | 7/1976 | Pelton et al. |
| 3,985,133 A | 10/1976 | Jenkins et al. |
| 3,991,972 A | 11/1976 | Eaton |
| 4,000,857 A | 1/1977 | Moen |
| 4,003,398 A | 1/1977 | Duveau |
| 4,023,772 A | 5/1977 | Ratelband |
| 4,028,931 A | 6/1977 | Bisera et al. |
| 4,032,265 A | 6/1977 | Miller |
| 4,042,153 A | 8/1977 | Callahan et al. |
| 4,076,872 A | 2/1978 | Lewiecki et al. |
| 4,087,301 A | 5/1978 | Steadman |
| 4,089,206 A | 5/1978 | Raffel et al. |
| 4,103,689 A | 8/1978 | Leighton |
| 4,105,050 A | 8/1978 | Hendrickson et al. |
| 4,106,510 A | 8/1978 | Hakim et al. |
| 4,111,391 A | 9/1978 | Pilolla |
| 4,137,913 A | 2/1979 | Georgi |
| 4,156,127 A | 5/1979 | Sako et al. |
| 4,178,938 A | 12/1979 | Au |
| 4,191,184 A | 3/1980 | Carlisle |
| 4,191,204 A | 3/1980 | Nehring |
| 4,191,358 A | 3/1980 | Ferri |
| 4,193,552 A | 3/1980 | Ishikawa |
| 4,195,810 A | 4/1980 | Lavin |

(56) References Cited

U.S. PATENT DOCUMENTS

| | | |
|---|---|---|
| 4,215,726 A | 8/1980 | Tagami |
| 4,228,956 A | 10/1980 | Varner |
| 4,248,270 A | 2/1981 | Ostrowski |
| 4,250,872 A | 2/1981 | Tamari |
| 4,254,791 A | 3/1981 | Bron |
| 4,265,241 A | 5/1981 | Portner et al. |
| 4,275,727 A | 6/1981 | Keeri-Szanto |
| 4,271,989 A | 7/1981 | O'Neill |
| 4,306,556 A | 12/1981 | Zelman |
| 4,314,621 A | 2/1982 | Hansen |
| 4,314,979 A | 2/1982 | Deabriges |
| 4,327,845 A | 5/1982 | Keyes et al. |
| 4,330,071 A | 5/1982 | Ohlson |
| 4,344,459 A | 8/1982 | Nelson |
| 4,356,935 A | 11/1982 | Kamin |
| 4,367,786 A | 1/1983 | Hafner et al. |
| 4,382,453 A | 5/1983 | Bujan et al. |
| 4,405,294 A | 9/1983 | Albarda |
| 4,406,656 A | 9/1983 | Hattler et al. |
| 4,411,651 A | 10/1983 | Schulman |
| 4,411,652 A | 10/1983 | Kramer |
| 4,416,596 A | 11/1983 | Lichtenstein |
| 4,432,468 A | 2/1984 | Siff et al. |
| 4,440,154 A | 4/1984 | Bellows |
| 4,440,323 A | 4/1984 | Benson |
| 4,443,218 A | 4/1984 | DeCant, Jr. et al. |
| 4,444,546 A | 4/1984 | Pazemenas |
| 4,448,538 A | 5/1984 | Mantel |
| 4,457,343 A | 7/1984 | Zukausky |
| 4,469,481 A | 9/1984 | Kobayshi |
| 4,481,808 A | 11/1984 | Sakata et al. |
| 4,491,155 A | 1/1985 | Meyer et al. |
| 4,492,339 A | 1/1985 | Kreitzberg |
| 4,498,843 A | 2/1985 | Schneider et al. |
| 4,508,144 A | 4/1985 | Bernett |
| 4,515,536 A | 5/1985 | van Os |
| 4,520,948 A | 6/1985 | Hampel et al. |
| 4,529,401 A | 6/1985 | Leslie et al. |
| 4,527,595 A | 7/1985 | Jorgensen et al. |
| 4,529,106 A | 7/1985 | Broadfoot et al. |
| 4,557,726 A | 12/1985 | Reinicke |
| 4,559,036 A | 12/1985 | Wunsch |
| 4,559,038 A | 12/1985 | Berg et al. |
| 4,562,751 A | 1/1986 | Nason et al. |
| 4,562,960 A | 1/1986 | Marty et al. |
| 4,565,542 A | 1/1986 | Berg |
| 4,570,745 A | 2/1986 | Sparks et al. |
| 4,573,994 A | 3/1986 | Fischell et al. |
| 4,592,390 A | 6/1986 | Boyd |
| 4,609,014 A | 9/1986 | Jurevic et al. |
| 4,620,648 A | 11/1986 | Schwartzman |
| 4,624,661 A | 11/1986 | Arimond |
| 4,627,573 A | 12/1986 | Havens et al. |
| 4,628,928 A | 12/1986 | Lowell |
| 4,636,226 A | 1/1987 | Canfora |
| 4,646,945 A | 3/1987 | Steiner et al. |
| 4,649,959 A | 3/1987 | Wadleigh |
| 4,650,469 A | 3/1987 | Berg et al. |
| 4,650,471 A | 3/1987 | Tamari |
| 4,651,781 A | 3/1987 | Kandelman |
| 4,657,486 A | 4/1987 | Stempfle et al. |
| 4,666,430 A | 5/1987 | Brown et al. |
| 4,667,700 A | 5/1987 | Buzzi |
| 4,673,415 A | 6/1987 | Stanford |
| 4,678,408 A | 7/1987 | Nason et al. |
| 4,678,460 A | 7/1987 | Rosner |
| 4,684,364 A | 8/1987 | Sawyer et al. |
| 4,684,367 A | 8/1987 | Schaffer et al. |
| 4,685,903 A | 8/1987 | Cable et al. |
| 4,687,423 A | 8/1987 | Maget |
| 4,699,615 A | 10/1987 | Fischell et al. |
| 4,713,063 A | 12/1987 | Krumme |
| 4,718,893 A | 1/1988 | Dorman et al. |
| 4,723,947 A | 2/1988 | Konopka |
| 4,724,870 A | 2/1988 | Molb et al. |
| 4,741,736 A | 5/1988 | Brown |
| 4,770,211 A | 9/1988 | Olsson |
| 4,773,448 A | 9/1988 | Francis |
| 4,778,451 A | 10/1988 | Kamen |
| 4,779,762 A | 10/1988 | Klein et al. |
| 4,776,842 A | 11/1988 | Franetzki et al. |
| 4,787,408 A | 11/1988 | Twerdochlib |
| 4,793,486 A | 12/1988 | Konopka et al. |
| 4,808,167 A | 2/1989 | Mann et al. |
| 4,810,243 A | 3/1989 | Howson |
| 4,823,844 A | 4/1989 | Bartholomew |
| 4,826,482 A | 5/1989 | Kamen |
| 4,840,191 A | 6/1989 | Gausman et al. |
| 4,850,972 A | 7/1989 | Schulman et al. |
| 4,850,980 A | 7/1989 | Lentz |
| 4,869,431 A | 9/1989 | Jubert et al. |
| 4,871,093 A | 10/1989 | Burshtain et al. |
| 4,883,093 A | 11/1989 | Miles et al. |
| 4,886,499 A | 12/1989 | Cirelli et al. |
| 4,886,514 A | 12/1989 | Maget |
| 4,893,966 A | 1/1990 | Roehl |
| 4,897,906 A | 2/1990 | Bartholomew |
| 4,902,278 A | 2/1990 | Maget |
| 4,919,596 A | 4/1990 | Slate et al. |
| 4,931,050 A | 6/1990 | Idriss |
| 4,936,832 A | 6/1990 | Vaillancourt |
| 4,938,259 A | 7/1990 | Schmidt |
| 4,955,860 A | 9/1990 | Ruano |
| 4,962,092 A | 10/1990 | Wood, Jr. |
| 4,969,884 A | 11/1990 | Yum |
| 4,973,402 A | 11/1990 | Johnson et al. |
| 4,976,162 A | 12/1990 | Kamen |
| 4,985,015 A | 1/1991 | Oberman et al. |
| 4,986,312 A | 1/1991 | Gute |
| 4,989,456 A | 2/1991 | Stupecky |
| 4,995,258 A | 2/1991 | Frank |
| 5,000,739 A | 3/1991 | Kulisz et al. |
| 5,002,527 A | 3/1991 | Reller et al. |
| 5,005,403 A | 4/1991 | Steudle et al. |
| 5,006,997 A | 4/1991 | Reich |
| 5,011,477 A | 4/1991 | Winchell et al. |
| 5,041,086 A | 4/1991 | Koenig et al. |
| 5,020,562 A | 6/1991 | Richmond et al. |
| 5,027,861 A | 7/1991 | Gute |
| 5,035,865 A | 7/1991 | Inaba et al. |
| 5,038,821 A | 8/1991 | Maget |
| 5,044,900 A | 9/1991 | Cavallaro |
| 5,047,044 A | 9/1991 | Smith et al. |
| 5,049,141 A | 9/1991 | Olive |
| 5,050,612 A | 9/1991 | Matsumura |
| 5,053,001 A | 10/1991 | Reller et al. |
| 5,053,189 A | 10/1991 | Chrise et al. |
| 5,059,171 A | 10/1991 | Bridge et al. |
| 5,059,182 A | 10/1991 | Laing |
| 5,062,834 A | 11/1991 | Gross et al. |
| 5,062,841 A | 11/1991 | Siegel |
| 5,076,911 A | 12/1991 | Brown et al. |
| 5,078,683 A | 1/1992 | Sancoff et al. |
| 5,080,653 A | 1/1992 | Voss et al. |
| 5,082,240 A | 1/1992 | Richmond |
| 5,082,503 A | 1/1992 | Sluga et al. |
| 5,083,908 A | 1/1992 | Gagnebin et al. |
| 5,084,021 A | 1/1992 | Baldwin |
| 5,085,644 A | 2/1992 | Watson et al. |
| 5,087,245 A | 2/1992 | Daon |
| 5,090,963 A | 2/1992 | Gross et al. |
| 5,091,091 A | 2/1992 | Terman |
| 5,091,094 A | 2/1992 | Veech |
| 5,108,363 A | 2/1992 | Tuttle et al. |
| 5,096,385 A | 3/1992 | Georgi et al. |
| 5,097,122 A | 3/1992 | Colman et al. |
| 5,103,211 A | 4/1992 | Daoud et al. |
| 5,104,526 A | 4/1992 | Brown et al. |
| 5,104,813 A | 4/1992 | Besemer et al. |
| 5,125,781 A | 6/1992 | Breunig et al. |
| 5,126,324 A | 6/1992 | Clark et al. |
| 5,127,258 A | 7/1992 | Brown et al. |
| 5,128,145 A | 7/1992 | Edgren et al. |
| 5,131,816 A | 7/1992 | Brown |

(56) References Cited

U.S. PATENT DOCUMENTS

| | | |
|---|---|---|
| 5,135,491 A | 8/1992 | Baldwin |
| 5,135,498 A | 8/1992 | Kam et al. |
| 5,135,499 A | 8/1992 | Tafani et al. |
| 5,148,154 A | 9/1992 | MacKay et al. |
| 5,149,413 A | 9/1992 | Maget |
| 5,154,712 A | 10/1992 | Herwick et al. |
| 5,156,591 A | 10/1992 | Gross et al. |
| 5,156,598 A | 10/1992 | Skakoon et al. |
| 5,157,960 A | 10/1992 | Brehm et al. |
| 5,158,230 A | 10/1992 | Curran |
| 5,167,633 A | 12/1992 | Mann et al. |
| 5,170,912 A | 12/1992 | Du |
| 5,170,986 A | 12/1992 | Zelczer et al. |
| 5,173,302 A | 12/1992 | Holmblad et al. |
| 5,176,502 A | 1/1993 | Sanderson et al. |
| 5,176,644 A | 1/1993 | Srisathapat et al. |
| 5,176,662 A | 1/1993 | Bartholomew et al. |
| 5,178,603 A | 1/1993 | Prince |
| 5,181,910 A | 1/1993 | Scanlon |
| 5,182,258 A | 1/1993 | Chiou |
| 5,184,359 A | 2/1993 | Tsukamura et al. |
| 5,186,431 A | 2/1993 | Tamari |
| 5,186,805 A | 2/1993 | Gross et al. |
| 5,190,522 A | 3/1993 | Wojcicki et al. |
| 5,191,719 A | 3/1993 | Kitt |
| 5,192,264 A | 3/1993 | Fossel |
| 5,192,272 A | 3/1993 | Faure |
| 5,197,322 A | 3/1993 | Indravudh |
| 5,203,506 A | 4/1993 | Gross et al. |
| 5,207,642 A | 5/1993 | Orkin et al. |
| 5,207,645 A | 5/1993 | Ross et al. |
| 5,207,666 A | 5/1993 | Idriss et al. |
| 5,209,265 A | 5/1993 | Taguri et al. |
| 5,215,450 A | 6/1993 | Tamari |
| 5,217,440 A | 6/1993 | Frassica |
| 5,217,442 A | 6/1993 | Davis |
| 5,218,987 A | 6/1993 | Heil |
| 5,220,515 A | 6/1993 | Freerks et al. |
| 5,228,291 A | 6/1993 | Meyering |
| 5,228,842 A | 6/1993 | Guebeli et al. |
| 5,226,446 A | 7/1993 | Cooper |
| 5,231,616 A | 7/1993 | Oliver et al. |
| 5,188,258 A | 8/1993 | Iwashita |
| 5,232,437 A | 8/1993 | Lysaght et al. |
| 5,232,449 A | 8/1993 | Stern et al. |
| 5,240,603 A | 8/1993 | Frank et al. |
| 5,241,935 A | 9/1993 | Beck et al. |
| 5,242,406 A | 9/1993 | Gross et al. |
| 5,242,408 A | 9/1993 | Jhuboo et al. |
| 5,243,983 A | 9/1993 | Tarr et al. |
| 5,246,147 A | 9/1993 | Gross |
| 5,247,434 A | 9/1993 | Peterson et al. |
| 5,254,096 A | 10/1993 | Rondelet et al. |
| 5,256,157 A | 10/1993 | Samiotes et al. |
| 5,257,971 A | 11/1993 | Lord et al. |
| 5,257,980 A | 11/1993 | Van Antwerp et al. |
| 5,259,399 A | 11/1993 | Brown |
| 5,259,732 A | 11/1993 | Stern |
| 5,261,459 A | 11/1993 | Atkinson et al. |
| 5,261,884 A | 11/1993 | Stern et al. |
| 5,266,265 A | 11/1993 | Raible |
| 5,270,005 A | 12/1993 | Raible |
| 5,271,724 A | 12/1993 | vanLintel |
| 5,272,294 A | 12/1993 | Charboneau et al. |
| 5,272,909 A | 12/1993 | Nguyen et al. |
| 5,273,406 A | 12/1993 | Feygin |
| 5,273,518 A | 12/1993 | Lee et al. |
| 5,278,142 A | 1/1994 | Chiou |
| 5,279,543 A | 1/1994 | Glickfeld et al. |
| 5,279,556 A | 1/1994 | Goi et al. |
| 5,279,585 A | 1/1994 | Balkwill |
| 5,279,586 A | 1/1994 | Balkwell |
| 5,290,684 A | 3/1994 | Kelly |
| 5,291,086 A | 3/1994 | Shekalim |
| 5,294,133 A | 3/1994 | Dutta |
| 5,295,796 A | 3/1994 | Goto et al. |
| 5,295,966 A | 3/1994 | Stern et al. |
| 5,295,967 A | 3/1994 | Rondelet et al. |
| 5,295,976 A | 3/1994 | Harris |
| 5,304,126 A | 4/1994 | Epstein et al. |
| 5,304,163 A | 4/1994 | Bonnici et al. |
| 5,308,340 A | 5/1994 | Harris |
| 5,312,233 A | 5/1994 | Tanny et al. |
| 5,320,250 A | 6/1994 | La et al. |
| 5,321,392 A | 6/1994 | Skakoon et al. |
| 5,322,418 A | 6/1994 | Comer |
| 5,322,620 A | 6/1994 | Brown et al. |
| 5,322,626 A | 6/1994 | Frank et al. |
| 5,327,777 A | 7/1994 | Kaye et al. |
| 5,328,460 A | 7/1994 | Lord et al. |
| 5,328,464 A | 7/1994 | Kriesel et al. |
| 5,303,843 A | 8/1994 | Zink et al. |
| 5,334,144 A | 8/1994 | Alchas et al. |
| 5,334,162 A | 8/1994 | Harris |
| 5,335,705 A | 8/1994 | Morishita et al. |
| 5,335,852 A | 8/1994 | Muntean et al. |
| 5,336,051 A | 8/1994 | Tamari |
| 5,336,174 A | 8/1994 | Daoud et al. |
| 5,336,180 A | 8/1994 | Kriesel et al. |
| 5,336,188 A | 8/1994 | Kriesel |
| 5,338,157 A | 8/1994 | Blomquist |
| 5,339,393 A | 8/1994 | Duffy et al. |
| 5,339,865 A | 8/1994 | Asghar et al. |
| 5,341,783 A | 8/1994 | Beck et al. |
| 5,342,180 A | 8/1994 | Daoud |
| 5,345,488 A | 9/1994 | Skipper et al. |
| 5,348,197 A | 9/1994 | Mizzi et al. |
| 5,348,548 A | 9/1994 | Meyer et al. |
| 5,349,933 A | 9/1994 | Hasegawa et al. |
| 5,350,224 A | 9/1994 | Nell et al. |
| 5,345,273 A | 10/1994 | Hagen |
| 5,352,201 A | 10/1994 | Jemmott |
| 5,354,273 A | 10/1994 | Hagen |
| 5,356,375 A | 10/1994 | Higley et al. |
| 5,356,378 A | 10/1994 | Doan |
| 5,356,632 A | 10/1994 | Gross et al. |
| 5,358,489 A | 10/1994 | Wyrick |
| 5,358,635 A | 10/1994 | Frank et al. |
| 5,360,062 A | 11/1994 | White |
| 5,360,734 A | 11/1994 | Chapman et al. |
| 5,362,213 A | 11/1994 | Komatsu et al. |
| 5,362,307 A | 11/1994 | Guy et al. |
| 5,364,242 A | 11/1994 | Olsen |
| 5,364,387 A | 11/1994 | Sweeny |
| 5,366,904 A | 11/1994 | Quereshi et al. |
| 5,367,910 A | 11/1994 | Woodward |
| 5,368,555 A | 11/1994 | Sussman et al. |
| 5,368,562 A | 11/1994 | Blomquist et al. |
| 5,369,976 A | 12/1994 | Ratton |
| 5,370,622 A | 12/1994 | Livingston et al. |
| 5,370,870 A | 12/1994 | Wong |
| 5,373,865 A | 12/1994 | Jung et al. |
| 5,376,070 A | 12/1994 | Purvis et al. |
| 5,381,823 A | 1/1995 | Dibartolo |
| 5,384,709 A | 1/1995 | Seder et al. |
| 5,387,192 A | 2/1995 | Glantz et al. |
| 5,387,327 A | 2/1995 | Khan |
| 5,388,453 A | 2/1995 | Ratton et al. |
| 5,389,071 A | 2/1995 | Kawahara et al. |
| 5,389,078 A | 2/1995 | Zalesky et al. |
| 5,389,091 A | 2/1995 | Moorehead |
| 5,390,671 A | 2/1995 | Lord et al. |
| 5,391,250 A | 2/1995 | Cheney, II et al. |
| 5,395,320 A | 3/1995 | Padda et al. |
| 5,395,324 A | 3/1995 | Hinrichs |
| 5,395,326 A | 3/1995 | Haber et al. |
| 5,399,166 A | 3/1995 | Laing |
| 5,403,551 A | 4/1995 | Galloway et al. |
| 5,407,444 A | 4/1995 | Kroll |
| 5,410,908 A | 5/1995 | Erichsen |
| 5,411,685 A | 5/1995 | Burgis |
| 5,415,024 A | 5/1995 | Proffitt et al. |
| 5,418,154 A | 5/1995 | Aebischer et al. |
| 5,419,770 A | 5/1995 | Crass et al. |

(56) References Cited

U.S. PATENT DOCUMENTS

| | | |
|---|---|---|
| 5,421,208 A | 6/1995 | Packard et al. |
| 5,423,743 A | 6/1995 | Buttrefield |
| 5,425,374 A | 6/1995 | Ueda et al. |
| 5,425,706 A | 6/1995 | Gross et al. |
| 5,425,742 A | 6/1995 | Joy |
| 5,427,870 A | 6/1995 | Joshi et al. |
| 5,431,208 A | 6/1995 | Packard et al. |
| 5,429,483 A | 7/1995 | Tamari |
| 5,429,601 A | 7/1995 | Conley et al. |
| 5,431,171 A | 7/1995 | Harrison et al. |
| 5,433,710 A | 7/1995 | VanAntwerp et al. |
| 5,435,465 A | 7/1995 | El-Amin |
| 5,435,697 A | 7/1995 | Guebeli et al. |
| 5,435,797 A | 7/1995 | Harris |
| 5,438,510 A | 8/1995 | Bryant et al. |
| 5,441,027 A | 8/1995 | Buchanon et al. |
| 5,442,948 A | 8/1995 | Cowing |
| 5,442,950 A | 8/1995 | Unalmiser et al. |
| 5,443,450 A | 8/1995 | Kratoska |
| 5,445,506 A | 8/1995 | Afflerbaugh et al. |
| 5,445,616 A | 8/1995 | Kratoska et al. |
| 5,447,509 A | 9/1995 | Mills et al. |
| 5,447,863 A | 9/1995 | Langley |
| 5,448,034 A | 9/1995 | Skipper et al. |
| 5,448,978 A | 9/1995 | Hasegawa et al. |
| 5,450,750 A | 9/1995 | Abler |
| 5,454,922 A | 10/1995 | Joshi et al. |
| 5,458,469 A | 10/1995 | Hauser |
| 5,460,030 A | 10/1995 | Blosxom et al. |
| 5,460,605 A | 10/1995 | Tuttle et al. |
| 5,460,618 A | 10/1995 | Harreld |
| 5,460,945 A | 10/1995 | Springer et al. |
| 5,462,417 A | 10/1995 | Chapman |
| 5,462,525 A | 10/1995 | Srisathapat et al. |
| 5,462,535 A | 10/1995 | Bonnichsen et al. |
| 5,464,392 A | 11/1995 | Epstein et al. |
| 5,464,398 A | 11/1995 | Haindl |
| 5,466,218 A | 11/1995 | Srisathapat et al. |
| 5,466,229 A | 11/1995 | Elson et al. |
| 5,469,846 A | 11/1995 | Khan |
| 5,470,318 A | 11/1995 | Griffith, III et al. |
| 5,472,577 A | 12/1995 | Porter et al. |
| 5,476,444 A | 12/1995 | Keeling et al. |
| 5,476,449 A | 12/1995 | Richmond |
| 5,476,460 A | 12/1995 | Montalvo |
| 5,478,316 A | 12/1995 | Bitdinger et al. |
| 5,478,751 A | 12/1995 | Oosta et al. |
| 5,480,294 A | 1/1996 | Di Perna et al. |
| 5,480,381 A | 1/1996 | Weston |
| 5,482,446 A | 1/1996 | Williamson et al. |
| 5,482,745 A | 1/1996 | Cuellar et al. |
| 5,483,930 A | 1/1996 | Moriya et al. |
| 5,485,408 A | 1/1996 | Blomquist |
| 5,487,528 A | 1/1996 | Richmond |
| 5,568,806 A | 1/1996 | Cheney, II et al. |
| 5,489,265 A | 2/1996 | Montalvo et al. |
| 5,492,534 A | 2/1996 | Athayde et al. |
| 5,494,578 A | 2/1996 | Brown et al. |
| 5,510,336 A | 2/1996 | Saven et al. |
| 5,497,772 A | 3/1996 | Schulman et al. |
| 5,498,421 A | 3/1996 | Grinstaff et al. |
| 5,503,538 A | 4/1996 | Wiernicki et al. |
| 5,505,709 A | 4/1996 | Funderburk et al. |
| 5,505,777 A | 4/1996 | Ciardella et al. |
| 5,509,294 A | 4/1996 | Gowing |
| 5,514,103 A | 5/1996 | Srisathapat et al. |
| 5,518,730 A | 5/1996 | Fuisz |
| 5,522,798 A | 6/1996 | Johnson et al. |
| 5,526,675 A | 6/1996 | Ratton |
| 5,527,288 A | 6/1996 | Gross et al. |
| 5,527,307 A | 6/1996 | Srisathapat et al. |
| 5,527,704 A | 6/1996 | Wolf, Jr. et al. |
| 5,531,697 A | 7/1996 | Olsen et al. |
| 5,533,876 A | 7/1996 | Nelson, II |
| 5,533,981 A | 7/1996 | Mandro et al. |
| 5,536,249 A | 7/1996 | Castellano et al. |
| 5,538,002 A | 7/1996 | Boussignac et al. |
| 5,538,043 A | 7/1996 | Salazar |
| 5,538,399 A | 7/1996 | Johnson |
| 5,540,562 A | 7/1996 | Giter |
| 5,544,519 A | 8/1996 | Hammarberg et al. |
| 5,545,140 A | 8/1996 | Conero et al. |
| 5,545,252 A | 8/1996 | Hinshaw et al. |
| 5,549,458 A | 8/1996 | Chapman et al. |
| 5,551,391 A | 9/1996 | Beck et al. |
| 5,551,850 A | 9/1996 | Williamson et al. |
| 5,554,177 A | 9/1996 | Kieval et al. |
| 5,556,421 A | 9/1996 | Prutchi et al. |
| 5,558,638 A | 9/1996 | Evers et al. |
| 5,562,079 A | 10/1996 | Gray, Jr. |
| 5,562,618 A | 10/1996 | Cai et al. |
| 5,563,347 A | 10/1996 | Martin et al. |
| 5,564,915 A | 10/1996 | Johnson |
| 5,566,865 A | 10/1996 | Jouillat et al. |
| 5,567,136 A | 10/1996 | Johnson |
| 5,567,287 A | 10/1996 | Joshi et al. |
| 5,568,038 A | 10/1996 | Tatsumi |
| 5,568,884 A | 10/1996 | Bruna |
| 5,569,186 A | 10/1996 | Lord et al. |
| 5,575,310 A | 11/1996 | Kamen et al. |
| 5,575,632 A | 11/1996 | Morris et al. |
| 5,575,770 A | 11/1996 | Melsky et al. |
| 5,578,005 A | 11/1996 | Sancoff et al. |
| 5,578,014 A | 11/1996 | Erez et al. |
| 5,578,832 A | 11/1996 | Trulson et al. |
| 5,582,168 A | 12/1996 | Samuels et al. |
| 5,584,667 A | 12/1996 | Davis |
| 5,584,815 A | 12/1996 | Pawelka et al. |
| 5,586,553 A | 12/1996 | Halili et al. |
| 5,586,727 A | 12/1996 | Shekalim |
| 5,590,648 A | 1/1997 | Mitchell et al. |
| 5,593,552 A | 1/1997 | Joshi et al. |
| 5,602,040 A | 2/1997 | May et al. |
| 5,603,729 A | 2/1997 | Brown et al. |
| 5,605,152 A | 2/1997 | Slate et al. |
| 5,605,701 A | 2/1997 | Bymaster et al. |
| 5,606,131 A | 2/1997 | Pope |
| 5,607,418 A | 3/1997 | Arzbaecher |
| 5,613,945 A | 3/1997 | Cai et al. |
| 5,615,671 A | 4/1997 | Schoonen et al. |
| 5,616,123 A | 4/1997 | Cheikh |
| 5,616,132 A | 4/1997 | Newman |
| 5,617,650 A | 4/1997 | Grim |
| 5,621,797 A | 4/1997 | Rosen |
| RE35,501 E | 5/1997 | Ross et al. |
| 5,626,566 A | 5/1997 | Petersen et al. |
| 5,628,324 A | 5/1997 | Sarbach |
| 5,628,349 A | 5/1997 | Diggins et al. |
| 5,628,624 A | 5/1997 | Nelson, II |
| 5,628,922 A | 5/1997 | Chen |
| 5,634,491 A | 6/1997 | Benedict |
| 5,634,779 A | 6/1997 | Eysymontt |
| 5,634,896 A | 6/1997 | Bryant et al. |
| 5,637,092 A | 6/1997 | Shaw |
| 5,637,095 A | 6/1997 | Nason et al. |
| 5,639,220 A | 6/1997 | Hawakawa |
| 5,639,441 A | 6/1997 | Sievers et al. |
| 5,639,473 A | 6/1997 | Grinstaff et al. |
| 5,641,405 A | 6/1997 | Keshaviah et al. |
| 5,643,773 A | 7/1997 | Aebisher et al. |
| 5,645,526 A | 7/1997 | Flower |
| 5,647,853 A | 7/1997 | Feldmann et al. |
| 5,647,854 A | 7/1997 | Olsen et al. |
| 5,651,980 A | 7/1997 | Lanza et al. |
| 5,656,032 A | 8/1997 | Kriesel et al. |
| 5,656,501 A | 8/1997 | Yedgar et al. |
| 5,656,503 A | 8/1997 | May et al. |
| 5,658,250 A | 8/1997 | Blomquist |
| 5,658,252 A | 8/1997 | Johnson |
| 5,659,126 A | 8/1997 | Farber |
| 5,660,150 A | 8/1997 | Anderson et al. |
| 5,660,163 A | 8/1997 | Schulman et al. |
| 5,665,065 A | 9/1997 | Colman et al. |
| 5,665,070 A | 9/1997 | McPhee |

(56) References Cited

U.S. PATENT DOCUMENTS

| | | |
|---|---|---|
| 5,669,877 A | 9/1997 | Blomquist |
| 5,671,874 A | 9/1997 | Behar et al. |
| 5,676,651 A | 10/1997 | Larson, Jr. et al. |
| 5,681,285 A | 10/1997 | Ford et al. |
| 5,681,435 A | 10/1997 | Joshi et al. |
| 5,685,844 A | 11/1997 | Marttila |
| 5,688,113 A | 11/1997 | Bareiss et al. |
| 5,688,225 A | 11/1997 | Walker |
| 5,688,232 A | 11/1997 | Flower |
| 5,693,018 A | 12/1997 | Kriesel et al. |
| 5,694,961 A | 12/1997 | Begemann et al. |
| 5,695,464 A | 12/1997 | Viallet |
| 5,695,472 A | 12/1997 | Wyrick |
| 5,695,473 A | 12/1997 | Olsen |
| 5,700,244 A | 12/1997 | Kriesel |
| 5,702,384 A | 12/1997 | Umeyama et al. |
| 5,704,366 A | 1/1998 | Tacklind et al. |
| 5,704,520 A | 1/1998 | Gross |
| 5,707,212 A | 1/1998 | Matthews |
| 5,707,361 A | 1/1998 | Slettenmark |
| 5,711,989 A | 1/1998 | Ciardella et al. |
| 5,712,795 A | 1/1998 | Layman et al. |
| 5,713,856 A | 2/1998 | Eggers et al. |
| 5,713,858 A | 2/1998 | Heruth et al. |
| 5,718,562 A | 2/1998 | Lawless et al. |
| 5,719,761 A | 2/1998 | Gatti et al. |
| 5,720,241 A | 2/1998 | Gail |
| 5,720,921 A | 2/1998 | Mersol |
| 5,722,367 A | 3/1998 | Izadorek |
| 5,728,396 A | 3/1998 | Peery et al. |
| 5,730,149 A | 3/1998 | Nayakama et al. |
| 5,735,818 A | 4/1998 | Kriesel et al. |
| 5,738,650 A | 4/1998 | Gregg |
| 5,740,718 A | 4/1998 | Rathweg |
| 5,741,211 A | 4/1998 | Renirie et al. |
| 5,741,242 A | 4/1998 | Kriesel et al. |
| 5,743,291 A | 4/1998 | Nehm et al. |
| 5,743,873 A | 4/1998 | Cai et al. |
| 5,746,733 A | 5/1998 | Capaccio et al. |
| 5,755,683 A | 5/1998 | Houle et al. |
| 5,755,696 A | 5/1998 | Caizza |
| 5,759,018 A | 6/1998 | Thanscheidt |
| 5,759,199 A | 6/1998 | Snell et al. |
| 5,763,267 A | 6/1998 | Kurjan et al. |
| 5,763,398 A | 6/1998 | Bengtsson |
| 5,765,464 A | 6/1998 | Morita |
| 5,765,729 A | 6/1998 | Miller et al. |
| 5,769,615 A | 6/1998 | Giter |
| 5,770,149 A | 6/1998 | Raible |
| 5,770,160 A | 6/1998 | Smith et al. |
| 5,771,770 A | 6/1998 | Muller |
| 5,772,409 A | 6/1998 | Johnson |
| 5,772,635 A | 6/1998 | Dastur et al. |
| 5,782,931 A | 6/1998 | Yang et al. |
| 5,785,681 A | 7/1998 | Indravudh |
| 5,785,688 A | 7/1998 | Joshi et al. |
| 5,788,642 A | 8/1998 | Hamatake et al. |
| 5,788,669 A | 8/1998 | Peterson |
| 5,788,671 A | 8/1998 | Johnson |
| 5,788,682 A | 8/1998 | Maget |
| 5,792,603 A | 8/1998 | Dunkelman et al. |
| 5,794,505 A | 8/1998 | Fischer et al. |
| 5,794,515 A | 8/1998 | Bethke |
| 5,795,327 A | 8/1998 | Wilson et al. |
| 5,797,867 A | 8/1998 | Guererra et al. |
| 5,798,114 A | 8/1998 | Elsberry et al. |
| 5,730,723 A | 9/1998 | Castellano et al. |
| 5,800,387 A | 9/1998 | Duffy et al. |
| 5,800,420 A | 9/1998 | Gross et al. |
| 5,803,319 A | 9/1998 | Smith et al. |
| 5,803,917 A | 9/1998 | Butterfield et al. |
| 5,807,315 A | 9/1998 | Van Antwerp et al. |
| 5,807,335 A | 9/1998 | Kriesel et al. |
| 5,807,336 A | 9/1998 | Russo et al. |
| 5,807,374 A | 9/1998 | Caizza et al. |
| 5,807,375 A | 9/1998 | Gross et al. |
| 5,810,737 A | 9/1998 | Dardik |
| 5,810,771 A | 9/1998 | Blomquist |
| 5,810,783 A | 9/1998 | Claro |
| 5,814,020 A | 9/1998 | Gross |
| 5,814,100 A | 9/1998 | Carpentier et al. |
| 5,820,587 A | 10/1998 | Place |
| 5,820,589 A | 10/1998 | Torgerson et al. |
| 5,820,622 A | 10/1998 | Gross et al. |
| 5,822,715 A | 10/1998 | Worthington et al. |
| 5,823,388 A | 10/1998 | Green |
| 5,823,746 A | 10/1998 | Johnson |
| 5,823,998 A | 10/1998 | Yamagata |
| 5,826,621 A | 10/1998 | Jemmott |
| 5,830,175 A | 11/1998 | Flower |
| 5,830,187 A | 11/1998 | Kriesel et al. |
| 5,837,220 A | 11/1998 | Blake et al. |
| 5,837,444 A | 11/1998 | Shah |
| 5,840,069 A | 11/1998 | Robinson |
| 5,840,071 A | 11/1998 | Kriesel et al. |
| 5,840,770 A | 11/1998 | Hill |
| 5,848,593 A | 12/1998 | McGrady et al. |
| 5,848,880 A | 12/1998 | Helmig |
| 5,848,990 A | 12/1998 | Cirelli et al. |
| 5,848,991 A | 12/1998 | Gross et al. |
| 5,849,031 A | 12/1998 | Martinez et al. |
| 5,849,737 A | 12/1998 | Chaplan et al. |
| 5,851,197 A | 12/1998 | Marano et al. |
| 5,851,198 A | 12/1998 | Castellano et al. |
| 5,851,549 A | 12/1998 | Svec |
| 5,851,985 A | 12/1998 | Tepic et al. |
| 5,853,386 A | 12/1998 | Davis et al. |
| 5,854,074 A | 12/1998 | Charlton et al. |
| 5,854,719 A | 12/1998 | Ginosar et al. |
| 5,858,001 A | 1/1999 | Tsals et al. |
| 5,858,201 A | 1/1999 | Atsuka et al. |
| 5,858,388 A | 1/1999 | Grossman et al. |
| 5,858,393 A | 1/1999 | Bymaster et al. |
| 5,859,365 A | 1/1999 | Kataoka et al. |
| 5,860,957 A | 1/1999 | Jacobson et al. |
| 5,863,187 A | 1/1999 | Bensley et al. |
| 5,865,603 A | 2/1999 | Francart, Jr. |
| 5,871,125 A | 2/1999 | Gross |
| 5,871,515 A | 2/1999 | Wiklund et al. |
| 5,873,857 A | 2/1999 | Kriesel |
| 5,876,370 A | 2/1999 | Blomquist |
| 5,876,189 A | 3/1999 | Lukas et al. |
| 5,876,368 A | 3/1999 | Flower |
| 5,877,146 A | 3/1999 | McKenzie et al. |
| 5,877,216 A | 3/1999 | Place et al. |
| 5,878,992 A | 3/1999 | Edwards et al. |
| 5,879,143 A | 3/1999 | Cote et al. |
| 5,879,144 A | 3/1999 | Johnson |
| 5,880,101 A | 3/1999 | Stankov |
| 5,882,494 A | 3/1999 | Van Antwerp et al. |
| 5,883,138 A | 3/1999 | Hershkowitz et al. |
| 5,885,211 A | 3/1999 | Eppstein et al. |
| 5,885,250 A | 3/1999 | Kriesel et al. |
| 5,885,614 A | 3/1999 | Hirsch |
| 5,886,056 A | 3/1999 | Hershkowitz et al. |
| 5,887,793 A | 3/1999 | Kieffer |
| 5,890,413 A | 4/1999 | Bayer et al. |
| 5,891,097 A | 4/1999 | Saito et al. |
| 5,893,708 A | 4/1999 | Nelson, II |
| 5,894,992 A | 4/1999 | Liu et al. |
| 5,895,369 A | 4/1999 | Flower |
| 5,897,530 A | 4/1999 | Jackson |
| 5,902,336 A | 5/1999 | Mishkin |
| 5,903,710 A | 5/1999 | Wefler et al. |
| 5,912,005 A | 6/1999 | Lanza et al. |
| 5,916,191 A | 6/1999 | Plunkett et al. |
| 5,919,156 A | 6/1999 | Stropkay et al. |
| 5,919,209 A | 6/1999 | Schouten |
| 5,919,216 A | 6/1999 | Houben et al. |
| 5,924,456 A | 6/1999 | Simon |
| 5,925,629 A | 6/1999 | Place |
| 5,928,194 A | 6/1999 | Maget |
| 5,928,281 A | 6/1999 | Huynh et al. |
| 5,924,448 A | 7/1999 | West |

(56) References Cited

U.S. PATENT DOCUMENTS

| | | |
|---|---|---|
| 5,928,196 A | 7/1999 | Johnson et al. |
| 5,928,201 A | 7/1999 | Poulsen et al. |
| 5,931,814 A | 8/1999 | Alex et al. |
| 5,933,287 A | 8/1999 | Muller |
| 5,935,099 A | 8/1999 | Peeterson et al. |
| 5,935,106 A | 8/1999 | Olsen |
| 5,935,168 A | 8/1999 | Yang et al. |
| 5,935,598 A | 8/1999 | Sage et al. |
| 5,938,636 A | 8/1999 | Kramer |
| 5,938,640 A | 8/1999 | Maget |
| 5,938,642 A | 8/1999 | Burroughs et al. |
| 5,941,846 A | 8/1999 | Duffy et al. |
| 5,950,879 A | 8/1999 | Ritsche |
| 5,948,367 A | 9/1999 | Gmeiner et al. |
| 5,951,521 A | 9/1999 | Mastrototaro et al. |
| 5,951,523 A | 9/1999 | Osterlund et al. |
| 5,954,485 A | 9/1999 | Johnson et al. |
| 5,954,643 A | 9/1999 | Van Antwerp et al. |
| 5,954,685 A | 9/1999 | Tierney |
| 5,954,696 A | 9/1999 | Ryan |
| 5,954,697 A | 9/1999 | Srisathapat et al. |
| 5,954,752 A | 9/1999 | Mongeon et al. |
| 5,957,861 A | 9/1999 | Combs et al. |
| 5,957,885 A | 9/1999 | Bollish et al. |
| 5,957,889 A | 9/1999 | Poulson et al. |
| 5,957,890 A | 9/1999 | Mann et al. |
| 5,957,895 A | 9/1999 | Sage et al. |
| 5,958,760 A | 9/1999 | Freeman |
| 5,960,403 A | 9/1999 | Brown |
| 5,961,305 A | 10/1999 | Eek et al. |
| 5,961,483 A | 10/1999 | Sage et al. |
| 5,962,566 A | 10/1999 | Grandfilis et al. |
| 5,962,794 A | 10/1999 | Kriesel et al. |
| 5,964,377 A | 10/1999 | Demarest et al. |
| 5,964,724 A | 10/1999 | Rivera et al. |
| 5,971,722 A | 10/1999 | Maget et al. |
| 5,973,012 A | 10/1999 | Behrmann et al. |
| 5,997,501 A | 10/1999 | Gross et al. |
| 5,976,109 A | 11/1999 | Heruth |
| 5,980,489 A | 11/1999 | Kriesel |
| 5,980,596 A | 11/1999 | Hershkowitz et al. |
| 5,983,976 A | 11/1999 | Kono |
| 5,984,894 A | 11/1999 | Poulson et al. |
| 5,984,897 A | 11/1999 | Peterson et al. |
| 5,984,906 A | 11/1999 | Bonnichsen et al. |
| 5,985,305 A | 11/1999 | Peery et al. |
| 5,985,894 A | 11/1999 | Poulsen et al. |
| 5,988,165 A | 11/1999 | Richey et al. |
| 5,988,851 A | 11/1999 | Gent |
| 5,988,998 A | 11/1999 | Glover |
| 5,989,216 A | 11/1999 | Johnson et al. |
| 5,989,222 A | 11/1999 | Cole et al. |
| 5,989,238 A | 11/1999 | Ginsburg |
| 5,989,409 A | 11/1999 | Kurnik et al. |
| 5,992,695 A | 11/1999 | Start |
| 5,993,421 A | 11/1999 | Kriesel |
| 5,993,425 A | 11/1999 | Kriesel |
| 5,995,860 A | 11/1999 | Sun et al. |
| 5,997,475 A | 12/1999 | Bortz |
| 5,997,518 A | 12/1999 | Laibovitz et al. |
| 6,001,089 A | 12/1999 | Burroughs et al. |
| 6,001,585 A | 12/1999 | Gramer |
| 6,003,566 A | 12/1999 | Thibault et al. |
| 6,003,736 A | 12/1999 | Ljunggren |
| 6,006,800 A | 12/1999 | Nakano |
| 6,007,314 A | 12/1999 | Nelson, II |
| 6,007,518 A | 12/1999 | Kriesel et al. |
| 6,012,034 A | 1/2000 | Hamparian et al. |
| 6,012,492 A | 1/2000 | Kozyuk |
| 6,013,020 A | 1/2000 | Meloul et al. |
| 6,016,044 A | 1/2000 | Holdaway |
| 6,017,318 A | 1/2000 | Gauthier |
| 6,017,545 A | 1/2000 | Modi |
| 6,019,747 A | 2/2000 | McPhee |
| 6,023,629 A | 2/2000 | Tamada |
| 6,023,641 A | 2/2000 | Thompson |
| 6,024,009 A | 2/2000 | Morita |
| 6,024,539 A | 2/2000 | Blomquist |
| 6,024,699 A | 2/2000 | Surwit |
| 6,030,358 A | 2/2000 | Odland |
| 6,030,363 A | 2/2000 | Kriesel |
| 6,033,377 A | 3/2000 | Rasmussen et al. |
| 6,034,054 A | 3/2000 | DeFelippis et al. |
| 6,035,639 A | 3/2000 | Kolmanovsky |
| 6,037,346 A | 3/2000 | Doherty, Jr. et al. |
| 6,038,960 A | 3/2000 | Fukushima et al. |
| 6,040,834 A | 3/2000 | Jain et al. |
| 6,042,561 A | 3/2000 | Ash et al. |
| 6,045,537 A | 4/2000 | Klitmose |
| 6,048,337 A | 4/2000 | Svedman |
| 6,051,256 A | 4/2000 | Platz et al. |
| 6,053,887 A | 4/2000 | Levitas |
| 6,056,522 A | 5/2000 | Johnson |
| 6,056,718 A | 5/2000 | Funderburk et al. |
| 6,059,507 A | 5/2000 | Adams |
| 6,059,753 A | 5/2000 | Faust et al. |
| 6,062,022 A | 5/2000 | Folsom et al. |
| 6,062,531 A | 5/2000 | Rapp et al. |
| 6,063,053 A | 5/2000 | Castellano et al. |
| 6,063,059 A | 5/2000 | Kriesel |
| 6,065,279 A | 5/2000 | Kuromitsu et al. |
| 6,065,289 A | 5/2000 | Phillips |
| 6,065,941 A | 5/2000 | Gray et al. |
| 6,070,761 A | 6/2000 | Bloom et al. |
| 6,071,423 A | 6/2000 | Brown et al. |
| 6,073,048 A | 6/2000 | Kieval et al. |
| 6,074,359 A | 6/2000 | Keshaviah et al. |
| 6,077,055 A | 6/2000 | Vilks |
| 6,077,246 A | 6/2000 | Kullas et al. |
| 6,080,130 A | 6/2000 | Castellano et al. |
| 6,083,602 A | 7/2000 | Caldwell et al. |
| 6,083,710 A | 7/2000 | Heller et al. |
| 6,086,561 A | 7/2000 | Kriesel et al. |
| 6,086,562 A | 7/2000 | Jacobson et al. |
| 6,093,167 A | 7/2000 | Houben et al. |
| 6,093,172 A | 7/2000 | Funderburk et al. |
| 6,093,312 A | 7/2000 | Boulter |
| 6,095,134 A | 8/2000 | Sievers et al. |
| 6,096,216 A | 8/2000 | Shanbrom et al. |
| 6,099,293 A | 8/2000 | Kern et al. |
| 6,099,495 A | 8/2000 | Kinghorn et al. |
| 6,099,504 A | 8/2000 | Gross et al. |
| 6,102,127 A | 8/2000 | Pierce |
| 6,103,033 A | 8/2000 | Say et al. |
| 6,103,275 A | 8/2000 | Seitz et al. |
| 6,105,442 A | 8/2000 | Kriesel et al. |
| 6,106,477 A | 8/2000 | Miesel et al. |
| 6,109,896 A | 8/2000 | Schuller et al. |
| 6,110,148 A | 8/2000 | Brown et al. |
| 6,110,149 A | 8/2000 | Klitgaard et al. |
| 6,110,152 A | 8/2000 | Kovelman |
| 6,110,427 A | 8/2000 | Uffenheimer |
| RE36,871 E | 9/2000 | Epstein et al. |
| 6,113,782 A | 9/2000 | Leonard |
| 6,117,122 A | 9/2000 | Din et al. |
| 6,120,460 A | 9/2000 | Abreu |
| 6,122,536 A | 9/2000 | Sun et al. |
| 6,123,175 A | 9/2000 | Fett |
| 6,123,686 A | 9/2000 | Olsen et al. |
| 6,126,642 A | 10/2000 | Kriesel et al. |
| 6,126,956 A | 10/2000 | Grossman et al. |
| 6,127,363 A | 10/2000 | Doherty, Jr. et al. |
| 6,132,686 A | 10/2000 | Gallup et al. |
| 6,135,196 A | 10/2000 | Kono |
| 6,135,949 A | 10/2000 | Russo et al. |
| 6,135,978 A | 10/2000 | Houben et al. |
| D433,755 S | 11/2000 | Mastrotaro et al. |
| 6,142,939 A | 11/2000 | Eppstein et al. |
| 6,143,238 A | 11/2000 | Konishi et al. |
| 6,143,252 A | 11/2000 | Haxo, Jr. et al. |
| 6,144,866 A | 11/2000 | Miesel et al. |
| 6,144,869 A | 11/2000 | Berner et al. |
| 6,145,625 A | 11/2000 | Prokop et al. |
| 6,146,361 A | 11/2000 | DiBiasi et al. |

(56) References Cited

U.S. PATENT DOCUMENTS

| | | |
|---|---|---|
| 6,147,070 A | 11/2000 | Facchini |
| 6,147,109 A | 11/2000 | Liao et al. |
| 6,152,898 A | 11/2000 | Olsen |
| 6,155,748 A | 12/2000 | Allen et al. |
| 6,156,753 A | 12/2000 | Doherty, Jr. et al. |
| 6,158,431 A | 12/2000 | Poole |
| 6,158,965 A | 12/2000 | Butterfield et al. |
| 6,163,721 A | 12/2000 | Thompson |
| 6,164,924 A | 12/2000 | Gruett et al. |
| 6,165,155 A | 12/2000 | Jacobson et al. |
| 6,167,290 A | 12/2000 | Yang et al. |
| 6,168,575 B1 | 1/2001 | Soultanpour |
| 6,175,752 B1 | 1/2001 | Say et al. |
| 6,176,692 B1 | 1/2001 | Reinartz et al. |
| 6,178,996 B1 | 1/2001 | Suzuki |
| 6,179,583 B1 | 1/2001 | Weston |
| 6,180,416 B1 | 1/2001 | Kurnik et al. |
| 6,180,597 B1 | 1/2001 | Liao et al. |
| 6,185,460 B1 | 2/2001 | Thompson |
| 6,186,982 B1 | 2/2001 | Gross et al. |
| 6,190,359 B1 | 2/2001 | Heruth |
| 6,198,383 B1 | 3/2001 | Sekura et al. |
| 6,202,708 B1 | 3/2001 | Bynum |
| 6,205,961 B1 | 3/2001 | Bailey et al. |
| 6,210,135 B1 | 4/2001 | Rassin et al. |
| 6,210,361 B1 | 4/2001 | Kamen et al. |
| 6,210,368 B1 | 4/2001 | Rogers |
| 6,210,957 B1 | 4/2001 | Carpentier et al. |
| 6,211,147 B1 | 4/2001 | Unemori |
| 6,211,426 B1 | 4/2001 | Abrams |
| 6,212,948 B1 | 4/2001 | Ekdahl et al. |
| 6,213,120 B1 | 4/2001 | Block et al. |
| 6,213,408 B1 | 4/2001 | Shekalim |
| 6,217,826 B1 | 4/2001 | Reeder et al. |
| 6,218,666 B1 | 4/2001 | Lukica et al. |
| 6,221,378 B1 | 4/2001 | Modi |
| 6,223,080 B1 | 4/2001 | Thompson |
| 6,223,703 B1 | 5/2001 | Galvin |
| 6,223,746 B1 | 5/2001 | Jewett et al. |
| 6,224,347 B1 | 5/2001 | Clark et al. |
| 6,224,352 B1 | 5/2001 | Hauser et al. |
| 6,225,999 B1 | 5/2001 | Jain et al. |
| 6,227,818 B1 | 5/2001 | Falk et al. |
| 6,228,044 B1 | 5/2001 | Jensen et al. |
| 6,229,584 B1 | 5/2001 | Chuo et al. |
| 6,231,545 B1 | 5/2001 | Kriesel et al. |
| 6,231,882 B1 | 5/2001 | Modi |
| 6,233,471 B1 | 5/2001 | Berner et al. |
| 6,236,887 B1 | 5/2001 | Ben-Hamin et al. |
| 6,238,423 B1 | 5/2001 | Bardy |
| 6,241,704 B1 | 6/2001 | Peterson et al. |
| 6,241,743 B1 | 6/2001 | Levin et al. |
| 6,245,347 B1 | 6/2001 | Zhang et al. |
| 6,247,493 B1 | 6/2001 | Henderson |
| 6,248,067 B1 | 6/2001 | Causey, III et al. |
| 6,248,093 B1 | 6/2001 | Moberg |
| 6,248,280 B1 | 6/2001 | Kern et al. |
| 6,251,098 B1 | 6/2001 | Rake et al. |
| 6,251,293 B1 | 6/2001 | Snodgrass et al. |
| 6,251,932 B1 | 6/2001 | Reicht et al. |
| 6,254,355 B1 | 7/2001 | Gharib |
| 6,254,569 B1 | 7/2001 | O'Donnell |
| 6,254,576 B1 | 7/2001 | Shekalim |
| 6,254,586 B1 | 7/2001 | Mann et al. |
| 6,256,533 B1 | 7/2001 | Yuzhakov et al. |
| 6,257,178 B1 | 7/2001 | Laimbock |
| 6,257,191 B1 | 7/2001 | Kutlucinar |
| 6,261,272 B1 | 7/2001 | Gross et al. |
| 6,261,280 B1 | 7/2001 | Houbin et al. |
| 6,264,439 B1 | 7/2001 | Falk et al. |
| 6,264,680 B1 | 7/2001 | Ash et al. |
| 6,266,564 B1 | 7/2001 | Hill et al. |
| 6,267,564 B1 | 7/2001 | Rapheal |
| 6,269,340 B1 | 7/2001 | Ford et al. |
| 6,270,478 B1 | 8/2001 | Mernoe |
| 6,272,364 B1 | 8/2001 | Kurnik |
| 6,275,717 B1 | 8/2001 | Gross et al. |
| 6,276,434 B1 | 8/2001 | Kono |
| 6,277,095 B1 | 8/2001 | Kriesel et al. |
| 6,277,097 B1 | 8/2001 | Mikkelsen et al. |
| 6,277,819 B1 | 8/2001 | Efendic |
| 6,280,408 B1 | 8/2001 | Sipin |
| 6,280,409 B1 | 8/2001 | Sipin |
| 6,280,416 B1 | 8/2001 | Van Antwerp et al. |
| 6,283,197 B1 | 8/2001 | Kono |
| 6,283,680 B1 | 9/2001 | Vidal |
| 6,283,943 B1 | 9/2001 | Dy et al. |
| 6,283,944 B1 | 9/2001 | McMullen et al. |
| 6,283,949 B1 | 9/2001 | Roorda |
| 6,284,725 B1 | 9/2001 | Coolidge et al. |
| 6,288,518 B1 | 9/2001 | Yang et al. |
| 6,289,248 B1 | 9/2001 | Conley |
| 6,290,683 B1 | 9/2001 | Erez et al. |
| 6,293,159 B1 | 9/2001 | Kriesel et al. |
| 6,293,242 B1 | 9/2001 | Kutlucinar |
| 6,293,429 B2 | 9/2001 | Sadler et al. |
| 6,293,756 B1 | 9/2001 | Andersson |
| 6,294,550 B1 | 9/2001 | Place et al. |
| 6,296,456 B1 | 10/2001 | Thornelow et al. |
| 6,296,623 B2 | 10/2001 | Spinello |
| 6,298,254 B2 | 10/2001 | Tamada |
| 6,298,760 B1 | 10/2001 | Danby |
| 6,298,941 B1 | 10/2001 | Spadafora |
| 6,299,415 B1 | 10/2001 | Bahrton |
| 6,299,578 B1 | 10/2001 | Kurnik et al. |
| 6,302,107 B1 | 10/2001 | Richey et al. |
| 6,302,653 B1 | 10/2001 | Bryant et al. |
| 6,302,855 B1 | 10/2001 | Novo Nordisk |
| 6,304,911 B1 | 10/2001 | Brcich et al. |
| 6,306,420 B1 | 10/2001 | Cheikh |
| 6,306,841 B1 | 10/2001 | Place et al. |
| 6,309,351 B1 | 10/2001 | Kurnik et al. |
| 6,309,371 B1 | 10/2001 | Deboer et al. |
| 6,310,270 B1 | 10/2001 | Huang et al. |
| 6,312,409 B1 | 11/2001 | Gross |
| 6,314,317 B1 | 11/2001 | Willis |
| 6,315,769 B1 | 11/2001 | Peer et al. |
| 6,319,215 B1 | 11/2001 | Peer et al. |
| 6,319,245 B1 | 11/2001 | Berrigan |
| 6,323,022 B1 | 11/2001 | Chang et al. |
| 6,325,999 B1 | 12/2001 | Bellgrau et al. |
| 6,327,964 B1 | 12/2001 | Schuller et al. |
| 6,328,004 B1 | 12/2001 | Rynhart |
| 6,331,172 B1 | 12/2001 | Epstein et al. |
| 6,334,761 B1 | 1/2002 | Tai et al. |
| 6,338,942 B2 | 1/2002 | Kraus et al. |
| 6,340,357 B1 | 1/2002 | Poulsen et al. |
| 6,340,421 B1 | 1/2002 | Vachon et al. |
| 6,340,783 B1 | 1/2002 | Snow |
| 6,341,232 B1 | 1/2002 | Conn et al. |
| 6,342,037 B1 | 1/2002 | Roe et al. |
| 6,342,484 B1 | 1/2002 | Kulkarni et al. |
| 6,344,457 B1 | 2/2002 | Jeanpetit et al. |
| 6,346,095 B1 | 2/2002 | Gross et al. |
| 6,349,783 B1 | 2/2002 | Galbraith et al. |
| 6,350,589 B1 | 2/2002 | Morris et al. |
| 6,355,030 B1 | 3/2002 | Aldrich et al. |
| 6,358,225 B1 | 3/2002 | Butterfield |
| 6,358,519 B1 | 3/2002 | Waterman |
| 6,360,888 B1 | 3/2002 | McIvor et al. |
| 6,362,591 B1 | 3/2002 | Moberg |
| 6,364,865 B1 | 4/2002 | Lavi et al. |
| 6,365,185 B1 | 4/2002 | Ritchel et al. |
| 6,365,628 B1 | 4/2002 | Berge |
| 6,366,808 B1 | 4/2002 | Schroppel et al. |
| 6,368,272 B1 | 4/2002 | Porumbescu |
| 6,368,314 B1 | 4/2002 | Kipfer et al. |
| 6,371,732 B1 | 4/2002 | Moubayed et al. |
| 6,372,182 B1 | 4/2002 | Mauro et al. |
| 6,372,508 B1 | 4/2002 | Schinzer et al. |
| 6,374,683 B1 | 4/2002 | Hunicke-Smith et al. |
| 6,374,876 B2 | 4/2002 | Bynum |
| 6,375,638 B2 | 4/2002 | Nason et al. |
| 6,381,493 B1 | 4/2002 | Stadler et al. |

(56) References Cited

U.S. PATENT DOCUMENTS

| | | |
|---|---|---|
| 6,382,923 B1 | 5/2002 | Gray |
| 6,393,318 B1 | 5/2002 | Conn et al. |
| 6,393,893 B1 | 5/2002 | Fetz et al. |
| 6,394,981 B2 | 5/2002 | Heruth |
| 6,395,292 B2 | 5/2002 | Peery et al. |
| 6,395,536 B2 | 5/2002 | Freeman |
| 6,397,199 B1 | 5/2002 | Goodwin, III |
| 6,398,718 B1 | 6/2002 | Yachia et al. |
| 6,398,760 B1 | 6/2002 | Danby |
| 6,399,024 B1 | 6/2002 | Bevirt et al. |
| 6,402,689 B1 | 6/2002 | Scarantino et al. |
| 6,406,455 B1 | 6/2002 | Willis et al. |
| 6,409,698 B1 | 6/2002 | Robinson |
| 6,412,273 B1 | 7/2002 | Rohs |
| 6,413,238 B1 | 7/2002 | Maget et al. |
| 6,413,254 B1 | 7/2002 | Hissong et al. |
| 6,415,961 B2 | 7/2002 | Bonnigue |
| 6,416,215 B1 | 7/2002 | Terentiev |
| 6,416,291 B1 | 7/2002 | Butterfield et al. |
| 6,416,293 B1 | 7/2002 | Bouchard et al. |
| 6,420,169 B1 | 7/2002 | Read et al. |
| 6,422,057 B1 | 7/2002 | Anderson |
| 6,422,256 B1 | 7/2002 | Balazy et al. |
| 6,423,029 B1 | 7/2002 | Elsberry |
| 6,423,035 B1 | 7/2002 | Das et al. |
| 6,423,344 B1 | 7/2002 | Platz et al. |
| 6,424,847 B1 | 7/2002 | Mastrototaro et al. |
| 6,425,740 B1 | 7/2002 | Jacobsen et al. |
| 6,425,878 B1 | 7/2002 | Shekalim |
| 6,427,088 B1 | 7/2002 | Bowman, IV et al. |
| 6,429,160 B1 | 7/2002 | Bloch |
| 6,428,491 B1 | 8/2002 | Weiss |
| 6,429,197 B1 | 8/2002 | Coolidge et al. |
| 6,429,230 B1 | 8/2002 | Cavazza |
| 6,429,232 B1 | 8/2002 | Kinsella et al. |
| 6,433,040 B1 | 8/2002 | Dellamary et al. |
| 6,436,072 B1 | 8/2002 | Kullas et al. |
| 6,436,078 B1 | 8/2002 | Svedman |
| 6,438,408 B1 | 8/2002 | Mulligan et al. |
| 6,438,414 B1 | 8/2002 | Conn et al. |
| 6,440,096 B1 | 8/2002 | Lastovich et al. |
| 6,441,036 B1 | 8/2002 | Berge |
| 6,442,433 B1 | 8/2002 | Linberg |
| 6,443,097 B1 | 9/2002 | Zohar et al. |
| 6,443,942 B2 | 9/2002 | Van Antwerp |
| 6,446,513 B1 | 9/2002 | Henderson |
| 6,447,443 B1 | 9/2002 | Keogh et al. |
| 6,447,446 B1 | 9/2002 | Smith et al. |
| 6,447,475 B1 | 9/2002 | Castellano et al. |
| 6,447,522 B2 | 9/2002 | Gambale et al. |
| 6,450,942 B1 | 9/2002 | Lapanashvili et al. |
| 6,450,953 B1 | 9/2002 | Place et al. |
| 6,454,707 B1 | 9/2002 | Casscells, III |
| 6,454,785 B2 | 9/2002 | De Hoyos Garza |
| 6,457,956 B1 | 10/2002 | Hauser et al. |
| 6,458,102 B1 | 10/2002 | Mann et al. |
| 6,458,109 B1 | 10/2002 | Henley et al. |
| 6,458,256 B1 | 10/2002 | Zhong |
| 6,458,762 B1 | 10/2002 | McKenzie et al. |
| 6,461,329 B1 | 10/2002 | Van Antwerp et al. |
| 6,461,331 B1 | 10/2002 | Van Antwerp |
| 6,461,334 B1 | 10/2002 | Buch-Rasmussen et al. |
| 6,461,828 B1 | 10/2002 | Stanton et al. |
| 6,463,794 B1 | 10/2002 | Moshe et al. |
| 6,464,667 B1 | 10/2002 | Kamen et al. |
| 6,467,267 B2 | 10/2002 | Kanazawa et al. |
| 6,468,200 B1 | 10/2002 | Fischi |
| 6,468,242 B1 | 10/2002 | Wilson et al. |
| 6,469,016 B1 | 10/2002 | Place et al. |
| 6,470,234 B1 | 10/2002 | McGrady |
| 6,471,496 B1 | 10/2002 | Merklein et al. |
| 6,471,689 B1 | 10/2002 | Joseph et al. |
| 6,471,855 B1 | 10/2002 | Odak et al. |
| 6,472,434 B1 | 10/2002 | Place et al. |
| 6,474,219 B2 | 11/2002 | Kitmose et al. |
| 6,475,180 B2 | 11/2002 | Peterson et al. |
| 6,475,750 B1 | 11/2002 | Han et al. |
| 6,477,774 B1 | 11/2002 | Marando et al. |
| 6,478,385 B1 | 11/2002 | Nishii et al. |
| 6,478,771 B1 | 11/2002 | Lavi et al. |
| 6,482,186 B1 | 11/2002 | Douglas et al. |
| 6,484,906 B2 | 11/2002 | Bonnigue |
| 6,485,263 B1 | 11/2002 | Bryant et al. |
| 6,485,452 B1 | 11/2002 | French et al. |
| 6,485,461 B1 | 11/2002 | Mason et al. |
| 6,485,463 B1 | 11/2002 | Yeh |
| 6,485,464 B1 | 11/2002 | Christenson et al. |
| 6,485,465 B2 | 11/2002 | Moberg et al. |
| 6,485,471 B1 | 11/2002 | Zivitz et al. |
| 6,488,652 B1 | 12/2002 | Weijand et al. |
| 6,488,697 B1 | 12/2002 | Ariura et al. |
| 6,489,346 B1 | 12/2002 | Phillips |
| 6,490,483 B2 | 12/2002 | Willis |
| 6,494,865 B1 | 12/2002 | Alchas |
| 6,500,150 B1 | 12/2002 | Gross et al. |
| 6,505,059 B1 | 1/2003 | Kollias et al. |
| 6,506,594 B1 | 1/2003 | Barany et al. |
| 6,508,788 B2 | 1/2003 | Preuthun |
| 6,511,435 B1 | 1/2003 | Bluth et al. |
| 6,512,949 B1 | 1/2003 | Combs et al. |
| 6,514,689 B2 | 2/2003 | Han et al. |
| 6,517,482 B1 | 2/2003 | Elden et al. |
| 6,520,936 B1 | 2/2003 | Mann |
| 6,520,938 B1 | 2/2003 | Funderburk et al. |
| 6,522,980 B1 | 2/2003 | Arnold |
| 6,583,111 B1 | 2/2003 | DiMarchi et al. |
| 6,530,900 B1 | 3/2003 | Daily et al. |
| 6,533,183 B2 | 3/2003 | Aasmul et al. |
| 6,535,714 B2 | 3/2003 | Melker et al. |
| 6,537,241 B1 | 3/2003 | Odland |
| 6,537,251 B2 | 3/2003 | Klitmose |
| 6,537,268 B1 | 3/2003 | Gibson et al. |
| 6,537,272 B2 | 3/2003 | Christopherson et al. |
| 6,540,006 B2 | 4/2003 | Kono |
| 6,540,161 B1 | 4/2003 | Gordon |
| 6,540,727 B2 | 4/2003 | Harper et al. |
| 6,540,996 B1 | 4/2003 | Zwaal et al. |
| 6,541,021 B1 | 4/2003 | Johnson et al. |
| 6,542,774 B2 | 4/2003 | Hill et al. |
| 6,542,775 B2 | 4/2003 | Ding et al. |
| 6,544,212 B2 | 4/2003 | Hill et al. |
| 6,544,229 B1 | 4/2003 | Danby et al. |
| 6,544,233 B1 | 4/2003 | Fukui et al. |
| 6,546,269 B1 | 4/2003 | Kurnik |
| 6,547,775 B1 | 4/2003 | Ding et al. |
| 6,550,245 B2 | 4/2003 | Nishii et al. |
| 6,551,276 B1 | 4/2003 | Mann et al. |
| 6,551,277 B1 | 4/2003 | Ford |
| 6,551,992 B1 | 4/2003 | DeFelippis et al. |
| 6,553,244 B2 | 4/2003 | Lesho et al. |
| 6,553,245 B1 | 4/2003 | Grace et al. |
| 6,554,798 B1 | 4/2003 | Mann et al. |
| 6,554,800 B1 | 4/2003 | Nezhadian et al. |
| 6,555,986 B2 | 4/2003 | Moberg |
| 6,557,454 B2 | 5/2003 | Miyazawa |
| 6,558,320 B1 | 5/2003 | Causey et al. |
| 6,558,351 B1 | 5/2003 | Steil et al. |
| 6,558,665 B1 | 5/2003 | Cohen et al. |
| 6,560,478 B1 | 5/2003 | Alfano et al. |
| 6,561,978 B1 | 5/2003 | Conn et al. |
| 6,562,001 B2 | 5/2003 | Lebel et al. |
| 6,562,011 B1 | 5/2003 | Buch-Rasmussen et al. |
| 6,564,093 B1 | 5/2003 | Ostrow et al. |
| 6,564,104 B2 | 5/2003 | Nelson et al. |
| 6,564,105 B2 | 5/2003 | Starkweather et al. |
| 6,565,802 B1 | 5/2003 | Hanley et al. |
| 6,565,872 B2 | 5/2003 | Wu et al. |
| 6,568,898 B2 | 5/2003 | Nishimura et al. |
| 6,568,922 B1 | 5/2003 | Winsel |
| 6,569,123 B2 | 5/2003 | Alchas et al. |
| 6,569,143 B2 | 5/2003 | Alchas et al. |
| 6,569,456 B2 | 5/2003 | Faour et al. |
| 6,571,128 B2 | 5/2003 | Lebel et al. |
| 6,558,345 B1 | 6/2003 | Houben et al. |

(56) References Cited

U.S. PATENT DOCUMENTS

| | | |
|---|---|---|
| 6,558,902 B1 | 6/2003 | Hillenkamp |
| 6,571,831 B1 | 6/2003 | Hart |
| 6,572,542 B1 | 6/2003 | Houben et al. |
| 6,572,566 B2 | 6/2003 | Effenhauser |
| 6,572,586 B1 | 6/2003 | Wojcik |
| 6,575,935 B1 | 6/2003 | Oliver et al. |
| 6,577,899 B2 | 6/2003 | Lebel et al. |
| 6,579,496 B1 | 6/2003 | Fausset et al. |
| 6,582,366 B1 | 6/2003 | Porumbescu |
| 6,582,393 B2 | 6/2003 | Sage, Jr. |
| 6,582,418 B1 | 6/2003 | Verbeek et al. |
| 6,585,644 B2 | 7/2003 | Lebel et al. |
| 6,585,695 B1 | 7/2003 | Adair et al. |
| 6,585,707 B2 | 7/2003 | Cabiri et al. |
| 6,587,705 B1 | 7/2003 | Kim et al. |
| 6,589,158 B2 | 7/2003 | Winkler |
| 6,589,229 B1 | 7/2003 | Connelly et al. |
| 6,592,544 B1 | 7/2003 | Mooney et al. |
| 6,592,571 B1 | 7/2003 | Verbeek et al. |
| 6,592,860 B1 | 7/2003 | Levy et al. |
| 6,592,904 B2 | 7/2003 | Platz et al. |
| 6,593,313 B2 | 7/2003 | Place et al. |
| 6,594,514 B2 | 7/2003 | Berner et al. |
| 6,594,634 B1 | 7/2003 | Hampton et al. |
| 6,595,756 B2 | 7/2003 | Gray et al. |
| 6,595,919 B2 | 7/2003 | Berner et al. |
| 6,595,948 B2 | 7/2003 | Suzuki et al. |
| 6,595,956 B1 | 7/2003 | Gross et al. |
| 6,599,281 B1 | 7/2003 | Struys et al. |
| 6,602,241 B2 | 8/2003 | Makower et al. |
| 6,604,908 B1 | 8/2003 | Bryant et al. |
| 6,605,072 B2 | 8/2003 | Struys et al. |
| 6,607,513 B1 | 8/2003 | Down et al. |
| 6,607,658 B1 | 8/2003 | Heller et al. |
| 6,607,739 B1 | 8/2003 | Wallo |
| 6,610,003 B1 | 8/2003 | Meloul et al. |
| 6,612,535 B1 | 9/2003 | Tai et al. |
| 6,613,019 B2 | 9/2003 | Munk |
| 6,616,196 B1 | 9/2003 | Weh et al. |
| 6,616,627 B2 | 9/2003 | Willis et al. |
| 6,618,603 B2 | 9/2003 | Varalli et al. |
| 6,620,140 B1 | 9/2003 | Metzger |
| 6,620,379 B1 | 9/2003 | Piuk et al. |
| 6,623,698 B2 | 9/2003 | Kuo |
| 6,625,479 B1 | 9/2003 | Weber et al. |
| 6,626,644 B2 | 9/2003 | Ozaki |
| 6,629,934 B2 | 10/2003 | Mault et al. |
| 6,629,938 B1 | 10/2003 | Engvall et al. |
| 6,629,949 B1 | 10/2003 | Douglas |
| 6,629,954 B1 | 10/2003 | Heruth |
| 6,634,939 B2 | 10/2003 | Johnson |
| 6,635,014 B2 | 10/2003 | Starkweather et al. |
| 6,635,048 B1 | 10/2003 | Ullestad et al. |
| 6,636,796 B2 | 10/2003 | Kolmanovsky et al. |
| 6,639,381 B2 | 10/2003 | Tamura et al. |
| 6,641,533 B2 | 11/2003 | Causey et al. |
| 6,641,562 B1 | 11/2003 | Peterson |
| 6,641,565 B1 | 11/2003 | Lavi et al. |
| 6,641,566 B2 | 11/2003 | Douglas et al. |
| 6,642,019 B1 | 11/2003 | Anderson et al. |
| 6,645,176 B1 | 11/2003 | Christenson et al. |
| 6,645,181 B1 | 11/2003 | Lavi et al. |
| 6,645,448 B2 | 11/2003 | Cho et al. |
| 6,648,821 B2 | 11/2003 | Lebel et al. |
| 6,648,859 B2 | 11/2003 | Bitdinger et al. |
| 6,648,861 B2 | 11/2003 | Platt et al. |
| 6,649,403 B1 | 11/2003 | McDevitt et al. |
| 6,650,919 B2 | 11/2003 | Edelberg et al. |
| 6,650,951 B1 | 11/2003 | Jones et al. |
| 6,651,546 B2 | 11/2003 | Sandlin |
| 6,652,493 B1 | 11/2003 | Das |
| 6,652,510 B2 | 11/2003 | Lord et al. |
| 6,653,091 B1 | 11/2003 | Dunn et al. |
| 6,656,114 B1 | 12/2003 | Poulsen et al. |
| 6,656,148 B2 | 12/2003 | Das et al. |
| 6,656,158 B2 | 12/2003 | Manhoney et al. |
| 6,656,159 B2 | 12/2003 | Flaherty et al. |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,359 B2 | 12/2003 | Gray |
| 6,663,602 B2 | 12/2003 | Moller |
| 6,666,021 B1 | 12/2003 | Keimel |
| 6,666,665 B1 | 12/2003 | Nguyen et al. |
| 6,666,821 B2 | 12/2003 | Keimel |
| 6,668,196 B1 | 12/2003 | Villegas et al. |
| 6,668,701 B1 | 12/2003 | Everitt |
| 6,669,663 B1 | 12/2003 | Thompson |
| 6,669,669 B2 | 12/2003 | Flaherty et al. |
| 6,673,033 B1 | 1/2004 | Sciulli et al. |
| 6,676,387 B1 | 1/2004 | Penn |
| 6,677,320 B2 | 1/2004 | Diederich et al. |
| 6,679,865 B2 | 1/2004 | Shekalim |
| 6,682,497 B2 | 1/2004 | Jensen et al. |
| 6,683,690 B1 | 1/2004 | Tobias |
| 6,687,522 B2 | 2/2004 | Tamada |
| 6,687,546 B2 | 2/2004 | Lebel et al. |
| 6,689,100 B2 | 2/2004 | Connelly et al. |
| 6,689,108 B2 | 2/2004 | Lavi et al. |
| 6,689,118 B2 | 2/2004 | Alchas et al. |
| 6,689,373 B2 | 2/2004 | Johnson et al. |
| 6,692,456 B1 | 2/2004 | Eppstein et al. |
| 6,692,457 B2 | 2/2004 | Flaherty et al. |
| 6,692,472 B2 | 2/2004 | Hansen et al. |
| 6,692,473 B2 | 2/2004 | St. Cyr et al. |
| 6,694,191 B2 | 2/2004 | Starkweather et al. |
| 6,695,011 B2 | 2/2004 | Sochtig |
| 6,696,090 B1 | 2/2004 | Nilsson et al. |
| 6,696,493 B2 | 2/2004 | Cavazza |
| 6,699,218 B2 | 3/2004 | Flaherty et al. |
| 6,699,234 B2 | 3/2004 | Yeh et al. |
| 6,699,885 B2 | 3/2004 | Phillips |
| 6,702,779 B2 | 3/2004 | Connelly et al. |
| 6,702,857 B2 | 3/2004 | Brauker et al. |
| 6,705,845 B2 | 3/2004 | Kreiger et al. |
| 6,706,008 B2 | 3/2004 | Vishnoi et al. |
| 6,706,009 B2 | 3/2004 | Diermann et al. |
| 6,706,689 B2 | 3/2004 | Coolidge et al. |
| 6,710,051 B1 | 3/2004 | Trier |
| 6,711,489 B2 | 3/2004 | Hasakara et al. |
| 6,712,095 B2 | 3/2004 | Williamson et al. |
| 6,715,516 B2 | 4/2004 | Ohms et al. |
| 6,716,190 B1 | 4/2004 | Glines et al. |
| 6,716,198 B2 | 4/2004 | Larsen |
| 6,718,206 B2 | 4/2004 | Casavante |
| 6,719,302 B2 | 4/2004 | Andrick |
| 6,723,068 B2 | 4/2004 | Lavi et al. |
| 6,723,072 B2 | 4/2004 | Flaherty et al. |
| 6,726,920 B1 | 4/2004 | Theeuwes et al. |
| 6,732,573 B2 | 5/2004 | Shin et al. |
| 6,733,446 B2 | 5/2004 | Lebel et al. |
| 6,734,186 B1 | 5/2004 | Maw et al. |
| 6,736,796 B2 | 5/2004 | Shekalim et al. |
| 6,738,052 B1 | 5/2004 | Manke et al. |
| 6,738,663 B2 | 5/2004 | Schroppel et al. |
| 6,738,707 B2 | 5/2004 | Kotwicki et al. |
| 6,740,059 B2 | 5/2004 | Flaherty et al. |
| 6,740,072 B2 | 5/2004 | Starkweather et al. |
| 6,740,075 B2 | 5/2004 | Lebel et al. |
| 6,743,201 B1 | 6/2004 | Doenig et al. |
| 6,744,152 B2 | 6/2004 | Kroll |
| 6,744,350 B2 | 6/2004 | Blomquist |
| 6,745,079 B2 | 6/2004 | King |
| 6,746,438 B1 | 6/2004 | Arnissolle |
| 6,748,930 B2 | 6/2004 | Bofinger et al. |
| 6,749,403 B2 | 6/2004 | Bryant et al. |
| 6,749,587 B2 | 6/2004 | Flaherty et al. |
| 6,752,785 B2 | 6/2004 | Van Antwerp et al. |
| 6,752,787 B1 | 6/2004 | Causey, III et al. |
| 6,755,628 B1 | 6/2004 | Howell |
| 6,755,810 B1 | 6/2004 | Buch-Rasmussen et al. |
| 6,758,593 B1 | 7/2004 | Terentiev |
| 6,758,810 B2 | 7/2004 | Lebel et al. |
| 6,759,386 B2 | 7/2004 | Franco |

(56) References Cited

U.S. PATENT DOCUMENTS

| | | |
|---|---|---|
| 6,767,188 B2 | 7/2004 | Vrane et al. |
| 6,767,896 B1 | 7/2004 | McIntosh et al. |
| 6,768,425 B2 | 7/2004 | Flaherty et al. |
| 6,769,384 B2 | 8/2004 | Dougherty |
| 6,770,054 B1 | 8/2004 | Smolyarov et al. |
| 6,770,067 B2 | 8/2004 | Lorenzen et al. |
| 6,773,669 B1 | 8/2004 | Holaday et al. |
| 6,773,739 B2 | 8/2004 | Hauck et al. |
| 6,775,577 B2 | 8/2004 | Crnkovich et al. |
| 6,776,776 B2 | 8/2004 | Alchas et al. |
| 6,780,156 B2 | 8/2004 | Haueter et al. |
| 6,780,171 B2 | 8/2004 | Gabel et al. |
| 6,780,426 B2 | 8/2004 | Zhang et al. |
| 6,780,770 B2 | 8/2004 | Larson |
| 6,780,836 B2 | 8/2004 | Unemori |
| 6,783,107 B2 | 8/2004 | Chatufale |
| 6,783,328 B2 | 8/2004 | Lucke et al. |
| 6,786,246 B2 | 9/2004 | Ohms et al. |
| 6,790,670 B2 | 9/2004 | Munagavalasa et al. |
| 6,796,956 B2 | 9/2004 | Hartlaub et al. |
| 6,801,420 B2 | 10/2004 | Talbot et al. |
| 6,804,002 B2 | 10/2004 | Fine et al. |
| 6,804,555 B2 | 10/2004 | Warkentin |
| 6,805,122 B2 | 10/2004 | Richey, II et al. |
| 6,805,687 B2 | 10/2004 | Dextradeur et al. |
| 6,808,506 B2 | 10/2004 | Lastovich et al. |
| 6,809,653 B1 | 10/2004 | Mann et al. |
| 6,810,290 B2 | 10/2004 | Lebel et al. |
| RE38,654 E | 11/2004 | Hill et al. |
| 6,811,533 B2 | 11/2004 | Lebel et al. |
| 6,811,534 B2 | 11/2004 | Bowman, IV et al. |
| 6,811,792 B2 | 11/2004 | Roser et al. |
| 6,813,519 B2 | 11/2004 | Lebel et al. |
| 6,813,964 B1 | 11/2004 | Clark et al. |
| 6,814,547 B2 | 11/2004 | Childers et al. |
| 6,821,249 B2 | 11/2004 | Casscells, III et al. |
| 6,821,484 B1 | 11/2004 | Gregersen |
| 6,824,529 B2 | 11/2004 | Gross et al. |
| 6,827,524 B2 | 12/2004 | Starry, Jr. et al. |
| 6,827,702 B2 | 12/2004 | Lebel et al. |
| 6,827,710 B1 | 12/2004 | Mooney et al. |
| 6,827,898 B1 | 12/2004 | Fausset et al. |
| 6,828,552 B2 | 12/2004 | Hartley |
| 6,830,558 B2 | 12/2004 | Flaherty et al. |
| 6,830,560 B1 | 12/2004 | Gross et al. |
| 6,835,175 B1 | 12/2004 | Porumbescu |
| 6,835,194 B2 | 12/2004 | Johnson et al. |
| 6,842,042 B2 | 1/2005 | Vanhout |
| 6,842,642 B2 | 1/2005 | Vanhout |
| 6,843,782 B2 | 1/2005 | Gross et al. |
| 6,847,898 B1 | 1/2005 | Chen et al. |
| 6,851,449 B2 | 2/2005 | Kleibrink |
| 6,852,104 B2 | 2/2005 | Blomquist |
| 6,852,487 B1 | 2/2005 | Barany et al. |
| 6,854,432 B2 | 2/2005 | Hirano |
| 6,854,620 B2 | 2/2005 | Ramey |
| 6,858,011 B2 | 2/2005 | Sehgal |
| 6,858,403 B2 | 2/2005 | Han et al. |
| 6,859,673 B2 | 2/2005 | Steffen |
| 6,862,466 B2 | 3/2005 | Ackerman |
| 6,864,101 B1 | 3/2005 | Winkler et al. |
| 6,867,196 B1 | 3/2005 | Wolff et al. |
| 6,868,358 B2 | 3/2005 | Brown, Jr. |
| 6,872,200 B2 | 3/2005 | Mann et al. |
| 6,873,268 B2 | 3/2005 | Lebel et al. |
| 6,876,885 B2 | 4/2005 | Swoyer et al. |
| 6,877,713 B1 | 4/2005 | Gray et al. |
| 6,880,564 B2 | 4/2005 | Erickson |
| 6,882,940 B2 | 4/2005 | Potts et al. |
| 6,884,122 B2 | 4/2005 | Robinson et al. |
| 6,884,228 B2 | 4/2005 | Brown et al. |
| 6,885,881 B2 | 4/2005 | Leonhardt |
| 6,885,888 B2 | 4/2005 | Rezai |
| 6,886,556 B2 | 5/2005 | Fuchs |
| 6,892,755 B2 | 5/2005 | Black |
| 6,892,900 B2 | 5/2005 | Drechsel |
| 6,893,415 B2 | 5/2005 | Madsen et al. |
| 6,894,024 B2 | 5/2005 | Coolidge et al. |
| 6,895,263 B2 | 5/2005 | Shin et al. |
| 6,896,666 B2 | 5/2005 | Kochamba |
| 6,899,699 B2 | 5/2005 | Enggaard |
| RE38,749 E | 6/2005 | Dardik |
| 6,902,905 B2 | 6/2005 | Burson et al. |
| 6,905,314 B2 | 6/2005 | Danby |
| 6,905,479 B1 | 6/2005 | Bouchard et al. |
| 6,906,028 B2 | 6/2005 | DeFelippis et al. |
| 6,908,591 B2 | 6/2005 | MacPhee et al. |
| 6,909,840 B2 | 6/2005 | Harwig et al. |
| 6,912,425 B2 | 6/2005 | Nova et al. |
| 6,913,933 B2 | 7/2005 | Jacobs et al. |
| 6,914,076 B2 | 7/2005 | Cavazza |
| 6,916,010 B2 | 7/2005 | Beck et al. |
| 6,916,159 B2 | 7/2005 | Rush et al. |
| 6,918,542 B2 | 7/2005 | Silverbrook et al. |
| 6,923,006 B2 | 8/2005 | Walton |
| 6,923,180 B2 | 8/2005 | Richey, II et al. |
| 6,923,764 B2 | 8/2005 | Aceti et al. |
| 6,926,694 B2 | 8/2005 | Marano-Ford et al. |
| 6,928,338 B1 | 8/2005 | Buchser et al. |
| 6,930,093 B2 | 8/2005 | Brantl |
| 6,931,845 B2 | 8/2005 | Schaeffer |
| 6,931,925 B2 | 8/2005 | Huemer et al. |
| 6,932,114 B2 | 8/2005 | Sparks |
| 6,932,584 B2 | 8/2005 | Gray et al. |
| 6,932,796 B2 | 8/2005 | Sage et al. |
| 6,935,531 B1 | 8/2005 | Clayton |
| 6,935,539 B2 | 8/2005 | Krieger et al. |
| 6,936,026 B2 | 8/2005 | Diermann et al. |
| 6,936,029 B2 | 8/2005 | Mann et al. |
| 6,936,035 B2 | 8/2005 | Rake et al. |
| 6,936,046 B2 | 8/2005 | Hissong et al. |
| 6,939,323 B2 | 9/2005 | Angel et al. |
| 6,939,324 B2 | 9/2005 | Gonneli et al. |
| 6,942,636 B2 | 9/2005 | Holst et al. |
| 6,943,034 B1 | 9/2005 | Winkler et al. |
| 6,945,760 B2 | 9/2005 | Gray et al. |
| 6,946,117 B1 | 9/2005 | Schutt et al. |
| 6,948,918 B2 | 9/2005 | Hansen |
| 6,949,081 B1 | 9/2005 | Chance |
| 6,950,708 B2 | 9/2005 | Bowman IV et al. |
| 6,951,165 B2 | 10/2005 | Kuhn et al. |
| 6,951,553 B2 | 10/2005 | Bubb et al. |
| 6,952,604 B2 | 10/2005 | DeNuzzio et al. |
| 6,952,963 B2 | 10/2005 | Delnevo |
| 6,953,323 B2 | 10/2005 | Childers et al. |
| 6,955,819 B2 | 10/2005 | Zhang et al. |
| 6,955,915 B2 | 10/2005 | Fodor et al. |
| 6,956,204 B2 | 10/2005 | Dong et al. |
| 6,957,655 B2 | 10/2005 | Erickson et al. |
| 6,957,924 B1 | 10/2005 | McMeekin et al. |
| 6,958,073 B2 | 10/2005 | Rogers et al. |
| 6,958,691 B1 | 10/2005 | Anderson et al. |
| 6,958,705 B2 | 10/2005 | Lebel et al. |
| 6,960,184 B2 | 11/2005 | Willis et al. |
| 6,960,192 B1 | 11/2005 | Flaherty et al. |
| 6,962,103 B2 | 11/2005 | Sandlin |
| 6,962,151 B1 | 11/2005 | Knoch et al. |
| 6,963,770 B2 | 11/2005 | Scarantino et al. |
| 6,964,356 B2 | 11/2005 | Kim |
| 6,966,325 B2 | 11/2005 | Erickson |
| 6,966,895 B2 | 11/2005 | Tribe |
| 6,969,369 B2 | 11/2005 | Struble |
| 6,970,741 B1 | 11/2005 | Whitehurst et al. |
| 6,970,742 B2 | 11/2005 | Mann et al. |
| 6,971,999 B2 | 12/2005 | Py et al. |
| 6,973,374 B2 | 12/2005 | Ader |
| 6,974,055 B2 | 12/2005 | Moore et al. |
| 6,974,115 B2 | 12/2005 | Silva |
| 6,974,437 B2 | 12/2005 | Lebel et al. |
| 6,974,438 B2 | 12/2005 | Shekalim |
| 6,974,588 B1 | 12/2005 | Miranda et al. |
| 6,979,308 B1 | 12/2005 | MacDonald et al. |
| 6,979,315 B2 | 12/2005 | Rogers et al. |
| 6,979,316 B1 | 12/2005 | Rubin et al. |

(56) References Cited

U.S. PATENT DOCUMENTS

| | | |
|---|---|---|
| 6,979,326 B2 | 12/2005 | Mann et al. |
| 6,980,855 B2 | 12/2005 | Cho |
| 6,981,499 B2 | 1/2006 | Anderson et al. |
| 6,981,967 B2 | 1/2006 | Massengale et al. |
| 6,982,248 B2 | 1/2006 | Coolidge et al. |
| 6,983,209 B2 | 1/2006 | Jaynes |
| 6,985,770 B2 | 1/2006 | Nyhart, Jr. |
| 6,985,771 B2 | 1/2006 | Fischell et al. |
| 6,986,867 B2 | 1/2006 | Hanley et al. |
| 6,987,129 B2 | 1/2006 | Mak et al. |
| 6,990,809 B2 | 1/2006 | Abouraphael |
| 6,991,619 B2 | 1/2006 | Marano-Ford et al. |
| 6,991,620 B2 | 1/2006 | Marano-Ford et al. |
| 6,993,795 B2 | 2/2006 | Prineppi |
| 6,994,691 B2 | 2/2006 | Ejlersen |
| 6,994,700 B2 | 2/2006 | Elkins et al. |
| 6,997,202 B2 | 2/2006 | Olander |
| 6,997,905 B2 | 2/2006 | Gillespie, Jr. et al. |
| 6,997,911 B2 | 2/2006 | Klitmose |
| 6,997,916 B2 | 2/2006 | Simas, Jr. et al. |
| 6,997,920 B2 | 2/2006 | Mann et al. |
| 6,997,921 B2 | 2/2006 | Gray et al. |
| 6,998,387 B1 | 2/2006 | Goke et al. |
| 6,998,404 B2 | 2/2006 | Moskowitz |
| 6,999,810 B2 | 2/2006 | Berner et al. |
| 6,999,854 B2 | 2/2006 | Roth |
| 7,003,336 B2 | 2/2006 | Holker et al. |
| 7,004,928 B2 | 2/2006 | Aceti et al. |
| 7,008,399 B2 | 3/2006 | Larson et al. |
| 7,008,403 B1 | 3/2006 | Mallett |
| 7,008,413 B2 | 3/2006 | Kovach et al. |
| 7,010,340 B2 | 3/2006 | Scarantino et al. |
| 7,011,630 B2 | 3/2006 | Desai et al. |
| 7,011,682 B2 | 3/2006 | Lashinski et al. |
| 7,013,727 B2 | 3/2006 | Delnevo |
| 7,015,782 B2 | 3/2006 | Kincaid et al. |
| 7,018,336 B2 | 3/2006 | Enegren et al. |
| 7,018,360 B2 | 3/2006 | Flaherty et al. |
| 7,018,361 B2 | 3/2006 | Gillespie, Jr. et al. |
| 7,018,630 B2 | 3/2006 | Takaoka |
| 7,022,071 B2 | 4/2006 | Schaupp et al. |
| 7,022,072 B2 | 4/2006 | Fox et al. |
| 7,022,087 B2 | 4/2006 | Dempster et al. |
| 7,022,108 B2 | 4/2006 | Marano-Ford et al. |
| 7,024,244 B2 | 4/2006 | Muhlenberg et al. |
| 7,024,245 B2 | 4/2006 | Lebel et al. |
| 7,025,716 B1 | 4/2006 | Meloul et al. |
| 7,025,743 B2 | 4/2006 | Mann et al. |
| 7,027,478 B2 | 4/2006 | Ackley |
| 7,027,871 B2 | 4/2006 | Burnes et al. |
| 7,029,455 B2 | 4/2006 | Flaherty |
| 7,031,772 B2 | 4/2006 | Condie et al. |
| 7,033,338 B2 | 4/2006 | Vilks et al. |
| 7,033,539 B2 | 4/2006 | Krensky et al. |
| 7,033,843 B2 | 4/2006 | Hasegawa et al. |
| 7,011,647 B2 | 5/2006 | Purdy et al. |
| 7,041,082 B2 | 5/2006 | Blomquist et al. |
| 7,047,070 B2 | 5/2006 | Wilkinson et al. |
| 7,048,193 B2 | 5/2006 | Tsukada et al. |
| 7,048,951 B1 | 5/2006 | Seitz et al. |
| 7,052,251 B2 | 5/2006 | Nason et al. |
| 7,052,483 B2 | 5/2006 | Wojcik |
| 7,053,761 B2 | 5/2006 | Schofield et al. |
| 7,056,179 B2 | 6/2006 | Courtney |
| 7,056,302 B2 | 6/2006 | Douglas |
| 7,056,494 B2 | 6/2006 | Adjei et al. |
| 7,056,887 B2 | 6/2006 | Coolidge et al. |
| 7,058,438 B2 | 6/2006 | Grace et al. |
| 7,059,348 B2 | 6/2006 | Nat |
| 7,060,856 B2 | 6/2006 | Macikenas et al. |
| 7,063,684 B2 | 6/2006 | Moberg |
| 7,064,472 B2 | 6/2006 | Pelrine et al. |
| 7,066,359 B2 | 6/2006 | Greiner-Perth |
| 7,066,910 B2 | 6/2006 | Bauhahn et al. |
| 7,066,915 B2 | 6/2006 | Olsen |
| 7,066,922 B2 | 6/2006 | Angel et al. |
| 7,069,075 B2 | 6/2006 | Olson |
| 7,070,577 B1 | 7/2006 | Haller et al. |
| 7,072,802 B2 | 7/2006 | Hartlaub |
| 7,073,485 B2 | 7/2006 | Truscott et al. |
| 7,073,713 B2 | 7/2006 | Silverbrook et al. |
| 7,074,200 B2 | 7/2006 | Lewis |
| 7,077,822 B1 | 7/2006 | Howard, III |
| 7,078,163 B2 | 7/2006 | Torrianni |
| 7,081,105 B2 | 7/2006 | Reilly et al. |
| 7,082,333 B1 | 7/2006 | Bauhahn et al. |
| 7,082,812 B2 | 8/2006 | Lenormand et al. |
| 7,083,108 B2 | 8/2006 | Silverbrook et al. |
| 7,083,592 B2 | 8/2006 | Lastovich et al. |
| 7,083,599 B2 | 8/2006 | Alchas et al. |
| 7,089,608 B2 | 8/2006 | Erb |
| 7,090,648 B2 | 8/2006 | Sackner et al. |
| 7,091,179 B2 | 8/2006 | Franco |
| 7,092,011 B2 | 8/2006 | Silverbrook et al. |
| 7,092,796 B2 | 8/2006 | Vanderveen |
| 7,095,210 B2 | 8/2006 | Tamura et al. |
| 7,096,889 B1 | 8/2006 | Roys |
| 7,097,104 B2 | 8/2006 | Silverbrook et al. |
| 7,098,803 B2 | 8/2006 | Mann et al. |
| 7,104,973 B2 | 9/2006 | Woolston et al. |
| 7,104,981 B2 | 9/2006 | Elkins et al. |
| 7,107,706 B1 | 9/2006 | Bailey, Sr. et al. |
| 7,107,837 B2 | 9/2006 | Lauman et al. |
| 7,108,491 B2 | 9/2006 | Ganser |
| 7,108,679 B2 | 9/2006 | Alchas |
| 7,109,878 B2 | 9/2006 | Mann et al. |
| 7,111,346 B2 | 9/2006 | Inman et al. |
| 7,115,108 B2 | 10/2006 | Wilkinson et al. |
| 7,118,351 B2 | 10/2006 | Effenhauser et al. |
| 7,118,676 B2 | 10/2006 | Mueth et al. |
| 7,122,151 B2 | 10/2006 | Reeder et al. |
| 7,127,292 B2 | 10/2006 | Warman et al. |
| 7,128,727 B2 | 10/2006 | Flaherty et al. |
| 7,128,730 B2 | 10/2006 | Marano-Ford et al. |
| 7,131,967 B2 | 11/2006 | Gray et al. |
| 7,133,329 B2 | 11/2006 | Skyggebjerg et al. |
| 7,136,701 B2 | 11/2006 | Greatbatch et al. |
| 7,137,951 B2 | 11/2006 | Pilarski |
| 7,137,964 B2 | 11/2006 | Flaherty et al. |
| 7,138,141 B2 | 11/2006 | Platz et al. |
| 7,140,332 B2 | 11/2006 | Klein et al. |
| 7,141,425 B2 | 11/2006 | Dzekunov et al. |
| 7,141,812 B2 | 11/2006 | Appleby et al. |
| 7,144,384 B2 | 12/2006 | Gorman et al. |
| 7,144,729 B2 | 12/2006 | Rolland et al. |
| 7,147,386 B2 | 12/2006 | Zhang et al. |
| 7,147,839 B2 | 12/2006 | Sampath et al. |
| 7,150,409 B2 | 12/2006 | Gonneli et al. |
| 7,150,724 B2 | 12/2006 | Morris et al. |
| 7,150,726 B2 | 12/2006 | Dalton |
| 7,150,737 B2 | 12/2006 | Purdy et al. |
| 7,150,741 B2 | 12/2006 | Erickson et al. |
| 7,152,673 B2 | 12/2006 | Lohbeck |
| 7,153,286 B2 | 12/2006 | Busby et al. |
| 7,153,823 B2 | 12/2006 | Franco |
| 7,156,808 B2 | 1/2007 | Quy |
| 7,156,838 B2 | 1/2007 | Gabel et al. |
| 7,159,271 B2 | 1/2007 | Sepke et al. |
| 7,162,303 B2 | 1/2007 | Levin et al. |
| 7,163,385 B2 | 1/2007 | Gharib et al. |
| 7,163,520 B2 | 1/2007 | Bernard et al. |
| 7,166,280 B2 | 1/2007 | Franco |
| 7,171,274 B2 | 1/2007 | Starkweather et al. |
| 7,174,199 B2 | 2/2007 | Berner et al. |
| 7,179,226 B2 | 2/2007 | Crothall et al. |
| 7,181,505 B2 | 2/2007 | Haller et al. |
| 7,183,068 B2 | 2/2007 | Burson et al. |
| 7,186,236 B2 | 3/2007 | Gibson et al. |
| 7,187,404 B2 | 3/2007 | Silverbrook et al. |
| 7,187,528 B2 | 3/2007 | Talbot et al. |
| 7,187,969 B2 | 3/2007 | Willis |
| 7,189,352 B2 | 3/2007 | Carpenter et al. |
| 7,193,521 B2 | 3/2007 | Moberg et al. |
| 7,194,890 B2 | 3/2007 | Tanaka et al. |

(56) References Cited

U.S. PATENT DOCUMENTS

| | | |
|---|---|---|
| 7,195,616 B2 | 3/2007 | Diller et al. |
| 7,198,603 B2 | 4/2007 | Penner et al. |
| 7,198,637 B2 | 4/2007 | Deshmukh et al. |
| 7,198,751 B2 | 4/2007 | Carpenter et al. |
| 7,198,940 B2 | 4/2007 | Vellinger et al. |
| 7,201,319 B2 | 4/2007 | Silverbrook et al. |
| 7,201,730 B2 | 4/2007 | Davidner et al. |
| 7,204,823 B2 | 4/2007 | Estes et al. |
| 7,204,958 B2 | 4/2007 | Olsen et al. |
| 7,207,952 B2 | 4/2007 | Takinami et al. |
| 7,207,964 B2 | 4/2007 | Davidner et al. |
| 7,208,119 B1 | 4/2007 | Kurtock et al. |
| 7,208,120 B2 | 4/2007 | Bitensky et al. |
| 7,214,207 B2 | 5/2007 | Lynch et al. |
| 7,214,221 B2 | 5/2007 | Fentress et al. |
| 7,214,658 B2 | 5/2007 | Tobinick |
| 7,217,699 B2 | 5/2007 | Yakubov |
| 7,217,796 B2 | 5/2007 | Wang et al. |
| 7,220,109 B2 | 5/2007 | Kultgen |
| 7,220,236 B2 | 5/2007 | Pan |
| 7,220,248 B2 | 5/2007 | Mernoe et al. |
| 7,220,365 B2 | 5/2007 | Qu et al. |
| 7,224,815 B2 | 5/2007 | Maltan et al. |
| 7,225,807 B2 | 6/2007 | Papania et al. |
| 7,226,278 B2 | 6/2007 | Nason et al. |
| 7,226,910 B2 | 6/2007 | Wilson et al. |
| 7,229,288 B2 | 6/2007 | Stuart et al. |
| 7,231,263 B2 | 6/2007 | Choi |
| 7,232,423 B2 | 6/2007 | Mernoe et al. |
| 7,232,430 B2 | 6/2007 | Carlisle et al. |
| 7,232,435 B2 | 6/2007 | Hildebrand et al. |
| 7,234,645 B2 | 6/2007 | Silverbrook |
| 7,235,164 B2 | 6/2007 | Anex et al. |
| 7,235,583 B1 | 6/2007 | Webb et al. |
| 7,237,694 B2 | 7/2007 | Freudinger |
| 7,238,165 B2 | 7/2007 | Vincent et al. |
| 7,239,941 B2 | 7/2007 | Mori et al. |
| 7,244,225 B2 | 7/2007 | Loeb et al. |
| 7,244,354 B2 | 7/2007 | Burris et al. |
| 7,247,138 B2 | 7/2007 | Reghabi et al. |
| 7,247,428 B2 | 7/2007 | Makrigiorgos |
| 7,247,702 B2 | 7/2007 | Gardner et al. |
| 7,250,037 B2 | 7/2007 | Shermer et al. |
| 7,251,516 B2 | 7/2007 | Walker et al. |
| 7,252,014 B1 | 8/2007 | Mayer et al. |
| 7,252,651 B2 | 8/2007 | Haider et al. |
| 7,254,782 B1 | 8/2007 | Sherer |
| 7,255,690 B2 | 8/2007 | Gray et al. |
| 7,256,771 B2 | 8/2007 | Novak et al. |
| 7,256,824 B2 | 8/2007 | Silverbrook et al. |
| 7,256,888 B2 | 8/2007 | Staehr et al. |
| 7,258,864 B2 | 8/2007 | Clark |
| RE39,816 E | 9/2007 | Stanton et al. |
| 7,264,730 B2 | 9/2007 | Connell et al. |
| 7,265,091 B2 | 9/2007 | Lue et al. |
| 7,267,665 B2 | 9/2007 | Steil et al. |
| 7,267,753 B2 | 9/2007 | Anex et al. |
| 7,267,771 B2 | 9/2007 | Gorsuch et al. |
| 7,268,859 B2 | 9/2007 | Sage, Jr. et al. |
| 7,272,544 B2 | 9/2007 | Gopal et al. |
| 7,276,027 B2 | 10/2007 | Haar et al. |
| 7,276,057 B2 | 10/2007 | Gerber |
| 7,278,983 B2 | 10/2007 | Ireland et al. |
| 7,281,519 B2 | 10/2007 | Schroeder et al. |
| 7,282,029 B1 | 10/2007 | Poulsen |
| 7,285,293 B2 | 10/2007 | Castillo et al. |
| 7,287,289 B1 | 10/2007 | Hagopian |
| 7,287,485 B2 | 10/2007 | Petrakis |
| 7,288,085 B2 | 10/2007 | Olsen |
| 7,288,760 B2 | 10/2007 | Weitz |
| 7,289,142 B2 | 10/2007 | Silverbrook |
| 7,291,126 B2 | 11/2007 | Shekalim et al. |
| 7,291,132 B2 | 11/2007 | Deruntz et al. |
| 7,291,133 B1 | 11/2007 | Kindler et al. |
| 7,295,867 B2 | 11/2007 | Berner et al. |
| 7,297,151 B2 | 11/2007 | Boecker et al. |
| 7,302,295 B2 | 11/2007 | Stahmann et al. |
| 7,303,543 B1 | 12/2007 | Maule et al. |
| 7,303,549 B2 | 12/2007 | Flaherty et al. |
| 7,303,680 B2 | 12/2007 | Connell et al. |
| 7,304,033 B2 | 12/2007 | Larsen et al. |
| 7,305,975 B2 | 12/2007 | Reddy |
| 7,306,555 B2 | 12/2007 | Dolecek et al. |
| 7,306,578 B2 | 12/2007 | Gray et al. |
| 7,311,693 B2 | 12/2007 | Shekalim et al. |
| 7,316,700 B2 | 1/2008 | Alden et al. |
| 7,316,899 B2 | 1/2008 | McDevitt et al. |
| 7,318,892 B2 | 1/2008 | Connell et al. |
| 7,320,675 B2 | 1/2008 | Pastore et al. |
| 7,320,677 B2 | 1/2008 | Brouillette et al. |
| 7,322,321 B2 | 1/2008 | Robinson |
| 7,323,141 B2 | 1/2008 | Kirchhevel |
| 7,323,543 B2 | 1/2008 | Van Antwerp et al. |
| 7,324,012 B2 | 1/2008 | Mann et al. |
| 7,324,949 B2 | 1/2008 | Bristol et al. |
| 7,335,377 B2 | 2/2008 | Stern et al. |
| 7,338,464 B2 | 3/2008 | Blischak et al. |
| 7,341,577 B2 | 3/2008 | Gill |
| 7,341,581 B2 | 3/2008 | Mallett |
| 7,344,500 B2 | 3/2008 | Talbot et al. |
| 7,344,507 B2 | 3/2008 | Briggs et al. |
| 7,344,894 B2 | 3/2008 | Greenstein et al. |
| 7,347,201 B2 | 3/2008 | Djupesland |
| 7,347,836 B2 | 3/2008 | Peterson et al. |
| 7,347,854 B2 | 3/2008 | Shelton et al. |
| 7,348,176 B2 | 3/2008 | DiMilla et al. |
| 7,350,190 B2 | 3/2008 | Torres et al. |
| 7,351,239 B2 | 4/2008 | Gill |
| 7,351,340 B2 | 4/2008 | Connell et al. |
| 7,351,411 B2 | 4/2008 | Holash et al. |
| 7,351,695 B2 | 4/2008 | Almarssoo et al. |
| 7,354,420 B2 | 4/2008 | Steil et al. |
| 7,356,382 B2 | 4/2008 | Vanderveen |
| 7,357,794 B2 | 4/2008 | Makower et al. |
| 7,357,899 B2 | 4/2008 | Gaillard et al. |
| 7,358,091 B2 | 4/2008 | Phillips et al. |
| 7,361,155 B2 | 4/2008 | Sage, Jr. et al. |
| 7,362,971 B2 | 4/2008 | Silverbrook et al. |
| 7,363,072 B2 | 4/2008 | Movahed |
| 7,363,075 B2 | 4/2008 | Stern et al. |
| 7,364,566 B2 | 4/2008 | Elkins et al. |
| 7,364,568 B2 | 4/2008 | Angel et al. |
| 7,366,925 B2 | 4/2008 | Keely et al. |
| 7,334,556 B2 | 5/2008 | Wachigai et al. |
| 7,368,003 B2 | 5/2008 | Crapser et al. |
| 7,371,418 B2 | 5/2008 | Sheabar et al. |
| 7,373,083 B2 | 5/2008 | Silverbrook et al. |
| 7,373,690 B2 | 5/2008 | Sepke et al. |
| 7,373,826 B2 | 5/2008 | Weber et al. |
| 7,374,544 B2 | 5/2008 | Freeman et al. |
| 7,374,556 B2 | 5/2008 | Mallett |
| 7,377,706 B2 | 5/2008 | Silverbrook et al. |
| 7,377,907 B2 | 5/2008 | Shekalim et al. |
| 7,378,270 B2 | 5/2008 | Azarnia et al. |
| 7,378,443 B2 | 5/2008 | Berge |
| 7,380,447 B2 | 6/2008 | Rollinger et al. |
| 7,384,397 B2 | 6/2008 | Zhang et al. |
| 7,384,410 B2 | 6/2008 | Eggers et al. |
| 7,384,413 B2 | 6/2008 | Gross et al. |
| 7,384,912 B2 | 6/2008 | Stewart |
| 7,385,443 B1 | 6/2008 | Denison |
| 7,386,346 B2 | 6/2008 | Struble |
| 7,390,311 B2 | 6/2008 | Hildebrand et al. |
| 7,390,314 B2 | 6/2008 | Stutz, Jr. et al. |
| 7,390,458 B2 | 6/2008 | Burow et al. |
| 7,394,182 B2 | 7/2008 | Pelrine et al. |
| 7,396,353 B2 | 7/2008 | Lorenzen et al. |
| 7,399,277 B2 | 7/2008 | Saidara et al. |
| 7,399,304 B2 | 7/2008 | Gambale et al. |
| 7,399,401 B2 | 7/2008 | Rush |
| 7,399,772 B2 | 7/2008 | Phillips |
| 7,402,153 B2 | 7/2008 | Steil et al. |
| 7,402,154 B2 | 7/2008 | Holst et al. |
| 7,405,055 B2 | 7/2008 | Dunn et al. |

(56) References Cited

U.S. PATENT DOCUMENTS

| | | |
|---|---|---|
| 7,407,489 B2 | 8/2008 | Holst et al. |
| 7,407,490 B2 | 8/2008 | Bendsen et al. |
| 7,410,468 B2 | 8/2008 | Freeman et al. |
| 7,410,475 B2 | 8/2008 | Krensky et al. |
| 7,411,204 B2 | 8/2008 | Appleby et al. |
| 7,416,644 B2 | 8/2008 | Bonde |
| 7,421,316 B2 | 9/2008 | Gray et al. |
| 7,421,882 B2 | 9/2008 | Leddy et al. |
| 7,425,204 B2 | 9/2008 | Angel et al. |
| 7,426,408 B2 | 9/2008 | DeNuzzio et al. |
| 7,427,275 B2 | 9/2008 | Deruntz et al. |
| 7,429,255 B2 | 9/2008 | Thompson |
| 7,429,258 B2 | 9/2008 | Angel et al. |
| 7,429,269 B2 | 9/2008 | Schwammenthal et al. |
| 7,435,250 B2 | 10/2008 | Francischelli et al. |
| 7,435,717 B2 | 10/2008 | Bisgaier et al. |
| 7,440,806 B1 | 10/2008 | Whitehurst et al. |
| 7,442,682 B2 | 10/2008 | Kitaura et al. |
| 7,444,436 B2 | 10/2008 | Wille |
| RE40,570 E | 11/2008 | Carpentier et al. |
| 7,445,616 B2 | 11/2008 | Petrakis |
| 7,446,091 B2 | 11/2008 | Van Den Berghe |
| 7,449,333 B2 | 11/2008 | Rolland et al. |
| 7,452,301 B2 | 11/2008 | Yoshioka |
| 7,455,663 B2 | 11/2008 | Bikovsky |
| 7,455,835 B2 | 11/2008 | Cohen et al. |
| 7,459,305 B2 | 12/2008 | Levy |
| 7,460,152 B2 | 12/2008 | Silverbrook et al. |
| 7,460,350 B2 | 12/2008 | Talbot et al. |
| 7,463,934 B2 | 12/2008 | Tronnes et al. |
| 7,464,010 B2 | 12/2008 | Yang et al. |
| 7,464,580 B2 | 12/2008 | Zeng et al. |
| 7,464,704 B2 | 12/2008 | Braithwaite |
| 7,465,285 B2 | 12/2008 | Hutchinson et al. |
| 7,465,375 B2 | 12/2008 | Demers et al. |
| 7,467,027 B2 | 12/2008 | Ding et al. |
| 7,467,613 B2 | 12/2008 | Taylor, Sr. |
| 7,468,033 B2 | 12/2008 | Van Antwerp et al. |
| 7,469,383 B2 | 12/2008 | Busch |
| 7,469,697 B2 | 12/2008 | Lee et al. |
| 7,469,844 B2 | 12/2008 | Conway et al. |
| 7,470,246 B2 | 12/2008 | Mori et al. |
| 7,471,994 B2 | 12/2008 | Ford et al. |
| 7,473,239 B2 | 1/2009 | Wang et al. |
| 7,473,247 B2 | 1/2009 | Mikszta et al. |
| 7,474,968 B2 | 1/2009 | Ding et al. |
| 7,475,825 B2 | 1/2009 | Silverbrook et al. |
| 7,476,200 B2 | 1/2009 | Tal |
| 7,476,209 B2 | 1/2009 | Gara et al. |
| 7,479,123 B2 | 1/2009 | Briggs |
| 7,481,218 B2 | 1/2009 | Djupesland |
| 7,481,759 B2 | 1/2009 | Whitehurst et al. |
| 7,481,776 B2 | 1/2009 | Boecker et al. |
| 7,481,792 B2 | 1/2009 | Gonelli et al. |
| 7,483,050 B2 | 1/2009 | Silverbrook et al. |
| 7,483,743 B2 | 1/2009 | Mann et al. |
| 7,485,298 B2 | 2/2009 | Powell |
| 7,491,178 B2 | 2/2009 | Boecker et al. |
| 7,491,187 B2 | 2/2009 | Van Den Berghe et al. |
| 7,491,335 B2 | 2/2009 | Reddy et al. |
| 7,493,154 B2 | 2/2009 | Bonner et al. |
| 7,493,171 B1 | 2/2009 | Whitehurst et al. |
| 7,494,481 B2 | 2/2009 | Moberg et al. |
| 7,497,841 B2 | 3/2009 | Alchas |
| 7,498,563 B2 | 3/2009 | Mandro et al. |
| 7,500,959 B2 | 3/2009 | Munk |
| 7,503,903 B2 | 3/2009 | Carlisle et al. |
| 7,505,869 B2 | 3/2009 | Hartlaub |
| 7,507,220 B2 | 3/2009 | Childers et al. |
| 7,507,235 B2 | 3/2009 | Keogh et al. |
| 7,509,169 B2 | 3/2009 | Eigler et al. |
| 7,510,544 B2 | 3/2009 | Vilks et al. |
| 7,510,552 B2 | 3/2009 | Lebel et al. |
| 7,511,914 B2 | 3/2009 | Hiller et al. |
| 7,514,075 B2 | 4/2009 | Hedrick et al. |
| 7,514,401 B2 | 4/2009 | Franco |
| 7,515,060 B2 | 4/2009 | Blomquist |
| 7,517,332 B2 | 4/2009 | Tonelli et al. |
| 7,517,335 B2 | 4/2009 | Gravesen et al. |
| 7,517,440 B2 | 4/2009 | Anex et al. |
| 7,517,498 B2 | 4/2009 | Fredrick |
| 7,517,530 B2 | 4/2009 | Clark |
| 7,520,867 B2 | 4/2009 | Bowman et al. |
| 7,524,045 B2 | 4/2009 | Silverbrook et al. |
| 7,524,287 B2 | 4/2009 | Bharmi |
| 7,524,293 B2 | 4/2009 | Freeman et al. |
| 7,524,304 B2 | 4/2009 | Genosar |
| 7,530,968 B2 | 5/2009 | Gonnelli |
| 7,530,975 B2 | 5/2009 | Hunter |
| 7,534,221 B2 | 5/2009 | Pile-Spellman |
| 7,534,226 B2 | 5/2009 | Mernoe et al. |
| 7,536,983 B2 | 5/2009 | Layher et al. |
| 7,537,571 B2 | 5/2009 | Freeman et al. |
| 7,540,859 B2 | 6/2009 | Claude et al. |
| 7,540,880 B2 | 6/2009 | Nolting |
| 7,543,581 B2 | 6/2009 | Djupesland |
| 7,547,281 B2 | 6/2009 | Hayes et al. |
| 7,547,287 B2 | 6/2009 | Boecker et al. |
| 7,548,314 B2 | 6/2009 | Altobelli et al. |
| 7,551,202 B2 | 6/2009 | Silverbrook |
| 7,553,281 B2 | 6/2009 | Hellwig et al. |
| 7,553,291 B2 | 6/2009 | Duffy et al. |
| 7,553,813 B2 | 6/2009 | Unemori |
| 7,556,613 B2 | 7/2009 | Wittmann et al. |
| 7,556,841 B2 | 7/2009 | Kimball et al. |
| 7,558,629 B2 | 7/2009 | Keimel et al. |
| 7,559,223 B2 | 7/2009 | Chen et al. |
| 7,559,524 B2 | 7/2009 | Gray et al. |
| 7,563,232 B2 | 7/2009 | Freeman et al. |
| 7,563,253 B2 | 7/2009 | Tanner et al. |
| 7,563,255 B2 | 7/2009 | Adamis et al. |
| D598,109 S | 8/2009 | Collins et al. |
| 7,569,030 B2 | 8/2009 | Lebel et al. |
| 7,569,036 B2 | 8/2009 | Domkowski et al. |
| 7,569,050 B2 | 8/2009 | Moberg et al. |
| 7,571,635 B2 | 8/2009 | Lyon |
| 7,572,789 B2 | 8/2009 | Cowen et al. |
| 7,577,477 B2 | 9/2009 | Allen et al. |
| 7,582,063 B2 | 9/2009 | Wurster et al. |
| 7,582,099 B2 | 9/2009 | Freeman et al. |
| 7,583,190 B2 | 9/2009 | Reggiardo et al. |
| 7,584,846 B2 | 9/2009 | Senter |
| 7,588,046 B1 | 9/2009 | Erickson |
| 7,588,550 B2 | 9/2009 | Leonard et al. |
| 7,588,563 B2 | 9/2009 | Guala |
| 7,588,784 B2 | 9/2009 | Maday et al. |
| 7,589,059 B2 | 9/2009 | Wolff et al. |
| 7,590,443 B2 | 9/2009 | Bharmi |
| 7,591,801 B2 | 9/2009 | Brauker et al. |
| 7,594,889 B2 | 9/2009 | St. Ores et al. |
| 7,597,682 B2 | 10/2009 | Moberg |
| 7,598,031 B2 | 10/2009 | Liew |
| 7,602,310 B2 | 10/2009 | Mann et al. |
| 7,603,174 B2 | 10/2009 | DeRidder |
| 7,604,592 B2 | 10/2009 | Freeman et al. |
| 7,604,619 B2 | 10/2009 | Eich et al. |
| 7,605,710 B2 | 10/2009 | Crnkovich et al. |
| 7,606,274 B2 | 10/2009 | Mirov et al. |
| 7,606,615 B2 | 10/2009 | Makower et al. |
| 7,607,965 B1 | 10/2009 | Frazier |
| 7,608,060 B2 | 10/2009 | Gillespie, Jr. et al. |
| 7,608,640 B2 | 10/2009 | Messadek |
| 7,618,615 B2 | 10/2009 | Frey, II et al. |
| 7,615,046 B2 | 11/2009 | Shehata |
| 7,618,369 B2 | 11/2009 | Hayter et al. |
| 7,618,954 B2 | 11/2009 | Nicolau et al. |
| 7,621,893 B2 | 11/2009 | Moberg et al. |
| 7,624,409 B2 | 11/2009 | Whymark |
| 7,625,354 B2 | 12/2009 | Hochman |
| 7,625,358 B2 | 12/2009 | Mernoe |
| 7,625,369 B2 | 12/2009 | Abboud et al. |
| 7,628,590 B2 | 12/2009 | Jacobsen et al. |
| 7,628,772 B2 | 12/2009 | McConnell et al. |
| 7,628,782 B2 | 12/2009 | Adair et al. |

(56) References Cited

U.S. PATENT DOCUMENTS

| | | |
|---|---|---|
| 7,630,748 B2 | 12/2009 | Budiman |
| 7,630,773 B2 | 12/2009 | Seeberger et al. |
| 7,630,791 B2 | 12/2009 | Nguyen et al. |
| 7,632,228 B2 | 12/2009 | Brauker et al. |
| 7,632,247 B2 | 12/2009 | Adams |
| 7,632,248 B2 | 12/2009 | Delk et al. |
| 7,635,349 B2 | 12/2009 | Tribe et al. |
| 7,635,575 B2 | 12/2009 | Scherze et al. |
| 7,637,279 B2 | 12/2009 | Amley et al. |
| 7,637,931 B2 | 12/2009 | Heaton |
| 7,638,095 B2 | 12/2009 | Sabol |
| 7,641,649 B2 | 1/2010 | Moberg et al. |
| 7,642,232 B2 | 1/2010 | Green et al. |
| 7,644,203 B2 | 1/2010 | Ingles |
| 7,645,253 B2 | 1/2010 | Gura et al. |
| 7,645,264 B2 | 1/2010 | Marsh et al. |
| 7,647,107 B2 | 1/2010 | Warman et al. |
| 7,647,115 B2 | 1/2010 | Levin et al. |
| 7,647,237 B2 | 1/2010 | Malave et al. |
| 7,650,181 B2 | 1/2010 | Freeman et al. |
| 7,650,190 B2 | 1/2010 | Zhou et al. |
| 7,651,489 B2 | 1/2010 | Estes et al. |
| 7,651,868 B2 | 1/2010 | McDevitt et al. |
| 7,653,425 B2 | 1/2010 | Hayter et al. |
| 7,653,639 B2 | 1/2010 | Classen |
| 7,654,127 B2 | 2/2010 | Krulevitch et al. |
| 7,654,131 B2 | 2/2010 | Ascheman |
| 7,654,484 B2 | 2/2010 | Mogensen et al. |
| 7,654,976 B2 | 2/2010 | Peterson et al. |
| 7,654,982 B2 | 2/2010 | Carlisle et al. |
| 7,655,221 B2 | 2/2010 | Rasmussen et al. |
| 7,657,313 B2 | 2/2010 | Rom |
| 7,662,105 B2 | 2/2010 | Hatlestad |
| 7,662,140 B2 | 2/2010 | Heruth et al. |
| 7,662,558 B2 | 2/2010 | Liew |
| 7,668,731 B2 | 2/2010 | Martucci et al. |
| 7,674,243 B2 | 3/2010 | Dacquay et al. |
| 7,674,485 B2 | 3/2010 | Bhaskaran et al. |
| 7,676,263 B2 | 3/2010 | Harris et al. |
| 7,676,519 B2 | 3/2010 | McBride et al. |
| 7,678,071 B2 | 3/2010 | Lebel et al. |
| 7,678,084 B2 | 3/2010 | Judson et al. |
| 7,678,761 B2 | 3/2010 | Coleman |
| 7,678,762 B2 | 3/2010 | Green et al. |
| 7,678,763 B2 | 3/2010 | Green et al. |
| 7,678,772 B2 | 3/2010 | Jia et al. |
| 7,678,833 B2 | 3/2010 | Ott |
| 7,681,570 B2 | 3/2010 | Vedrine et al. |
| 7,682,338 B2 | 3/2010 | Griffin |
| 7,682,430 B2 | 3/2010 | Kraemer et al. |
| 7,682,563 B2 | 3/2010 | Carpenter et al. |
| 7,683,029 B2 | 3/2010 | Hindle et al. |
| 7,685,865 B2 | 3/2010 | Norenberg |
| 7,686,787 B2 | 3/2010 | Moberg et al. |
| 7,687,272 B1 | 3/2010 | Buchwald et al. |
| RE41,288 E | 4/2010 | Coolidge et al. |
| D613,411 S | 4/2010 | Collins et al. |
| 7,691,330 B1 | 4/2010 | Winkler et al. |
| 7,695,454 B2 | 4/2010 | Barron et al. |
| 7,695,627 B2 | 4/2010 | Bosch et al. |
| 7,697,967 B2 | 4/2010 | Stafford |
| 7,697,995 B2 | 4/2010 | Cross, Jr. et al. |
| 7,699,767 B2 | 4/2010 | Mueth et al. |
| 7,699,775 B2 | 4/2010 | Desai et al. |
| 7,699,808 B2 | 4/2010 | Marrs et al. |
| 7,699,833 B2 | 4/2010 | Moberg et al. |
| 7,704,226 B2 | 4/2010 | Mueller, Jr. et al. |
| 7,704,227 B2 | 4/2010 | Moberg et al. |
| 7,704,237 B2 | 4/2010 | Fisher et al. |
| 7,704,238 B2 | 4/2010 | Diller et al. |
| 7,708,717 B2 | 5/2010 | Estes et al. |
| 7,708,872 B2 | 5/2010 | Eidsned et al. |
| 7,708,915 B2 | 5/2010 | Castor |
| 7,713,238 B2 | 5/2010 | Mernoe |
| 7,713,240 B2 | 5/2010 | Istoc et al. |
| 7,713,262 B2 | 5/2010 | Adams et al. |
| 7,713,574 B2 | 5/2010 | Brister et al. |
| 7,714,757 B2 | 5/2010 | Denison et al. |
| 7,714,889 B2 | 5/2010 | Silverbrook |
| 7,715,917 B2 | 5/2010 | Chinchoy et al. |
| 7,716,964 B2 | 5/2010 | Kurtz et al. |
| 7,717,856 B2 | 5/2010 | Chen et al. |
| 7,717,871 B2 | 5/2010 | Odland |
| 7,717,903 B2 | 5/2010 | Estes et al. |
| 7,722,536 B2 | 5/2010 | Goodnow |
| 7,736,338 B2 | 5/2010 | Kavazov et al. |
| 7,726,955 B2 | 6/2010 | Ryser et al. |
| 7,727,148 B2 | 6/2010 | Talbot et al. |
| 7,727,181 B2 | 6/2010 | Rush |
| 7,734,323 B2 | 6/2010 | Blomquist et al. |
| 7,736,309 B2 | 6/2010 | Miller et al. |
| 7,736,344 B2 | 6/2010 | Moberg et al. |
| 7,737,581 B2 | 6/2010 | Spurlin et al. |
| 7,740,708 B2 | 6/2010 | Lofton et al. |
| 7,743,007 B2 | 6/2010 | Jung et al. |
| 7,744,554 B2 | 6/2010 | Howard |
| 7,744,589 B2 | 6/2010 | Mounce et al. |
| 7,749,528 B2 | 7/2010 | De Carvalho et al. |
| 7,751,907 B2 | 7/2010 | Blomquist et al. |
| 7,753,660 B2 | 7/2010 | Gray |
| 7,753,873 B2 | 7/2010 | Rush |
| 7,753,879 B2 | 7/2010 | Mernoe |
| 7,753,885 B2 | 7/2010 | Duchon et al. |
| 7,756,722 B2 | 7/2010 | Levine et al. |
| 7,758,547 B2 | 7/2010 | Tonelli |
| 7,758,568 B2 | 7/2010 | Olsen |
| 7,760,601 B2 | 7/2010 | Igi |
| 7,762,793 B2 | 7/2010 | Gray et al. |
| 7,766,301 B2 | 8/2010 | Gray et al. |
| 7,766,829 B2 | 8/2010 | Sloan et al. |
| 7,766,830 B2 | 8/2010 | Fox et al. |
| 7,766,831 B2 | 8/2010 | Essenpreis et al. |
| 7,766,863 B2 | 8/2010 | Gillespie, Jr. et al. |
| 7,766,873 B2 | 8/2010 | Moberg et al. |
| 7,768,386 B2 | 8/2010 | Hayter et al. |
| 7,768,408 B2 | 8/2010 | Reggiardo et al. |
| 7,771,385 B2 | 8/2010 | Eggers et al. |
| 7,771,386 B2 | 8/2010 | Eggers et al. |
| 7,771,414 B2 | 8/2010 | Trieu |
| 7,774,145 B2 | 8/2010 | Brauker et al. |
| 7,775,975 B2 | 8/2010 | Brister et al. |
| 7,776,006 B2 | 8/2010 | Childers et al. |
| 7,776,030 B2 | 8/2010 | Estes et al. |
| 7,776,031 B2 | 8/2010 | Hartlaub et al. |
| 7,778,680 B2 | 8/2010 | Goode, Jr. et al. |
| 7,779,183 B2 | 8/2010 | Koehler et al. |
| 7,780,981 B2 | 8/2010 | DiPierro et al. |
| 7,782,192 B2 | 8/2010 | Jeckelmann et al. |
| 7,785,288 B2 | 8/2010 | Mernoe et al. |
| 7,785,293 B2 | 8/2010 | Gray et al. |
| 7,785,313 B2 | 8/2010 | Mastrototaro |
| 7,788,369 B2 | 8/2010 | McAllen et al. |
| 7,789,849 B2 | 9/2010 | Busby et al. |
| 7,789,857 B2 | 9/2010 | Moberg et al. |
| 7,790,103 B2 | 9/2010 | Shah et al. |
| 7,794,426 B2 | 9/2010 | Briones et al. |
| 7,794,427 B2 | 9/2010 | Estes et al. |
| 7,794,428 B2 | 9/2010 | Estes et al. |
| 7,794,434 B2 | 9/2010 | Mounce et al. |
| 7,797,028 B2 | 9/2010 | Goode, Jr. et al. |
| 7,797,649 B1 | 9/2010 | Etawil et al. |
| 7,801,582 B2 | 9/2010 | Peyser |
| 7,806,853 B2 | 10/2010 | Wittmann et al. |
| 7,806,854 B2 | 10/2010 | Damiano et al. |
| 7,806,867 B2 | 10/2010 | Willis et al. |
| 7,806,868 B2 | 10/2010 | De Polo et al. |
| 7,806,886 B2 | 10/2010 | Kanderian, Jr. et al. |
| 7,811,231 B2 | 10/2010 | Jin et al. |
| 7,811,246 B2 | 10/2010 | Koops |
| 7,811,262 B2 | 10/2010 | Moberg et al. |
| 7,811,279 B2 | 10/2010 | John |
| 7,815,595 B2 | 10/2010 | Busby et al. |
| 7,815,602 B2 | 10/2010 | Mann et al. |
| 7,815,609 B2 | 10/2010 | Hines et al. |

(56) References Cited

U.S. PATENT DOCUMENTS

| | | |
|---|---|---|
| 7,815,622 B2 | 10/2010 | Istoc |
| 7,819,843 B2 | 10/2010 | Mann et al. |
| 7,822,455 B2 | 10/2010 | Hoss et al. |
| RE41,956 E | 11/2010 | Klitgaard et al. |
| 7,826,382 B2 | 11/2010 | Sicurello et al. |
| 7,826,879 B2 | 11/2010 | Hoss et al. |
| 7,828,528 B2 | 11/2010 | Estes et al. |
| 7,828,747 B2 | 11/2010 | Heske et al. |
| 7,828,764 B2 | 11/2010 | Moberg et al. |
| 7,828,771 B2 | 11/2010 | Chiang et al. |
| 7,831,310 B2 | 11/2010 | Lebel et al. |
| 7,833,196 B2 | 11/2010 | Estes et al. |
| 7,835,927 B2 | 11/2010 | Schlotterbeck et al. |
| 7,837,647 B2 | 11/2010 | Estes et al. |
| 7,837,648 B2 | 11/2010 | Blair et al. |
| 7,837,651 B2 | 11/2010 | Bishop et al. |
| 7,849,872 B2 | 12/2010 | Phillips et al. |
| 7,850,641 B2 | 12/2010 | Lebel et al. |
| 7,850,658 B2 | 12/2010 | Faust et al. |
| 7,850,674 B2 | 12/2010 | Goodnow et al. |
| 7,851,509 B2 | 12/2010 | Miller et al. |
| 7,857,756 B2 | 12/2010 | Warren et al. |
| 7,857,791 B2 | 12/2010 | Jacobs et al. |
| 7,860,544 B2 | 12/2010 | Say et al. |
| 7,860,583 B2 | 12/2010 | Condurso et al. |
| 7,867,189 B2 | 1/2011 | Childers et al. |
| 7,869,853 B1 | 1/2011 | Say et al. |
| 7,874,718 B2 | 1/2011 | Demers et al. |
| 7,875,022 B2 | 1/2011 | Wenger et al. |
| 7,877,489 B2 | 1/2011 | Salesky et al. |
| 7,877,703 B1 | 1/2011 | Fleming |
| 7,879,026 B2 | 2/2011 | Estes et al. |
| 7,881,883 B2 | 2/2011 | Remde |
| 7,882,611 B2 | 2/2011 | Shah et al. |
| 7,883,464 B2 | 2/2011 | Stafford |
| 7,884,729 B2 | 2/2011 | Reggiardo et al. |
| 7,885,699 B2 | 2/2011 | Say et al. |
| 7,887,505 B2 | 2/2011 | Flaherty |
| 7,887,511 B2 | 2/2011 | Mernoe et al. |
| 7,887,512 B2 | 2/2011 | Estes et al. |
| 7,890,295 B2 | 2/2011 | Shin et al. |
| 7,892,199 B2 | 2/2011 | Mhatre et al. |
| 7,892,206 B2 | 2/2011 | Moberg et al. |
| 7,896,842 B2 | 3/2011 | Palmroos et al. |
| 7,901,394 B2 | 3/2011 | Ireland et al. |
| 7,905,710 B2 | 3/2011 | Wang et al. |
| 7,905,859 B2 | 3/2011 | Bynum et al. |
| 7,905,866 B2 | 3/2011 | Haider et al. |
| 7,905,868 B2 | 3/2011 | Moberg et al. |
| 7,912,674 B2 | 3/2011 | Redl et al. |
| 7,914,499 B2 | 3/2011 | Gonneli et al. |
| 7,914,500 B2 | 3/2011 | Gafner-Geiser et al. |
| 7,914,742 B2 | 3/2011 | Arbogast et al. |
| 7,917,186 B2 | 3/2011 | Kamath et al. |
| 7,918,825 B2 | 4/2011 | O'connor et al. |
| 7,919,063 B2 | 4/2011 | Sarofim |
| 7,920,907 B2 | 4/2011 | Mcgarraugh et al. |
| 7,922,096 B2 | 4/2011 | Eilersen |
| 7,922,458 B2 | 4/2011 | Rush et al. |
| 7,922,462 B2 | 4/2011 | Preuthun et al. |
| 7,928,850 B2 | 4/2011 | Hayter et al. |
| 7,931,592 B2 | 4/2011 | Currie et al. |
| 7,931,613 B2 | 4/2011 | Haueter et al. |
| 7,931,642 B2 | 4/2011 | Tonnies |
| 7,931,864 B2 | 4/2011 | Kloepfer et al. |
| 7,933,639 B2 | 4/2011 | Goode et al. |
| 7,933,780 B2 | 4/2011 | De La Huerga |
| 7,935,074 B2 | 5/2011 | Plahey et al. |
| 7,935,076 B2 | 5/2011 | Estes et al. |
| 7,935,079 B2 | 5/2011 | Ludin et al. |
| 7,935,104 B2 | 5/2011 | Yodfat et al. |
| 7,935,105 B2 | 5/2011 | Miller et al. |
| 7,935,499 B2 | 5/2011 | Dunn et al. |
| 7,937,163 B2 | 5/2011 | Sekiguchi |
| 7,938,792 B2 | 5/2011 | Roger et al. |
| 7,938,797 B2 | 5/2011 | Estes et al. |
| 7,938,802 B2 | 5/2011 | Bicknell et al. |
| 7,938,803 B2 | 5/2011 | Mernoe et al. |
| 7,941,200 B2 | 5/2011 | Weinert et al. |
| 7,942,069 B2 | 5/2011 | Peterson |
| 7,942,844 B2 | 5/2011 | Moberg et al. |
| 7,944,366 B2 | 5/2011 | Krulevitch et al. |
| 7,945,452 B2 | 5/2011 | Fathallah et al. |
| 7,946,985 B2 | 5/2011 | Mastrototaro et al. |
| 7,948,370 B2 | 5/2011 | Reggiardo et al. |
| 7,951,112 B2 | 5/2011 | Patzer |
| 7,951,114 B2 | 5/2011 | Rush et al. |
| 7,951,122 B2 | 5/2011 | Shekalim |
| 7,955,261 B2 | 6/2011 | Goode et al. |
| 7,955,305 B2 | 6/2011 | Moberg et al. |
| 7,955,319 B2 | 6/2011 | Miesel |
| 7,955,843 B2 | 6/2011 | Barringer, Jr. |
| 7,957,984 B1 | 6/2011 | Vallone |
| 7,959,569 B2 | 6/2011 | Goode et al. |
| 7,959,598 B2 | 6/2011 | Estes et al. |
| 7,959,608 B2 | 6/2011 | Nash et al. |
| 7,959,715 B2 | 6/2011 | Kavazov et al. |
| 7,959,938 B2 | 6/2011 | Rohloff et al. |
| 7,963,945 B2 | 6/2011 | Miller et al. |
| 7,963,946 B2 | 6/2011 | Moubayed et al. |
| 7,963,954 B2 | 6/2011 | Kavazov et al. |
| 7,964,555 B2 | 6/2011 | Zhou |
| 7,967,010 B2 | 6/2011 | Vedrine et al. |
| 7,967,022 B2 | 6/2011 | Grant et al. |
| 7,967,740 B2 | 6/2011 | Mertens et al. |
| 7,967,752 B2 | 6/2011 | Oevirk et al. |
| 7,967,773 B2 | 6/2011 | Amnorn et al. |
| 7,967,785 B2 | 6/2011 | Morgan et al. |
| 7,967,806 B2 | 6/2011 | Jasperson et al. |
| 7,967,810 B2 | 6/2011 | Freedman et al. |
| 7,967,812 B2 | 6/2011 | Jasperson et al. |
| 7,970,620 B2 | 6/2011 | Brown |
| 7,955,295 B2 | 7/2011 | Lee et al. |
| 7,972,286 B2 | 7/2011 | Prausnitz et al. |
| 7,972,296 B2 | 7/2011 | Braig et al. |
| 7,972,302 B2 | 7/2011 | Caizza et al. |
| 7,972,303 B2 | 7/2011 | Caizza et al. |
| 7,972,304 B2 | 7/2011 | Caizza et al. |
| 7,973,667 B2 | 7/2011 | Crnkovich et al. |
| 7,976,478 B2 | 7/2011 | Fujiwara et al. |
| 7,976,492 B2 | 7/2011 | Brauker et al. |
| 7,976,493 B2 | 7/2011 | Carter et al. |
| 7,976,499 B2 | 7/2011 | Grunhut et al. |
| 7,976,500 B2 | 7/2011 | Adams et al. |
| 7,976,505 B2 | 7/2011 | Hines et al. |
| 7,976,508 B2 | 7/2011 | Hoag |
| 7,976,514 B2 | 7/2011 | Abry et al. |
| 7,976,530 B2 | 7/2011 | Johnson et al. |
| 7,976,778 B2 | 7/2011 | Drucker et al. |
| 7,976,865 B2 | 7/2011 | Kawamura et al. |
| 7,976,870 B2 | 7/2011 | Berner et al. |
| 7,979,104 B2 | 7/2011 | Kamath et al. |
| 7,979,136 B2 | 7/2011 | Young et al. |
| 7,981,034 B2 | 7/2011 | Jennewine et al. |
| 7,981,042 B2 | 7/2011 | Stahmann et al. |
| 7,981,076 B2 | 7/2011 | Sullivan et al. |
| 7,981,081 B2 | 7/2011 | Marsh et al. |
| 7,981,084 B2 | 7/2011 | Estes et al. |
| 7,981,090 B2 | 7/2011 | Plishka et al. |
| 7,981,102 B2 | 7/2011 | Patel et al. |
| 7,981,105 B2 | 7/2011 | Adair et al. |
| 7,981,107 B2 | 7/2011 | Olsen |
| 7,983,745 B2 | 7/2011 | Hatlestad et al. |
| 7,985,057 B2 | 7/2011 | Haar |
| 7,985,330 B2 | 7/2011 | Wang et al. |
| 7,986,986 B2 | 7/2011 | Goode et al. |
| 7,988,630 B1 | 8/2011 | Osorio et al. |
| 7,988,660 B2 | 8/2011 | Byland et al. |
| 7,988,663 B2 | 8/2011 | Schiller et al. |
| 7,988,674 B2 | 8/2011 | Adams et al. |
| 7,988,687 B2 | 8/2011 | Friedli |
| 7,988,849 B2 | 8/2011 | Biewer et al. |
| 7,988,850 B2 | 8/2011 | Roncadi et al. |
| 7,990,251 B1 | 8/2011 | Ford, Jr. |

(56) References Cited

U.S. PATENT DOCUMENTS

| | | |
|---|---|---|
| 7,993,108 B2 | 8/2011 | Rush et al. |
| 7,993,140 B2 | 8/2011 | Sakezles |
| 7,993,300 B2 | 8/2011 | Nyholm et al. |
| 7,993,306 B2 | 8/2011 | Marrs et al. |
| 7,996,158 B2 | 8/2011 | Hayter et al. |
| 7,998,110 B2 | 8/2011 | Leung et al. |
| 7,998,111 B2 | 8/2011 | Moberg et al. |
| 7,998,117 B2 | 8/2011 | Gross et al. |
| 7,999,674 B2 | 8/2011 | Kamen |
| 7,999,927 B2 | 8/2011 | Braig et al. |
| 8,000,763 B2 | 8/2011 | Mazza et al. |
| 8,002,700 B2 | 8/2011 | Ferek-Petric et al. |
| 8,002,747 B2 | 8/2011 | Lord et al. |
| 8,003,630 B2 | 8/2011 | Zagon et al. |
| 8,005,524 B2 | 8/2011 | Brauker et al. |
| 8,005,540 B2 | 8/2011 | Zhang et al. |
| 8,005,688 B2 | 8/2011 | Coffman et al. |
| 8,007,460 B2 | 8/2011 | Gelfand et al. |
| 8,007,487 B2 | 8/2011 | Patrick et al. |
| 8,007,724 B2 | 8/2011 | Guzman |
| RE42,682 E | 9/2011 | Barreras, Sr. et al. |
| 8,011,039 B2 | 9/2011 | Stryker et al. |
| 8,012,104 B2 | 9/2011 | Escutia et al. |
| 8,012,114 B2 | 9/2011 | Daniel et al. |
| 8,012,119 B2 | 9/2011 | Estes et al. |
| 8,012,121 B2 | 9/2011 | Goodson, IV et al. |
| 8,012,132 B2 | 9/2011 | Lum et al. |
| 8,014,857 B2 | 9/2011 | Doerr |
| 8,016,740 B2 | 9/2011 | Connors et al. |
| 8,016,772 B2 | 9/2011 | Keske et al. |
| 8,016,783 B2 | 9/2011 | Pastore et al. |
| 8,016,789 B2 | 9/2011 | Grant et al. |
| 8,016,812 B2 | 9/2011 | Koh |
| 8,016,859 B2 | 9/2011 | Donofrio et al. |
| 8,019,721 B2 | 9/2011 | Young et al. |
| 8,020,564 B2 | 9/2011 | Batch |
| 8,021,299 B2 | 9/2011 | Miesel et al. |
| 8,021,334 B2 | 9/2011 | Shekalim |
| 8,021,680 B2 | 9/2011 | Anderson et al. |
| 8,022,042 B2 | 9/2011 | Ko |
| 8,022,366 B2 | 9/2011 | Hartley |
| 8,025,634 B1 | 9/2011 | Moubayed et al. |
| 8,026,209 B2 | 9/2011 | Gaillard et al. |
| 8,026,215 B2 | 9/2011 | Unemori |
| 8,026,227 B2 | 9/2011 | Hausheer |
| 8,027,740 B2 | 9/2011 | Altman et al. |
| 8,029,245 B2 | 10/2011 | Rush et al. |
| 8,029,250 B2 | 10/2011 | Rush et al. |
| 8,029,454 B2 | 10/2011 | Kelly et al. |
| 8,029,459 B2 | 10/2011 | Rush et al. |
| 8,029,460 B2 | 10/2011 | Rush et al. |
| 8,030,058 B1 | 10/2011 | Benedict et al. |
| 8,030,802 B2 | 10/2011 | Lindegger et al. |
| 8,030,891 B2 | 10/2011 | Welsch et al. |
| 8,032,226 B2 | 10/2011 | Miller et al. |
| 8,034,015 B2 | 10/2011 | Braig et al. |
| 8,034,019 B2 | 10/2011 | Nair et al. |
| 8,034,026 B2 | 10/2011 | Grant et al. |
| 8,034,793 B2 | 10/2011 | Heidenreich et al. |
| 8,038,650 B2 | 10/2011 | Shekalim |
| 8,038,709 B2 | 10/2011 | Palasis et al. |
| 8,043,074 B2 | 10/2011 | Tada |
| 8,043,258 B2 | 10/2011 | Ostroot |
| 8,043,277 B2 | 10/2011 | Junker |
| 8,043,281 B2 | 10/2011 | Heruth et al. |
| 8,043,744 B2 | 10/2011 | Traulsen et al. |
| 8,046,043 B2 | 10/2011 | Asano et al. |
| RE42,958 E | 11/2011 | Loeb et al. |
| 8,047,202 B2 | 11/2011 | Djupesland |
| 8,047,811 B2 | 11/2011 | Rush et al. |
| 8,047,812 B2 | 11/2011 | Rush et al. |
| 8,047,819 B2 | 11/2011 | Lawrence et al. |
| 8,048,041 B2 | 11/2011 | Cefai et al. |
| 8,048,619 B2 | 11/2011 | Chow |
| 8,049,059 B2 | 11/2011 | Bleyer et al. |
| 8,050,729 B2 | 11/2011 | Shekalim |
| 8,052,614 B2 | 11/2011 | Heske et al. |
| 8,053,429 B2 | 11/2011 | Cumming et al. |
| 8,056,582 B2 | 11/2011 | DiPerna |
| 8,057,156 B2 | 11/2011 | List |
| 8,057,426 B2 | 11/2011 | Nayak et al. |
| 8,057,679 B2 | 11/2011 | Yu et al. |
| 8,060,185 B2 | 11/2011 | Hunter et al. |
| 8,060,209 B2 | 11/2011 | Jaax et al. |
| 8,062,249 B2 | 11/2011 | Wilinska et al. |
| 8,062,256 B2 | 11/2011 | Carter et al. |
| 8,062,257 B2 | 11/2011 | Moberg et al. |
| 8,062,264 B2 | 11/2011 | Godfrey et al. |
| 8,065,096 B2 | 11/2011 | Moberg et al. |
| 8,065,161 B2 | 11/2011 | Howard et al. |
| 8,066,197 B2 | 11/2011 | Sheppard |
| 8,066,198 B2 | 11/2011 | Palanchon et al. |
| 8,066,629 B2 | 11/2011 | Dlugos |
| 8,066,665 B2 | 11/2011 | Rush et al. |
| 8,066,668 B2 | 11/2011 | Wayman et al. |
| 8,066,671 B2 | 11/2011 | Busby et al. |
| 8,066,680 B2 | 11/2011 | Alchas et al. |
| 8,066,688 B2 | 11/2011 | Zinger et al. |
| 8,066,940 B2 | 11/2011 | Denkewicz, Jr. et al. |
| 8,067,031 B2 | 11/2011 | Daniloff et al. |
| 8,067,173 B2 | 11/2011 | Liew |
| 8,070,723 B2 | 12/2011 | Bazargan et al. |
| 8,070,726 B2 | 12/2011 | Gonnelli et al. |
| 8,070,741 B2 | 12/2011 | Barrelle et al. |
| 8,070,742 B2 | 12/2011 | Woo |
| 8,071,075 B2 | 12/2011 | Reed et al. |
| 8,071,722 B2 | 12/2011 | Kaplan et al. |
| 8,073,543 B2 | 12/2011 | Pyles |
| 8,073,549 B2 | 12/2011 | Chen |
| 8,075,503 B2 | 12/2011 | Jaeb |
| 8,075,522 B2 | 12/2011 | Larsen et al. |
| 8,075,527 B2 | 12/2011 | Rush et al. |
| 8,075,919 B2 | 12/2011 | Brown et al. |
| 8,078,983 B2 | 12/2011 | Davis et al. |
| 8,079,983 B2 | 12/2011 | Rush et al. |
| 8,079,984 B2 | 12/2011 | Rush et al. |
| 8,080,002 B2 | 12/2011 | Stergiopulos et al. |
| 8,081,069 B2 | 12/2011 | Haueter et al. |
| 8,082,041 B1 | 12/2011 | Radziemski |
| 8,083,209 B2 | 12/2011 | Kozdras et al. |
| 8,083,711 B2 | 12/2011 | Enggaard |
| 8,083,718 B2 | 12/2011 | Rush et al. |
| 8,083,720 B2 | 12/2011 | Solar et al. |
| 8,083,722 B2 | 12/2011 | McKay |
| 8,083,730 B2 | 12/2011 | Miesel |
| 8,088,098 B2 | 1/2012 | Yodfat et al. |
| 8,088,789 B2 | 1/2012 | Yan et al. |
| 8,089,787 B2 | 1/2012 | Melse |
| 8,090,430 B2 | 1/2012 | Makower et al. |
| 8,090,435 B2 | 1/2012 | Gill et al. |
| 8,092,428 B2 | 1/2012 | Ramey et al. |
| 8,093,038 B2 | 1/2012 | Hatziavramidis |
| 8,093,212 B2 | 1/2012 | Gardner et al. |
| 8,093,214 B2 | 1/2012 | Crockford |
| 8,093,781 B2 | 1/2012 | Chiang et al. |
| 8,094,009 B2 | 1/2012 | Allen et al. |
| 8,096,329 B2 | 1/2012 | Thuot et al. |
| 8,096,487 B2 | 1/2012 | Hornsby |
| 8,096,972 B2 | 1/2012 | Varner et al. |
| 8,096,983 B2 | 1/2012 | Uchino et al. |
| 8,099,800 B2 | 1/2012 | Sawalski et al. |
| 8,100,842 B2 | 1/2012 | Rousso |
| 8,100,852 B2 | 1/2012 | Moberg et al. |
| 8,100,871 B2 | 1/2012 | Haase |
| 8,101,358 B2 | 1/2012 | Liew |
| 8,101,402 B2 | 1/2012 | Holmes |
| 8,101,727 B2 | 1/2012 | Stover et al. |
| 8,105,265 B2 | 1/2012 | Demers et al. |
| 8,105,268 B2 | 1/2012 | Lebel et al. |
| 8,105,269 B2 | 1/2012 | Zhou |
| 8,105,279 B2 | 1/2012 | Mernoe et al. |
| 8,105,280 B2 | 1/2012 | Iddan et al. |
| 8,105,351 B2 | 1/2012 | Lehman et al. |
| 8,106,534 B2 | 1/2012 | Spurlin et al. |

(56) References Cited

U.S. PATENT DOCUMENTS

| | | |
|---|---|---|
| 8,108,051 B2 | 1/2012 | Cross, Jr. et al. |
| 8,109,893 B2 | 2/2012 | Lande |
| 8,109,906 B2 | 2/2012 | Smisson et al. |
| 8,109,912 B2 | 2/2012 | Alferness et al. |
| 8,109,921 B2 | 2/2012 | Estes et al. |
| 8,110,224 B2 | 2/2012 | Ausborn et al. |
| 8,110,358 B2 | 2/2012 | Liew |
| 8,110,555 B2 | 2/2012 | Jia et al. |
| 8,112,287 B1 | 2/2012 | Paul et al. |
| 8,112,288 B1 | 2/2012 | Paul et al. |
| 8,114,023 B2 | 2/2012 | Ward et al. |
| 8,114,056 B2 | 2/2012 | Niklaus et al. |
| 8,114,064 B2 | 2/2012 | Alferness et al. |
| 8,114,350 B1 | 2/2012 | Silver et al. |
| 8,114,430 B2 | 2/2012 | Rohloff et al. |
| 8,114,597 B2 | 2/2012 | Liew |
| 8,115,600 B2 | 2/2012 | Stevenson et al. |
| 8,116,862 B2 | 2/2012 | Stevenson et al. |
| 8,118,571 B2 | 2/2012 | Krisher |
| 8,118,782 B2 | 2/2012 | Remde |
| 8,119,159 B2 | 2/2012 | Cumming et al. |
| 8,119,593 B2 | 2/2012 | Richardson et al. |
| 8,121,857 B2 | 2/2012 | Galasso et al. |
| 8,123,717 B2 | 2/2012 | Weinert et al. |
| 8,123,720 B2 | 2/2012 | Solomon |
| 8,124,689 B2 | 2/2012 | Loubert et al. |
| 8,126,728 B2 | 2/2012 | Dicks et al. |
| 8,126,729 B2 | 2/2012 | Dicks et al. |
| 8,126,730 B2 | 2/2012 | Dicks et al. |
| 8,126,732 B2 | 2/2012 | Dicks et al. |
| 8,126,733 B2 | 2/2012 | Dicks et al. |
| 8,126,734 B2 | 2/2012 | Dicks et al. |
| 8,127,046 B2 | 2/2012 | Grant et al. |
| 8,128,589 B2 | 3/2012 | Freeman et al. |
| 8,128,597 B2 | 3/2012 | Cross et al. |
| 8,128,946 B2 | 3/2012 | Kawamura et al. |
| 8,129,429 B2 | 3/2012 | Sporn et al. |
| 8,130,095 B2 | 3/2012 | Allen et al. |
| 8,147,451 B2 | 4/2012 | Brockman |
| 8,147,511 B2 | 4/2012 | Perry |
| 8,149,131 B2 | 4/2012 | Blomquist |
| 8,152,764 B2 | 4/2012 | Istoc et al. |
| 8,156,070 B2 | 4/2012 | Buck |
| 8,167,832 B2 | 5/2012 | Bowman |
| 8,172,082 B2 | 5/2012 | Edwards |
| 8,172,798 B2 | 5/2012 | Hungerford |
| 8,177,739 B2 | 5/2012 | Cartledge |
| 8,182,447 B2 | 5/2012 | Moberg et al. |
| 8,182,461 B2 | 5/2012 | Pope et al. |
| 8,182,462 B2 | 5/2012 | Istoc et al. |
| 8,187,228 B2 | 5/2012 | Bikovsky |
| 8,192,394 B2 | 6/2012 | Estes et al. |
| 8,202,267 B2 | 6/2012 | Field et al. |
| 8,206,296 B2 | 6/2012 | Jennewine |
| 8,206,350 B2 | 6/2012 | Mann et al. |
| 8,206,378 B1 | 6/2012 | Kalpin et al. |
| 8,211,062 B2 | 7/2012 | Estes et al. |
| 8,211,093 B2 | 7/2012 | Miller et al. |
| 8,211,364 B2 | 7/2012 | Drucker et al. |
| 8,223,028 B2 | 7/2012 | Mandro et al. |
| 8,231,562 B2 | 7/2012 | Buck et al. |
| 8,231,572 B2 | 7/2012 | Carter et al. |
| 8,231,578 B2 | 7/2012 | Fathallah et al. |
| 8,234,126 B1 | 7/2012 | Estes |
| 8,234,128 B2 | 7/2012 | Martucci et al. |
| 8,237,715 B2 | 8/2012 | Buck et al. |
| 8,257,652 B2 | 9/2012 | Drucker et al. |
| 8,257,653 B2 | 9/2012 | Drucker et al. |
| 8,267,893 B2 | 9/2012 | Moberg et al. |
| 8,282,601 B2 | 10/2012 | Mernoe et al. |
| 8,285,328 B2 | 10/2012 | Caffey et al. |
| 8,287,454 B2 | 10/2012 | Wolpert et al. |
| 8,287,495 B2 | 10/2012 | Michaud et al. |
| 8,287,514 B2 | 10/2012 | Miller et al. |
| 8,287,521 B2 | 10/2012 | Kriesel et al. |
| 8,292,876 B2 | 10/2012 | Kriesel et al. |
| 8,298,183 B2 | 10/2012 | Menot et al. |
| 8,298,184 B2 | 10/2012 | Diperna et al. |
| 8,317,752 B2 | 11/2012 | Cozmi et al. |
| 8,323,188 B2 | 12/2012 | Tran |
| 8,328,754 B2 | 12/2012 | Estes et al. |
| 8,328,793 B2 | 12/2012 | Birkenbach et al. |
| 8,344,847 B2 | 1/2013 | Moberg et al. |
| 8,348,886 B2 | 1/2013 | Kanderian et al. |
| 8,348,923 B2 | 1/2013 | Kanderian et al. |
| 8,361,030 B2 | 1/2013 | Carter |
| 8,372,040 B2 | 2/2013 | Huang et al. |
| 8,376,943 B2 | 2/2013 | Kovach et al. |
| 8,380,536 B2 | 2/2013 | Howard et al. |
| 8,395,581 B2 | 3/2013 | Graskov |
| 8,398,592 B2 | 3/2013 | Leibner-Druska |
| 8,407,063 B2 | 3/2013 | Brown |
| 8,408,421 B2 | 4/2013 | DiPerna |
| 8,414,532 B2 | 4/2013 | Brandt et al. |
| 8,414,557 B2 | 4/2013 | Istoc |
| 8,414,563 B2 | 4/2013 | Kamen |
| 8,435,206 B2 | 5/2013 | Evans et al. |
| 8,444,592 B2 | 5/2013 | Williams et al. |
| 8,448,824 B2 | 5/2013 | DiPerna |
| 8,449,524 B2 | 5/2013 | Braig et al. |
| 8,454,562 B1 | 6/2013 | Sims |
| 8,454,575 B2 | 6/2013 | Estes et al. |
| 8,524,154 B2 | 9/2013 | Shekalim et al. |
| 8,573,027 B2 | 11/2013 | Rosinko et al. |
| 8,608,699 B2 | 12/2013 | Blomquist |
| 8,641,671 B2 | 2/2014 | Michaud et al. |
| 8,694,331 B2 | 4/2014 | Olsen |
| 8,758,323 B2 | 6/2014 | Michaud et al. |
| 8,926,561 B2 | 1/2015 | Verhoef et al. |
| 8,986,253 B2 | 3/2015 | DiPerna |
| 9,173,998 B2 | 11/2015 | Rosinko et al. |
| 9,180,243 B2 | 11/2015 | Michaud |
| 9,194,383 B2 | 11/2015 | Knobel |
| 9,211,377 B2 | 12/2015 | Diperna et al. |
| 9,421,329 B2 | 8/2016 | Kruse |
| 2001/0000282 A1 | 4/2001 | Poleshuk et al. |
| 2001/0027791 A1 | 10/2001 | Wallace et al. |
| 2001/0041869 A1 | 11/2001 | James, III et al. |
| 2002/0004015 A1 | 1/2002 | Carlisle et al. |
| 2002/0018720 A1 | 2/2002 | Carlisle et al. |
| 2002/0019714 A1 | 2/2002 | Carlisle et al. |
| 2002/0029776 A1 | 3/2002 | Blomquist |
| 2002/0040208 A1 | 4/2002 | Flaherty et al. |
| 2002/0045265 A1 | 4/2002 | Bergh et al. |
| 2002/0048536 A1 | 4/2002 | Bergh et al. |
| 2002/0055787 A1 | 5/2002 | Lennox et al. |
| 2002/0059959 A1 | 5/2002 | Qatu et al. |
| 2002/0065484 A1 | 5/2002 | Douglas et al. |
| 2002/0072733 A1 | 6/2002 | Flaherty |
| 2002/0076679 A1 | 6/2002 | Aman |
| 2002/0117214 A1 | 8/2002 | Tucker et al. |
| 2002/0120234 A1 | 8/2002 | Kong |
| 2002/0154571 A1 | 10/2002 | Cefai et al. |
| 2002/0173769 A1 | 11/2002 | Gray et al. |
| 2003/0014016 A1 | 1/2003 | Purdy |
| 2003/0032930 A1 | 2/2003 | Branch et al. |
| 2003/0036725 A1 | 2/2003 | Lavi et al. |
| 2003/0055380 A1 | 3/2003 | Flaherty |
| 2003/0060765 A1 | 3/2003 | Campbell et al. |
| 2003/0183289 A1 | 3/2003 | Seuret et al. |
| 2003/0065308 A1 | 4/2003 | Lebel et al. |
| 2003/0078547 A1 | 4/2003 | Shekalim |
| 2003/0093105 A1 | 5/2003 | Huffmaster |
| 2003/0097082 A1 | 5/2003 | Purdy et al. |
| 2003/0100863 A1 | 5/2003 | Shekalim |
| 2003/0109836 A1 | 6/2003 | Shekalim |
| 2003/0130577 A1 | 7/2003 | Purdy et al. |
| 2003/0161744 A1 | 8/2003 | Vilks et al. |
| 2003/0163088 A1 | 8/2003 | Blomquist |
| 2003/0163789 A1 | 8/2003 | Blomquist |
| 2003/0199378 A1 | 10/2003 | Saviano |
| 2003/0212364 A1 | 11/2003 | Mann et al. |
| 2003/0216683 A1 | 11/2003 | Shekalim |
| 2004/0010207 A1 | 1/2004 | Flaherty et al. |

(56) References Cited

U.S. PATENT DOCUMENTS

| | | |
|---|---|---|
| 2004/0019325 A1 | 1/2004 | Shekalim |
| 2004/0051368 A1 | 3/2004 | Caputo |
| 2004/0068230 A1 | 4/2004 | Estes et al. |
| 2004/0073095 A1 | 4/2004 | Causey, III et al. |
| 2004/0073161 A1 | 4/2004 | Tachibana |
| 2004/0074785 A1 | 4/2004 | Holker et al. |
| 2004/0078028 A1 | 4/2004 | Flaherty et al. |
| 2004/0092865 A1 | 5/2004 | Flaherty et al. |
| 2004/0116866 A1 | 6/2004 | Gorman et al. |
| 2004/0116905 A1 | 6/2004 | Pederson et al. |
| 2004/0122353 A1 | 6/2004 | Shahmirian et al. |
| 2004/0133166 A1 | 7/2004 | Moberg et al. |
| 2004/0133220 A1 | 7/2004 | Lashinski et al. |
| 2004/0138744 A1 | 7/2004 | Lashinski et al. |
| 2004/0153146 A1 | 8/2004 | Lashinski et al. |
| 2004/0167478 A1 | 8/2004 | Mooney et al. |
| 2004/0171987 A1 | 9/2004 | Bridle et al. |
| 2004/0176727 A1 | 9/2004 | Shekalim |
| 2004/0193090 A1 | 9/2004 | Lebel et al. |
| 2004/0204673 A1 | 10/2004 | Flaherty |
| 2004/0220551 A1 | 11/2004 | Flaherty et al. |
| 2004/0225252 A1 | 11/2004 | Gillespie et al. |
| 2004/0235446 A1 | 11/2004 | Flaherty et al. |
| 2004/0260233 A1 | 12/2004 | Garibotto et al. |
| 2005/0004514 A1 | 1/2005 | Hochman |
| 2005/0020980 A1 | 1/2005 | Campbell et al. |
| 2005/0022274 A1 | 1/2005 | Campbell et al. |
| 2005/0027182 A1 | 2/2005 | Siddiqui et al. |
| 2005/0038379 A1 | 2/2005 | Beebe et al. |
| 2005/0043710 A1 | 2/2005 | Hadzic et al. |
| 2005/0054994 A1 | 3/2005 | Cioanta et al. |
| 2005/0065464 A1 | 3/2005 | Talbot et al. |
| 2005/0060030 A1 | 5/2005 | Lashinski et al. |
| 2005/0096593 A1 | 5/2005 | Pope et al. |
| 2005/0115622 A1 | 6/2005 | Bennett et al. |
| 2005/0137530 A1 | 6/2005 | Campbell et al. |
| 2005/0137578 A1 | 6/2005 | Heruth et al. |
| 2005/0143864 A1 | 6/2005 | Blomquist |
| 2005/0148832 A1 | 7/2005 | Reghabi et al. |
| 2005/0171512 A1 | 8/2005 | Flaherty |
| 2005/0171513 A1 | 8/2005 | Mann et al. |
| 2005/0171569 A1 | 8/2005 | Girard et al. |
| 2005/0177395 A1 | 8/2005 | Blomquist |
| 2005/0182366 A1 | 8/2005 | Vogt et al. |
| 2005/0211322 A1 | 9/2005 | Lohbeck |
| 2005/0238507 A1 | 10/2005 | Dilanni et al. |
| 2005/0240092 A1 | 10/2005 | Shah et al. |
| 2005/0240119 A1 | 10/2005 | Draudt et al. |
| 2005/0245867 A1 | 11/2005 | Olsen et al. |
| 2005/0246416 A1 | 11/2005 | Blomquist |
| 2005/0267550 A1 | 12/2005 | Hess et al. |
| 2005/0272989 A1 | 12/2005 | Shah et al. |
| 2006/0031094 A1 | 2/2006 | Cohen et al. |
| 2006/0041229 A1 | 2/2006 | Garibotto et al. |
| 2006/0042695 A1 | 3/2006 | Gonia |
| 2006/0076236 A1 | 4/2006 | Shah et al. |
| 2006/0206054 A1 | 4/2006 | Shekalim et al. |
| 2006/0116757 A1 | 6/2006 | Lashinski et al. |
| 2006/0139354 A1 | 6/2006 | Suma |
| 2006/0147313 A1 | 7/2006 | Zengerle et al. |
| 2006/0149214 A1 | 7/2006 | Breiter et al. |
| 2006/0150747 A1 | 7/2006 | Mallet |
| 2006/0150748 A1 | 7/2006 | Mallet |
| 2006/0173444 A1 | 8/2006 | Choy et al. |
| 2006/0178633 A1 | 8/2006 | Garibotto et al. |
| 2006/0189895 A1 | 8/2006 | Neel et al. |
| 2006/0195064 A1 | 8/2006 | Plahey et al. |
| 2006/0202859 A1 | 9/2006 | Mastrototaro et al. |
| 2006/0206029 A1 | 9/2006 | Yair |
| 2006/0229557 A1 | 10/2006 | Fathallah et al. |
| 2006/0243804 A1 | 10/2006 | Cristoffersen et al. |
| 2006/0253086 A1 | 11/2006 | Moberg et al. |
| 2006/0253296 A1 | 11/2006 | Liisberg et al. |
| 2006/0264835 A1 | 11/2006 | Nielson et al. |
| 2006/0271022 A1 | 11/2006 | Steinbeach et al. |
| 2006/0272652 A1 | 12/2006 | Stocker et al. |
| 2006/0281980 A1 | 12/2006 | Randlov et al. |
| 2006/0282290 A1 | 12/2006 | Flaherty et al. |
| 2006/0293576 A1 | 12/2006 | Van Antwerp et al. |
| 2006/0293577 A1 | 12/2006 | Morrison et al. |
| 2007/0000337 A1 | 1/2007 | Gross |
| 2007/0003434 A1 | 1/2007 | Padmanabhan et al. |
| 2007/0016170 A1 | 1/2007 | Kovelman |
| 2007/0016449 A1 | 1/2007 | Cohen et al. |
| 2007/0033074 A1 | 2/2007 | Nitzan et al. |
| 2007/0060869 A1 | 3/2007 | Tolle et al. |
| 2007/0060870 A1 | 3/2007 | Tolle et al. |
| 2007/0066956 A1 | 3/2007 | Finkel |
| 2007/0073129 A1 | 3/2007 | Shah et al. |
| 2007/0073236 A1 | 3/2007 | Mernoe et al. |
| 2007/0088267 A1 | 4/2007 | Shekalim |
| 2007/0093786 A1 | 4/2007 | Goldsmith et al. |
| 2007/0100222 A1 | 5/2007 | Mastrototaro et al. |
| 2007/0100235 A1 | 5/2007 | Kennedy |
| 2007/0112261 A1 | 5/2007 | Enegren et al. |
| 2007/0112301 A1 | 5/2007 | Preuthun et al. |
| 2007/0118405 A1 | 5/2007 | Campbell et al. |
| 2007/0123819 A1 | 5/2007 | Mernoe et al. |
| 2007/0124002 A1 | 5/2007 | Estes et al. |
| 2007/0149926 A1 | 6/2007 | Moberg et al. |
| 2007/0150019 A1 | 6/2007 | Youker et al. |
| 2007/0142822 A1 | 7/2007 | Remde |
| 2007/0156033 A1 | 7/2007 | Causey, III et al. |
| 2007/0156092 A1 | 7/2007 | Estes et al. |
| 2007/0161955 A1 | 7/2007 | Bynum et al. |
| 2007/0167905 A1 | 7/2007 | Estes et al. |
| 2007/0167912 A1 | 7/2007 | Causey et al. |
| 2007/0173712 A1 | 7/2007 | Shah et al. |
| 2007/0173762 A1 | 7/2007 | Estes et al. |
| 2007/0179444 A1 | 8/2007 | Causey et al. |
| 2007/0201992 A1 | 8/2007 | Mernoe et al. |
| 2007/0203459 A1 | 8/2007 | Mernoe et al. |
| 2007/0219480 A1 | 9/2007 | Kamen et al. |
| 2007/0219496 A1 | 9/2007 | Kamen et al. |
| 2007/0219597 A1 | 9/2007 | Kamen et al. |
| 2007/0227907 A1 | 10/2007 | Shah et al. |
| 2007/0228071 A1 | 10/2007 | Kamen et al. |
| 2007/0250007 A1 | 10/2007 | Shekalim et al. |
| 2007/0251835 A1 | 11/2007 | Mehta et al. |
| 2007/0253021 A1 | 11/2007 | Mehta et al. |
| 2007/0253380 A1 | 11/2007 | Jollota et al. |
| 2007/0254593 A1 | 11/2007 | Jollota et al. |
| 2007/0255116 A1 | 11/2007 | Mehta et al. |
| 2007/0255125 A1 | 11/2007 | Moberg et al. |
| 2007/0255126 A1 | 11/2007 | Moberg et al. |
| 2007/0255348 A1 | 11/2007 | Holtzclaw |
| 2007/0258395 A1 | 11/2007 | Jollota et al. |
| 2007/0264130 A1 | 11/2007 | Mallett |
| 2007/0270750 A1 | 11/2007 | Dacquay et al. |
| 2007/0287985 A1 | 12/2007 | Estes et al. |
| 2007/0288176 A1 | 12/2007 | Carlisle et al. |
| 2007/0299399 A1 | 12/2007 | Alferness et al. |
| 2008/0004601 A1 | 1/2008 | Jennewine et al. |
| 2008/0015510 A1 | 1/2008 | Sandoz et al. |
| 2008/0026473 A1 | 1/2008 | Wang et al. |
| 2008/0029173 A1 | 2/2008 | DiPerna |
| 2008/0033350 A1 | 2/2008 | Wilson et al. |
| 2008/0033357 A1 | 2/2008 | Mann et al. |
| 2008/0033360 A1 | 2/2008 | Evans et al. |
| 2008/0033361 A1 | 2/2008 | Evans et al. |
| 2008/0033402 A1 | 2/2008 | Blomquist |
| 2008/0033749 A1 | 2/2008 | Blomquist |
| 2008/0034323 A1 | 2/2008 | Blomquist |
| 2008/0045891 A1 | 2/2008 | Maule et al. |
| 2008/0045902 A1 | 2/2008 | Estes et al. |
| 2008/0045903 A1 | 2/2008 | Estes et al. |
| 2008/0045904 A1 | 2/2008 | Estes et al. |
| 2008/0045931 A1 | 2/2008 | Estes et al. |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051711 A1 | 2/2008 | Mounce et al. |
| 2008/0051716 A1 | 2/2008 | Stutz |
| 2008/0051727 A1 | 2/2008 | Moberg et al. |

(56) References Cited

U.S. PATENT DOCUMENTS

| | | |
|---|---|---|
| 2008/0051765 A1 | 2/2008 | Mounce et al. |
| 2008/0058697 A1 | 3/2008 | Kamen et al. |
| 2008/0065007 A1 | 3/2008 | Peterson et al. |
| 2008/0065016 A1 | 3/2008 | Peterson et al. |
| 2008/0071222 A1 | 3/2008 | Rhad et al. |
| 2008/0071580 A1 | 3/2008 | Marcus et al. |
| 2008/0082040 A1 | 4/2008 | Kubler et al. |
| 2008/0082363 A1 | 4/2008 | Habashi |
| 2008/0092969 A1 | 4/2008 | DiPerna |
| 2008/0097289 A1 | 4/2008 | Steil et al. |
| 2008/0097291 A1 | 4/2008 | Hanson et al. |
| 2008/0097309 A1 | 4/2008 | Enegren et al. |
| 2008/0097327 A1 | 4/2008 | Bente et al. |
| 2008/0097375 A1 | 4/2008 | Bikovsky |
| 2008/0114228 A1 | 5/2008 | McCloskey et al. |
| 2008/0116647 A1 | 5/2008 | Anderson et al. |
| 2008/0119705 A1 | 5/2008 | Patel et al. |
| 2008/0125700 A1 | 5/2008 | Moberg et al. |
| 2008/0126969 A1 | 5/2008 | Blomquist |
| 2008/0281276 A1 | 5/2008 | Shekalim et al. |
| 2008/0139910 A1 | 6/2008 | Mastrototaro et al. |
| 2008/0147004 A1 | 6/2008 | Mann et al. |
| 2008/0147050 A1 | 6/2008 | Mann et al. |
| 2008/0148235 A1 | 6/2008 | Foresti et al. |
| 2008/0156661 A1 | 7/2008 | Cooper et al. |
| 2008/0160492 A1 | 7/2008 | Campbell et al. |
| 2008/0171967 A1 | 7/2008 | Blomquist et al. |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0177154 A1 | 7/2008 | Hansen et al. |
| 2008/0177155 A1 | 7/2008 | Hansen et al. |
| 2008/0183060 A1 | 7/2008 | Steil et al. |
| 2008/0188723 A1 | 8/2008 | Kristensen et al. |
| 2008/0196762 A1 | 8/2008 | Mallett |
| 2008/0197801 A1 | 8/2008 | Manor et al. |
| 2008/0200868 A1 | 8/2008 | Alberti et al. |
| 2008/0200869 A1 | 8/2008 | Bedingfield et al. |
| 2008/0206799 A1 | 8/2008 | Blomquist |
| 2008/0221523 A1 | 9/2008 | Moberg et al. |
| 2008/0228056 A1 | 9/2008 | Blomquist et al. |
| 2008/0234637 A1 | 9/2008 | McConnell et al. |
| 2008/0243062 A1 | 10/2008 | DeStefano et al. |
| 2008/0269584 A1 | 10/2008 | Shekalim |
| 2008/0269680 A1 | 10/2008 | Ibranyan et al. |
| 2008/0269681 A1 | 10/2008 | Kavazov et al. |
| 2008/0269682 A1 | 10/2008 | Kavazov et al. |
| 2008/0269714 A1 | 10/2008 | Mastrototaro et al. |
| 2008/0269723 A1 | 10/2008 | Mastrototaro et al. |
| 2008/0287887 A1 | 11/2008 | Mack et al. |
| 2008/0287922 A1 | 11/2008 | Panduro |
| 2008/0294094 A1 | 11/2008 | Mhatre et al. |
| 2008/0294108 A1 | 11/2008 | Briones et al. |
| 2008/0294109 A1 | 11/2008 | Estes et al. |
| 2008/0294142 A1 | 11/2008 | Patel et al. |
| 2008/0300534 A1 | 12/2008 | Blomquist |
| 2008/0300572 A1 | 12/2008 | Rankers et al. |
| 2008/0300651 A1 | 12/2008 | Gerber et al. |
| 2008/0304365 A1 | 12/2008 | Jarvis et al. |
| 2008/0306434 A1 | 12/2008 | Dobbles et al. |
| 2008/0306444 A1 | 12/2008 | Brister et al. |
| 2008/0317605 A1 | 12/2008 | Amley et al. |
| 2009/0014458 A1 | 1/2009 | Heffron |
| 2009/0018495 A1 | 1/2009 | Panduro |
| 2009/0018779 A1 | 1/2009 | Cohen et al. |
| 2009/0030733 A1 | 1/2009 | Cohen et al. |
| 2009/0036870 A1 | 2/2009 | Mounce et al. |
| 2009/0037020 A1 | 2/2009 | Brown |
| 2009/0043290 A1 | 2/2009 | Villegas et al. |
| 2009/0062767 A1 | 3/2009 | Van Antwerp |
| 2009/0062887 A1 | 3/2009 | Mass et al. |
| 2009/0067989 A1 | 3/2009 | Estes et al. |
| 2009/0069745 A1 | 3/2009 | Estes et al. |
| 2009/0069746 A1 | 3/2009 | Miller et al. |
| 2009/0069749 A1 | 3/2009 | Miller et al. |
| 2009/0069783 A1 | 3/2009 | Ellstrom et al. |
| 2009/0069784 A1 | 3/2009 | Estes et al. |
| 2009/0069785 A1 | 3/2009 | Miller et al. |
| 2009/0069787 A1 | 3/2009 | Estes et al. |
| 2009/0082728 A1 | 3/2009 | Bikovsky |
| 2009/0085768 A1 | 4/2009 | Patel et al. |
| 2009/0088701 A1 | 4/2009 | Larsen |
| 2009/0088731 A1 | 4/2009 | Campbell et al. |
| 2009/0099866 A1 | 4/2009 | Newman |
| 2009/0099867 A1 | 4/2009 | Newman |
| 2009/0101549 A1 | 4/2009 | Kamen et al. |
| 2009/0107335 A1 | 4/2009 | Wilt et al. |
| 2009/0108016 A1 | 4/2009 | Brown et al. |
| 2009/0112626 A1 | 4/2009 | Talbot et al. |
| 2009/0113295 A1 | 4/2009 | Halpern et al. |
| 2009/0131863 A1 | 5/2009 | Carlisle et al. |
| 2009/0137987 A1 | 5/2009 | Ali |
| 2009/0143661 A1 | 6/2009 | Taub et al. |
| 2009/0143732 A1 | 6/2009 | O'Connor et al. |
| 2009/0144089 A1 | 6/2009 | Heywood et al. |
| 2009/0150186 A1 | 6/2009 | Cohen et al. |
| 2009/0150484 A1 | 6/2009 | Roberts |
| 2009/0150865 A1 | 6/2009 | Young et al. |
| 2009/0156990 A1 | 6/2009 | Wenger et al. |
| 2009/0156991 A1 | 6/2009 | Roberts |
| 2009/0157202 A1 | 6/2009 | Roberts et al. |
| 2009/0157622 A1 | 6/2009 | Roberts et al. |
| 2009/0157695 A1 | 6/2009 | Roberts |
| 2009/0158274 A1 | 6/2009 | Roberts |
| 2009/0163855 A1 | 6/2009 | Shin et al. |
| 2009/0170056 A1 | 7/2009 | Nam et al. |
| 2009/0171269 A1 | 7/2009 | Jennewine et al. |
| 2009/0171324 A1 | 7/2009 | Chong et al. |
| 2009/0177142 A1 | 7/2009 | Blomquist et al. |
| 2009/0177147 A1 | 7/2009 | Blomquist et al. |
| 2009/0177154 A1 | 7/2009 | Blomquist |
| 2009/0177248 A1 | 7/2009 | Roberts |
| 2009/0177249 A1 | 7/2009 | Roberts et al. |
| 2009/0177769 A1 | 7/2009 | Roberts |
| 2009/0177991 A1 | 7/2009 | Davis et al. |
| 2009/0191067 A1 | 7/2009 | DiPerna |
| 2009/0192366 A1 | 7/2009 | Mensinger |
| 2009/0192724 A1 | 7/2009 | Brauker et al. |
| 2009/0192745 A1 | 7/2009 | Kamath et al. |
| 2009/0204113 A1 | 8/2009 | Mac Adam et al. |
| 2009/0212966 A1 | 8/2009 | Panduro |
| 2009/0221891 A1 | 9/2009 | Yu et al. |
| 2009/0227855 A1 | 9/2009 | Hill et al. |
| 2009/0227888 A1 | 9/2009 | Salmi et al. |
| 2009/0229374 A1 | 9/2009 | Carlisle et al. |
| 2009/0234594 A1 | 9/2009 | Carlisle et al. |
| 2009/0240193 A1 | 9/2009 | Mensinger et al. |
| 2009/0246035 A1 | 10/2009 | Patzer |
| 2009/0247931 A1 | 10/2009 | Damgaard-Sorensen |
| 2009/0247982 A1 | 10/2009 | Krulevitch |
| 2009/0254037 A1 | 10/2009 | Bryant, Jr. et al. |
| 2009/0256527 A1 | 10/2009 | Welsch et al. |
| 2009/0259183 A1 | 10/2009 | Chong et al. |
| 2009/0259198 A1 | 10/2009 | Chong et al. |
| 2009/0259209 A1 | 10/2009 | Chong et al. |
| 2009/0264825 A1 | 10/2009 | Cote et al. |
| 2009/0267774 A1 | 10/2009 | Enegren et al. |
| 2009/0267775 A1 | 10/2009 | Enegren et al. |
| 2009/0270705 A1 | 10/2009 | Enegren et al. |
| 2009/0270810 A1 | 10/2009 | DeBelser et al. |
| 2009/0270811 A1 | 10/2009 | Mounce et al. |
| 2009/0270833 A1 | 10/2009 | DeBelser et al. |
| 2009/0272928 A1 | 11/2009 | Alvarez et al. |
| 2009/0275886 A1 | 11/2009 | Blomquist et al. |
| 2009/0275887 A1 | 11/2009 | Estes et al. |
| 2009/0275896 A1 | 11/2009 | Kamen et al. |
| 2009/0281393 A1 | 11/2009 | Smith |
| 2009/0287153 A1 | 11/2009 | Bresina et al. |
| 2009/0287180 A1 | 11/2009 | DiPerna |
| 2009/0289916 A1 | 11/2009 | Dai |
| 2009/0292245 A1 | 11/2009 | Basso et al. |

(56) References Cited

U.S. PATENT DOCUMENTS

| | | |
|---|---|---|
| 2009/0299438 A1 | 12/2009 | Nolan et al. |
| 2009/0321675 A1 | 12/2009 | Alvarez et al. |
| 2009/0326458 A1 | 12/2009 | Chong et al. |
| 2010/0008795 A1 | 1/2010 | DiPerna |
| 2010/0010330 A1 | 1/2010 | Rankers et al. |
| 2010/0010647 A1 | 1/2010 | Schroeder et al. |
| 2010/0016791 A1 | 1/2010 | Chong et al. |
| 2010/0022937 A1 | 1/2010 | Bedingfield et al. |
| 2010/0028208 A1 | 2/2010 | Shekalim et al. |
| 2010/0030045 A1 | 2/2010 | Gottlieb et al. |
| 2010/0030092 A1 | 2/2010 | Kristensen et al. |
| 2010/0032041 A1 | 2/2010 | DiPerna |
| 2010/0036327 A1 | 2/2010 | DiPerna |
| 2010/0037680 A1 | 2/2010 | Moberg et al. |
| 2010/0038572 A1 | 2/2010 | Alvarez et al. |
| 2010/0043738 A1 | 2/2010 | Grandvallet et al. |
| 2010/0049126 A1 | 2/2010 | Bronfeld et al. |
| 2010/0049164 A1 | 2/2010 | Estes |
| 2010/0050236 A1 | 2/2010 | Miller et al. |
| 2010/0063765 A1 | 3/2010 | Carlisle et al. |
| 2010/0064257 A1 | 3/2010 | Buck et al. |
| 2010/0065578 A1 | 3/2010 | Di Perna et al. |
| 2010/0065579 A1 | 3/2010 | DiPerna |
| 2010/0069890 A1 | 3/2010 | Graskov et al. |
| 2010/0071446 A1 | 3/2010 | Brown |
| 2010/0081993 A1 | 4/2010 | O'Connor |
| 2010/0087777 A1 | 4/2010 | Hopping et al. |
| 2010/0094114 A1 | 4/2010 | Robinson et al. |
| 2010/0094222 A1* | 4/2010 | Grant ............... A61M 5/14244 604/151 |
| 2010/0095229 A1 | 4/2010 | Dixon et al. |
| 2010/0096019 A1 | 4/2010 | DiPerna |
| 2010/0100026 A1 | 4/2010 | Morris |
| 2010/0100037 A1 | 4/2010 | Cozmi et al. |
| 2010/0105999 A1 | 4/2010 | Dixon et al. |
| 2010/0106100 A1 | 4/2010 | Petersen |
| 2010/0114015 A1 | 5/2010 | Kanderian, Jr. et al. |
| 2010/0114027 A1 | 5/2010 | Jacobson et al. |
| 2010/0119414 A1 | 5/2010 | Eisenhardt et al. |
| 2010/0121169 A1 | 5/2010 | Petisce et al. |
| 2010/0121306 A1 | 5/2010 | Yodfat et al. |
| 2010/0121415 A1 | 5/2010 | Skelton |
| 2010/0130933 A1 | 5/2010 | Holland et al. |
| 2010/0134305 A1 | 6/2010 | Lu et al. |
| 2010/0137833 A1 | 6/2010 | Glynn |
| 2010/0138197 A1 | 6/2010 | Sher |
| 2010/0145262 A1 | 6/2010 | Bengtsson et al. |
| 2010/0145303 A1 | 6/2010 | Yodfat et al. |
| 2010/0152658 A1 | 6/2010 | Hanson et al. |
| 2010/0152674 A1 | 6/2010 | Kavazov et al. |
| 2010/0160740 A1 | 6/2010 | Cohen et al. |
| 2010/0161236 A1 | 6/2010 | Cohen et al. |
| 2010/0161346 A1 | 6/2010 | Getschmann et al. |
| 2010/0162786 A1 | 7/2010 | Keenan et al. |
| 2010/0164727 A1 | 7/2010 | Bazargan et al. |
| 2010/0165795 A1 | 7/2010 | Elder et al. |
| 2010/0168538 A1 | 7/2010 | Keenan et al. |
| 2010/0168539 A1 | 7/2010 | Palerm et al. |
| 2010/0168543 A1 | 7/2010 | Kamath et al. |
| 2010/0168670 A1 | 7/2010 | Srisathapat et al. |
| 2010/0168711 A1 | 7/2010 | Bazargan et al. |
| 2010/0174230 A1 | 7/2010 | Istoc et al. |
| 2010/0174266 A1 | 7/2010 | Estes |
| 2010/0174553 A1 | 7/2010 | Kaufman et al. |
| 2010/0179402 A1 | 7/2010 | Goode, Jr. et al. |
| 2010/0185142 A1 | 7/2010 | Kamen et al. |
| 2010/0185175 A1 | 7/2010 | Kamen et al. |
| 2010/0191084 A1 | 7/2010 | Shah et al. |
| 2010/0191165 A1 | 7/2010 | Appling et al. |
| 2010/0192686 A1 | 8/2010 | Kamen et al. |
| 2010/0198034 A1 | 8/2010 | Thomas et al. |
| 2010/0198107 A1 | 8/2010 | Groll et al. |
| 2010/0198142 A1 | 8/2010 | Sloan et al. |
| 2010/0198143 A1 | 8/2010 | Estes et al. |
| 2010/0198183 A1 | 8/2010 | Lanigan et al. |
| 2010/0198520 A1 | 8/2010 | Breton et al. |
| 2010/0205001 A1 | 8/2010 | Knudsen et al. |
| 2010/0217192 A1 | 8/2010 | Moberg et al. |
| 2010/0217193 A1 | 8/2010 | Moberg et al. |
| 2010/0218132 A1 | 8/2010 | Soni et al. |
| 2010/0218586 A1 | 9/2010 | Rosinko |
| 2010/0222735 A1 | 9/2010 | Plahey et al. |
| 2010/0222765 A1 | 9/2010 | Blomquist et al. |
| 2010/0224192 A1 | 9/2010 | Dixon et al. |
| 2010/0228186 A1 | 9/2010 | Estes et al. |
| 2010/0234709 A1 | 9/2010 | Say et al. |
| 2010/0235439 A1 | 9/2010 | Goodnow |
| 2010/0241065 A1 | 9/2010 | Moberg et al. |
| 2010/0249530 A1 | 9/2010 | Rankers et al. |
| 2010/0249566 A1 | 9/2010 | Suess et al. |
| 2010/0250697 A1 | 9/2010 | Hansen et al. |
| 2010/0251114 A1 | 9/2010 | Wehba et al. |
| 2010/0094251 A1 | 10/2010 | Estes et al. |
| 2010/0253768 A1 | 10/2010 | Ek-Maraghi et al. |
| 2010/0256466 A1 | 10/2010 | Shekalim et al. |
| 2010/0256561 A1 | 10/2010 | Gillespie, Jr. et al. |
| 2010/0256565 A1 | 10/2010 | Mernoe et al. |
| 2010/0256598 A1 | 10/2010 | Mernoe et al. |
| 2010/0261987 A1 | 10/2010 | Kamath |
| 2010/0262078 A1 | 10/2010 | Blomquist |
| 2010/0262434 A1 | 10/2010 | Shaya |
| 2010/0274192 A1 | 10/2010 | Mernoe |
| 2010/0274592 A1 | 10/2010 | Nitzan et al. |
| 2010/0277119 A1 | 11/2010 | Montague et al. |
| 2010/0280329 A1 | 11/2010 | Randlov et al. |
| 2010/0280442 A1 | 11/2010 | Shahmirian et al. |
| 2010/0280486 A1 | 11/2010 | Khair et al. |
| 2010/0286563 A1 | 11/2010 | Bryer et al. |
| 2010/0292556 A1 | 11/2010 | Golden |
| 2010/0298662 A1 | 11/2010 | Yu et al. |
| 2010/0298681 A1 | 11/2010 | Say |
| 2010/0299156 A1 | 11/2010 | Jorgensen |
| 2010/0305421 A1 | 12/2010 | Ow-Wing |
| 2010/0305545 A1 | 12/2010 | Kanderian, Jr. et al. |
| 2010/0312082 A1 | 12/2010 | Batman et al. |
| 2010/0317950 A1 | 12/2010 | Galley et al. |
| 2010/0317951 A1 | 12/2010 | Rutkowski et al. |
| 2010/0323431 A1 | 12/2010 | Rutkowski et al. |
| 2010/0324382 A1 | 12/2010 | Cantwell et al. |
| 2010/0324394 A1 | 12/2010 | Say et al. |
| 2010/0324853 A1 | 12/2010 | Want et al. |
| 2010/0324932 A1 | 12/2010 | Galley et al. |
| 2010/0331651 A1 | 12/2010 | Groll |
| 2010/0331652 A1 | 12/2010 | Groll et al. |
| 2010/0331824 A1 | 12/2010 | Moberg et al. |
| 2011/0004188 A1 | 1/2011 | Shekalim |
| 2011/0006876 A1 | 1/2011 | Moberg et al. |
| 2011/0009725 A1 | 1/2011 | Hill et al. |
| 2011/0009798 A1 | 1/2011 | Kelly et al. |
| 2011/0009813 A1 | 1/2011 | Rankers |
| 2011/0009823 A1 | 1/2011 | Chong et al. |
| 2011/0009825 A1 | 1/2011 | Chong et al. |
| 2011/0009846 A1 | 1/2011 | Istoc et al. |
| 2011/0010105 A1 | 1/2011 | Shah et al. |
| 2011/0015509 A1 | 1/2011 | Peyser |
| 2011/0021898 A1 | 1/2011 | Wei et al. |
| 2011/0022025 A1 | 1/2011 | Sovoie et al. |
| 2011/0028937 A1 | 2/2011 | Powers et al. |
| 2011/0030845 A1 | 2/2011 | Chong et al. |
| 2011/0033833 A1 | 2/2011 | Blomquist |
| 2011/0034786 A1 | 2/2011 | Cadio et al. |
| 2011/0040247 A1 | 2/2011 | Mandro et al. |
| 2011/0040251 A1 | 2/2011 | Blomquist et al. |
| 2011/0044333 A1 | 2/2011 | Sicurello et al. |
| 2011/0046051 A1 | 2/2011 | Moerman |
| 2011/0046454 A1 | 2/2011 | Ejlersen et al. |
| 2011/0046469 A1 | 2/2011 | Nelson et al. |
| 2011/0046697 A1 | 2/2011 | Gerber et al. |
| 2011/0046892 A1 | 2/2011 | Moerman |
| 2011/0047499 A1 | 2/2011 | Mandro et al. |
| 2011/0048938 A1 | 3/2011 | Shah et al. |
| 2011/0048941 A1 | 3/2011 | Shah et al. |
| 2011/0050428 A1 | 3/2011 | Istoc |
| 2011/0053121 A1 | 3/2011 | Heaton |

(56) References Cited

U.S. PATENT DOCUMENTS

| | | |
|---|---|---|
| 2011/0054281 A1 | 3/2011 | Shah et al. |
| 2011/0054390 A1 | 3/2011 | Searle et al. |
| 2011/0054391 A1 | 3/2011 | Ward et al. |
| 2011/0054397 A1 | 3/2011 | Menot et al. |
| 2011/0058485 A1 | 3/2011 | Sloan |
| 2011/0060280 A1 | 3/2011 | Caffey et al. |
| 2011/0060281 A1 | 3/2011 | Aeschlimann et al. |
| 2011/0060328 A1 | 3/2011 | Skwarek et al. |
| 2011/0066108 A1 | 3/2011 | Geipel et al. |
| 2011/0066555 A1 | 3/2011 | Dicks et al. |
| 2011/0071372 A1 | 3/2011 | Sloan et al. |
| 2011/0071464 A1 | 3/2011 | Palerm |
| 2011/0071465 A1 | 3/2011 | Wang et al. |
| 2011/0071765 A1 | 3/2011 | Yodfat et al. |
| 2011/0077481 A1 | 3/2011 | Say et al. |
| 2011/0077493 A1 | 3/2011 | Shadforth et al. |
| 2011/0077554 A1 | 3/2011 | Roe et al. |
| 2011/0077963 A1 | 3/2011 | Knudsen et al. |
| 2011/0078441 A1 | 3/2011 | Dicks et al. |
| 2011/0082439 A1 | 4/2011 | Wenger et al. |
| 2011/0087195 A1 | 4/2011 | Uhland et al. |
| 2011/0092788 A1 | 4/2011 | Long et al. |
| 2011/0092894 A1 | 4/2011 | McGill et al. |
| 2011/0092907 A1 | 4/2011 | Krogh et al. |
| 2011/0092921 A1 | 4/2011 | Beling et al. |
| 2011/0093285 A1 | 4/2011 | Dicks et al. |
| 2011/0093286 A1 | 4/2011 | Dicks et al. |
| 2011/0097480 A1 | 4/2011 | Shah et al. |
| 2011/0098548 A1 | 4/2011 | Budiman |
| 2011/0098637 A1 | 4/2011 | Hill |
| 2011/0098638 A1 | 4/2011 | Chawala et al. |
| 2011/0098674 A1 | 4/2011 | Vincent et al. |
| 2011/0098676 A1 | 4/2011 | Chiang et al. |
| 2011/0101995 A1 | 5/2011 | Shah et al. |
| 2011/0105873 A1 | 5/2011 | Feldman et al. |
| 2011/0105877 A1 | 5/2011 | Wilt et al. |
| 2011/0105955 A1 | 5/2011 | Yudovsky et al. |
| 2011/0105979 A1 | 5/2011 | Schlaeper et al. |
| 2011/0106011 A1 | 5/2011 | Cinar et al. |
| 2011/0106049 A1 | 5/2011 | Damiano et al. |
| 2011/0106050 A1 | 5/2011 | Yodfat et al. |
| 2011/0106318 A1 | 5/2011 | Ledford |
| 2011/0106480 A1 | 5/2011 | Shah et al. |
| 2011/0107853 A1 | 5/2011 | Studer |
| 2011/0108158 A1 | 5/2011 | Huwiler et al. |
| 2011/0111794 A1 | 5/2011 | Bochenko |
| 2011/0112478 A1 | 5/2011 | Gregor et al. |
| 2011/0112504 A1 | 5/2011 | Causey et al. |
| 2011/0112505 A1 | 5/2011 | Starkweather et al. |
| 2011/0112506 A1 | 5/2011 | Starkweather et al. |
| 2011/0118578 A1 | 5/2011 | Timmerman |
| 2011/0118662 A1 | 5/2011 | Mhatre et al. |
| 2011/0118699 A1 | 5/2011 | Yodafat et al. |
| 2011/0118700 A1 | 5/2011 | Remde |
| 2011/0119087 A1 | 5/2011 | Drucker et al. |
| 2011/0120206 A1 | 5/2011 | Troughton et al. |
| 2011/0124996 A1 | 5/2011 | Reinke et al. |
| 2011/0124999 A1 | 5/2011 | Reggiardo et al. |
| 2011/0125085 A1 | 5/2011 | McGill et al. |
| 2011/0125095 A1 | 5/2011 | Lebel et al. |
| 2011/0125530 A1 | 5/2011 | Drucker et al. |
| 2011/0126188 A1 | 5/2011 | Bernstein et al. |
| 2011/0130746 A1 | 6/2011 | Budiman |
| 2011/0133946 A1 | 6/2011 | Kopp et al. |
| 2011/0137239 A1 | 6/2011 | DeBelser et al. |
| 2011/0144569 A1 | 6/2011 | Britton et al. |
| 2011/0144586 A1 | 6/2011 | Michaud et al. |
| 2011/0144616 A1 | 6/2011 | Michaud et al. |
| 2011/0149759 A1 | 6/2011 | Jollota |
| 2011/0151571 A1 | 6/2011 | Wooldridge |
| 2011/0152653 A1 | 6/2011 | Shekalim et al. |
| 2011/0152654 A1 | 6/2011 | Wang et al. |
| 2011/0152757 A1 | 6/2011 | Beck et al. |
| 2011/0152769 A1 | 6/2011 | Ramey et al. |
| 2011/0152770 A1 | 6/2011 | DiPerna et al. |
| 2011/0152824 A1 | 6/2011 | DiPerna et al. |
| 2011/0152970 A1 | 6/2011 | Jollota et al. |
| 2011/0154237 A1 | 6/2011 | Bush et al. |
| 2011/0160650 A1 | 6/2011 | Chong et al. |
| 2011/0160654 A1 | 6/2011 | Hanson et al. |
| 2011/0160666 A1 | 6/2011 | Hanson et al. |
| 2011/0160667 A1 | 6/2011 | Bazargan et al. |
| 2011/0160678 A1 | 6/2011 | Chong et al. |
| 2011/0160695 A1 | 6/2011 | Sigrist et al. |
| 2011/0163125 A1 | 7/2011 | Beavis et al. |
| 2011/0166544 A1 | 7/2011 | Verhoef |
| 2011/0166875 A1 | 7/2011 | Hayter et al. |
| 2011/0172744 A1 | 7/2011 | Davis et al. |
| 2011/0178461 A1 | 7/2011 | Chong et al. |
| 2011/0178462 A1 | 7/2011 | Moberg et al. |
| 2011/0184264 A1 | 7/2011 | Galasso et al. |
| 2011/0190614 A1 | 8/2011 | Brister et al. |
| 2011/0190694 A1 | 8/2011 | Lanier, Jr. et al. |
| 2011/0190700 A1 | 8/2011 | Kavazov et al. |
| 2011/0190701 A1 | 8/2011 | Remde et al. |
| 2011/0192478 A1 | 8/2011 | Chong et al. |
| 2011/0196213 A1 | 8/2011 | Thukral et al. |
| 2011/0196248 A1 | 8/2011 | Grunwald |
| 2011/0196289 A1 | 8/2011 | Plahey et al. |
| 2011/0205065 A1 | 8/2011 | Strachan et al. |
| 2011/0208122 A1 | 8/2011 | Shekalim |
| 2011/0208123 A1 | 8/2011 | Gray et al. |
| 2011/0208155 A1 | 8/2011 | Palerm et al. |
| 2011/0213225 A1 | 9/2011 | Bernstein et al. |
| 2011/0213306 A1 | 9/2011 | Hanson et al. |
| 2011/0224522 A1 | 9/2011 | Fennell |
| 2011/0224601 A1 | 9/2011 | Shekalim |
| 2011/0230821 A1 | 9/2011 | Babic |
| 2011/0230825 A1 | 9/2011 | Kamen et al. |
| 2011/0247397 A1 | 10/2011 | Friedli et al. |
| 2011/0251557 A1 | 10/2011 | Powers |
| 2011/0251579 A1 | 10/2011 | Aklog et al. |
| 2011/0256024 A1 | 10/2011 | Cole et al. |
| 2011/0257895 A1 | 10/2011 | Brauker et al. |
| 2011/0309017 A1 | 12/2011 | Shekalim et al. |
| 2011/0309107 A1 | 12/2011 | Shekalim et al. |
| 2011/0319862 A1 | 12/2011 | Friedman et al. |
| 2012/0013625 A1 | 1/2012 | Blomquist |
| 2012/0013802 A1 | 1/2012 | Blomquist |
| 2012/0017688 A1 | 1/2012 | Shekalim |
| 2012/0022452 A1 | 1/2012 | Welsch et al. |
| 2012/0029433 A1 | 2/2012 | Michaud et al. |
| 2012/0029468 A1 | 2/2012 | DiPerna et al. |
| 2012/0029486 A1 | 2/2012 | DiPerna |
| 2012/0029708 A1 | 2/2012 | Miller et al. |
| 2012/0030610 A1 | 2/2012 | DiPerna |
| 2012/0059673 A1 | 3/2012 | Cohen et al. |
| 2012/0232520 A1 | 9/2012 | Sloanet et al. |
| 2013/0012877 A1 | 1/2013 | Debelser et al. |
| 2013/0012917 A1 | 1/2013 | Miller et al. |
| 2013/0053816 A1 | 2/2013 | Diperna et al. |
| 2013/0150766 A1 | 6/2013 | Olde et al. |
| 2013/0204542 A1 | 8/2013 | Olde et al. |
| 2013/0283196 A1 | 10/2013 | Farnan et al. |
| 2013/0296788 A1 | 11/2013 | Ogihara |
| 2013/0298024 A1 | 11/2013 | Rhee et al. |
| 2013/0324928 A1 | 12/2013 | Kruse |
| 2013/0332874 A1 | 12/2013 | Rosinko et al. |
| 2014/0039392 A1 | 2/2014 | Geipel et al. |
| 2014/0039805 A1 | 2/2014 | Sharpe, Jr. et al. |
| 2014/0054883 A1 | 2/2014 | Lanigan et al. |
| 2014/0094764 A1 | 4/2014 | Blomquist et al. |
| 2014/0276409 A1 | 9/2014 | Rosinko et al. |
| 2014/0276537 A1 | 9/2014 | Kruse |
| 2014/0276538 A1 | 9/2014 | Michaud |
| 2015/0174320 A1 | 6/2015 | Grant et al. |
| 2016/0082186 A1 | 3/2016 | Rosinko et al. |

FOREIGN PATENT DOCUMENTS

| | | |
|---|---|---|
| CN | 2668847 Y | 1/2005 |
| DE | 399065 | 7/1924 |
| DE | 19819407 | 11/1999 |
| EP | 0055836 | 7/1982 |

(56) References Cited

FOREIGN PATENT DOCUMENTS

| | | |
|---|---|---|
| EP | 0272530 | 6/1988 |
| EP | 0376894 | 12/1988 |
| EP | 0385916 | 5/1990 |
| EP | 0494042 | 7/1992 |
| EP | 0560571 | 9/1993 |
| EP | 1217275 B1 | 9/2004 |
| EP | 1938750 | 7/2008 |
| GB | 2159496 | 12/1985 |
| JP | 06-016165 | 4/1994 |
| JP | 08-312820 | 11/1996 |
| JP | 2002-143293 | 5/2002 |
| JP | 2006-009944 | 1/2006 |
| JP | 2006-101985 | 4/2009 |
| JP | 2009-148591 | 7/2009 |
| JP | 2010-075736 | 4/2010 |
| KR | 10-2001-0080519 | 8/2001 |
| WO | WO 90/013795 | 11/1990 |
| WO | WO 91/000753 | 1/1991 |
| WO | WO 94/026329 | 11/1994 |
| WO | WO 95/032013 | 11/1995 |
| WO | WO9532013 | 11/1995 |
| WO | WO 96/008049 | 3/1996 |
| WO | WO9608040 | 3/1996 |
| WO | WO9613288 | 5/1996 |
| WO | WO 96/025189 | 8/1996 |
| WO | WO 98/019627 | 5/1998 |
| WO | WO 98/057683 | 12/1998 |
| WO | WO 99/001088 | 1/1999 |
| WO | WO9964103 | 12/1999 |
| WO | WO 00/010628 | 3/2000 |
| WO | WO 00/035527 | 6/2000 |
| WO | WO 00/040346 | 7/2000 |
| WO | WO 00/072900 | 12/2000 |
| WO | WO 01/030422 | 5/2001 |
| WO | WO0130422 | 5/2001 |
| WO | WO 02/011049 | 2/2002 |
| WO | WO 02/011791 | 2/2002 |
| WO | WO 02/026102 | 4/2002 |
| WO | WO 03/081052 | 3/2003 |
| WO | WO0228532 A9 | 5/2003 |
| WO | WO 03/102737 | 6/2003 |
| WO | WO03082091 | 10/2003 |
| WO | WO 04/009152 | 1/2004 |
| WO | WO2004009160 | 1/2004 |
| WO | WO 04/088148 | 3/2004 |
| WO | WO 04/036150 | 4/2004 |
| WO | WO 04/047677 | 6/2004 |
| WO | WO 04/060464 | 7/2004 |
| WO | WO 09/098648 | 8/2004 |
| WO | WO 04/056412 | 12/2004 |
| WO | WO 04/105827 | 12/2004 |
| WO | WO 05/082450 | 2/2005 |
| WO | WO 05/018507 | 3/2005 |
| WO | WO 06/001024 | 1/2006 |
| WO | WO 08/028509 | 9/2006 |
| WO | WO 08/037270 | 9/2006 |
| WO | WO 08/037271 | 9/2006 |
| WO | WO 08/037272 | 9/2006 |
| WO | WO 08/037273 | 9/2006 |
| WO | WO 06/108219 | 10/2006 |
| WO | WO 08/043381 | 10/2006 |
| WO | WO2006127841 | 11/2006 |
| WO | WO 07/038059 | 4/2007 |
| WO | WO 07/038060 | 4/2007 |
| WO | WO 07/038091 | 4/2007 |
| WO | WO2007047279 | 4/2007 |
| WO | WO 07/056504 | 5/2007 |
| WO | WO 07/056592 | 5/2007 |
| WO | WO2007065944 | 6/2007 |
| WO | WO 07/089983 | 8/2007 |
| WO | WO 07/098265 | 8/2007 |
| WO | WO 07/098287 | 8/2007 |
| WO | WO 07/106232 | 9/2007 |
| WO | WO 07/119149 | 10/2007 |
| WO | WO 08/050126 | 10/2007 |
| WO | WO 08/050128 | 10/2007 |
| WO | WO2008024812 | 2/2008 |
| WO | WO 08/056363 | 5/2008 |
| WO | WO 08/144693 | 5/2008 |
| WO | WO 08/144695 | 5/2008 |
| WO | WO 08/144697 | 5/2008 |
| WO | WO 08/144698 | 5/2008 |
| WO | WO 09/032402 | 7/2008 |
| WO | WO 09/035759 | 7/2008 |
| WO | WO 09/035761 | 7/2008 |
| WO | WO 09/035762 | 7/2008 |
| WO | WO 08/103175 | 8/2008 |
| WO | WO 08/121599 | 10/2008 |
| WO | WO 09/032399 | 10/2008 |
| WO | WO 09/032400 | 10/2008 |
| WO | WO 09/035753 | 10/2008 |
| WO | WO 09/106233 | 2/2009 |
| WO | WO2009016636 | 2/2009 |
| WO | WO2009044221 | 4/2009 |
| WO | WO 09/094590 | 7/2009 |
| WO | WO 09/108639 | 9/2009 |
| WO | WO 09/124133 | 10/2009 |
| WO | WO2009143188 | 11/2009 |
| WO | WO 09/147680 | 12/2009 |
| WO | WO 10/016977 | 2/2010 |
| WO | WO 10/016978 | 2/2010 |
| WO | WO 10/097774 | 2/2010 |
| WO | WO 10/033634 | 3/2010 |
| WO | WO 10/033878 | 3/2010 |
| WO | WO 10/038031 | 4/2010 |
| WO | WO 10/096449 | 8/2010 |
| WO | WO 10/099490 | 9/2010 |
| WO | WO 10/113162 | 10/2010 |
| WO | WO2011001267 | 1/2011 |
| WO | WO 11/014704 | 2/2011 |
| WO | WO 11/017667 | 2/2011 |
| WO | WO2011131777 | 10/2011 |
| WO | WO2012019726 | 2/2012 |

OTHER PUBLICATIONS

European Search Report dated Mar. 3, 2016 (dated Feb. 23, 2016) for European Application No. 13800986.5.
European Search Report for European Application No. EP15168432 dated Sep. 8, 2015.
International Search Report and Written Opinion for International Application No. PCT/US2014/021171 dated Jun. 8, 2014.
Canadian Examiner's Report for Canadian Application No. 2,769,030 dated Aug. 27, 2014.
International Search Report and Written Opinion for International Application No. PCT/US2013/044259 dated Sep. 6, 2013.
European Search Report for European Application No. EP09751416.0-2319 dated Nov. 21, 2012.
Examination Report No. 1 for Australian Patent Application No. 2009249132 dated Jan. 23, 2014.
European Search Report for European Application No. 14152623.6-1506 dated Mar. 11, 2014.
European Search Report for European Application No. EP09704892 dated Jan. 28, 2013.
International Search Report and Written Opinion for International Application No. PCT/US2009/09116 dated Feb. 4, 2010.
International Search Report and Written Opinion for International Application No. PCT/US2010/043789 dated Apr. 11, 2011.
PCT Search Report and Written Opinion dated Jun. 9, 2014 for PCT Application No. PCT/US2014/018861 filed Feb. 27, 2014, 10 pages.
Application and File History for U.S. Appl. No. 13/838,617, filed Mar. 15, 2013, inventor Kruse.
Application and File History for U.S. Appl. No. 12/846,706, filed Jul. 29, 2010, inventors Michaud et al.
Application and File History for U.S. Appl. No. 12/846,733, filed Jul. 29, 2010 inventors Michaud et al.
Application and File History for U.S. Appl. No. 12/846,720, filed Jul. 29, 2010 inventors Michaud et al.

(56) References Cited

OTHER PUBLICATIONS

Application and File History for U.S. Appl. No. 12/846,734, filed Jul. 29, 2010 inventors Verhoef et al.
Application and File History for U.S. Appl. No. 13/270,160, filed Oct. 10, 2011 inventors Michaud et al.
Application and File History for U.S. Appl. No. 13/271,156, filed Oct. 11, 2011 inventors DiPerna et al.
Application and File History for U.S. Appl. No. 13/829,115, filed Mar. 14, 2013 inventors Rosinko et al.
Application and File History for U.S. Appl. No. 13/557,163, filed Jul. 24, 2012 inventors DiPerna et al.
Application and File History for U.S. Appl. No. 13/832,531 dated Mar. 15, 2013, inventor Kruse.
Application and File History for U.S. Appl. No. 13/842,990 dated Mar. 15, 2013, inventor Michaud.
Application and File History for U.S. Appl. No. 14/936,979 dated Nov. 10, 2015, inventors Metzmaker et al.
Search Report and Written Opinion dated Mar. 4, 2013 for PCT Application No. PCT/US2012/048020 filed Jul. 24, 2012, 10 pages.
International Preliminary Report on Patentability dated Jan. 28, 2014 for PCT Application No. PCT/US2012/048020 filed Jul. 24, 2012, 7 pages.
Search Report and Written Opinion dated Aug. 22, 2013 for PCT Application No. PCT/US2013/040269 filed May 9, 2013, 17 pages.
International Preliminary Report on Patentability dated Oct. 29, 2014 for PCT Application No. PCT/US2013/040269 filed May 9, 2013, 9 pages.
Application and File History for U.S. Appl. No. 15/241,257, filed Aug. 19, 2016, inventor Michaud.
U.S. Appl. No. 60/789,243, filed Apr. 5, 2006, Beavis.
International Search Report dated Sep. 10, 2004 in International Application: PCT/US2003/022703 filed on Jul. 15, 2003 and published as: WO 04/009152 on Jan. 29, 2004.
International Search Report and Written Opinion dated Jul. 23, 2007 in International Application: PCT/2007/060633 filed on: Jan. 17, 2007 and published as: WO 07/089983 on: Aug. 9, 2007.
International Preliminary Report on Patentability dated Jul. 29, 2008 in International Application: PCT/2007/060633 filed on: Jan. 17, 2007 and published as: WO 07/089983 on: Aug. 9, 2007.
International Search Report and Written Opinion dated May 29, 2009 in International Application: PCT/US2009/035022 filed on: Jan. 23, 2009 and published as: WO 09/108639 on: Sep. 3, 2009.
International Preliminary Report on Patentability dated Sep. 10, 2010 in International Application: PCT/US2009/035022 filed on: Jan. 23, 2009 and published as: WO 09/108639 on: Sep. 3, 2009.
International Preliminary Report on Patentability dated Oct. 6, 2009 in International Application: PCT/2008/058044 filed on: Mar. 24, 2008 and published as: WO 08/121599 on: Oct. 9, 2009.
Written Opinion of the International Searching Authority dated Aug. 11, 2008 in International Application: PCT/US2008/058044 filed on: Mar. 24, 2008 and published as: WO 08/121599 on: Oct. 9, 2009.
International Search Report and Written Opinion dated Feb. 17, 2011 in International Application: PCT/US2009/049110 filed on: Jun. 29, 2009 and published as: WO 10/016977 on: Feb. 11, 2010.
International Search Report and Written Opinion dated Jan. 27, 2010 in International Application: PCT/US2009/049110 filed on: Jun. 29, 2009 and published as: WO 10/016977 on: Feb. 11, 2010.
International Search Report and Written Opinion dated Feb. 17, 2011 in International Application: PCT/2009/049116 filed on: Jun. 29, 2009 and published as: WO 10/016978 on: Feb. 11, 2010.
International Search Report and Written Opinion dated Feb. 4, 2010 in International Application: PCT/2009/049116 filed on: Jun. 29, 2009 and published as: WO 10/016978 on: Feb. 11, 2010.
International Preliminary Report on Patentability dated Aug. 5, 2010 in International Application: PCT/US2009/031906 filed on Jan. 23, 2009 and published as: WO 09/094590 on Jul. 30, 2009.
International Search Report and Written Opinion dated Jul. 28, 2009 in International Application: PCT/US2009/031906 filed on Jan. 23, 2009 and published as: WO 09/094590 on Jul. 30, 2009.
International Search Report and Written Opinion dated Jan. 4, 2010 in International Application: PCT/US2009/044569 filed on: May 19, 2009 and published as: WO 09/143188 on: Nov. 26, 2009.
International Preliminary Report on Patentability dated Dec. 2, 2010, in International Patent Application No. PCT/US2009/044569 filed on: May 19, 2009 and published as WO 2009/143188 on: Nov. 26, 2009.
International Preliminary Report on Patentability dated Mar. 31, 2011 in International Application: PCT/2009/057208 filed on: Sep. 16, 2009 and published as: WO 10/033634 on: Mar. 25, 2010.
International Search Report and Written Opinion dated Apr. 1, 2010 in International Application: PCT/2009/057208 filed on: Sep. 16, 2009 and published as: WO 10/033634 on: Mar. 25, 2010.
International Search Report and Written Opinion dated Sep. 30, 2010 in International Application: PCT/2010/025663 filed on: Feb. 26, 2010 and published as: WO 10/099490 on: Sep. 2, 2010.
International Preliminary Report on Patentability dated Mar. 31, 2011 in International Application: PCT/2009/57591 filed on: Sep. 18, 2009 and published as: WO 10/033878 on: Mar. 25, 2010.
International Search Report and Written Opinion dated Apr. 12, 2010 in International Application: PCT/2009/57591 filed on: Sep. 18, 2009 and published as: WO 10/033878 on: Mar. 25, 2010.
International Search Report and Written Opinion dated Apr. 11, 2011 in International Application: PCT/2010/034789 filed on: Jul. 29, 2010 and published as: WO 11/014704 on: Feb. 3, 2011.
Arrow International Europe Web Page for: Multiple Lumen Peripheral Catheter, Product No. IV-01150, printed from the internet on Nov. 15, 2011.
AngioDynamics, Smart Port, Power-Injectable Ports Product Brochure, Copyright 2010 AngioDynamics,Inc.
i-port ADVANCE product brochure, distributed by: Patton Medical Devices and Manufactured by Unomedical, a Cardiovascular Company, Copyright, 2007-2010 Patton Medical Devices, LP.
Miller, John E., "The Reciprocating Pump, Theory, Design and Use," Chapter 1, "Pump Types", Krieger Publishing Company, Malabar, Florida 1995.
Spring Zone Insulin Delivery System Product Brochure, Copyright 2011 Spring (formerly NiliMEDIX), a D-Medical company.
Extended European Search Report dated Mar. 6, 2012 in European Application No. EP 09751416 based on International Application No: PCT/US2009/044569.

\* cited by examiner

SYSTEM AND METHOD FOR DETECTING OCCLUSIONS IN AN INFUSION PUMP

RELATED APPLICATION

This application is a continuation of application Ser. No. 13/829,115 filed Mar. 14, 2013, which is hereby fully incorporated herein by reference.

FIELD OF THE INVENTION

The present invention relates to detecting occlusions in infusion pumps and, more particularly, the present invention relates to detecting occlusions in ambulatory infusion pumps that utilize replaceable fluid cartridges.

BACKGROUND

There are many applications in academic, industrial, and medical fields, as well as others, that can benefit from devices and methods capable of accurately and controllably delivering fluids, including liquids and gases, and that benefit from administering fluids in known and controlled quantities. Such devices and methods may be particularly useful in the medical field where many treatments include the administration of a known amount of a substance at predetermined intervals.

Insulin-injecting pumps have been developed for the administration of insulin for those suffering from both Type I and Type II diabetes. Recently, continuous subcutaneous insulin injection and/or infusion therapy with portable infusion devices has been adapted for the treatment of diabetes. Such therapy may include the regular and/or continuous injection or infusion of insulin into the skin of a person suffering from diabetes, and offers an alternative to multiple daily injections of insulin by an insulin syringe or an insulin pen. Such pumps can be ambulatory/portable infusion pumps that are worn by the user and that may use replaceable cartridges. Examples of such pumps and various features that can be associated with such pumps include those disclosed in U.S. patent application Ser. No. 13/557,163, U.S. patent application Ser. No. 12/714,299, U.S. patent application Ser. No. 12/538,018, U.S. Provisional Patent Application No. 61/655,883, U.S. Provisional Patent Application No. 61/656,967 and U.S. Pat. No. 8,287,495, each of which is incorporated herein by reference.

There are, however, some drawbacks associated with the use of subcutaneous injection syringes and/or some currently available infusion pumps for the delivery of insulin and other fluids. Infusion pumps generally deliver fluids to patients through a flexible line having a lumen through which the fluid is pumped from the device to the patient. These fluid lines can become occluded such that fluid cannot be pumped through the line to the patient. Early detection of an occlusion condition is important because the patient may not be receiving the prescribed amount of fluid, which can be harmful and in some instances even fatal. Although there are a number of systems that address the occlusion issue by incorporating sensors to sense whether pressure has increased in the fluid line, such systems can suffer from drawbacks related to accuracy, and from the cost associated with the use of sensors in disposable cartridges. For example, when measuring small signals over long periods of time, sensor drift or other long term systematic effects, such as temperature or ambient pressure changes, can affect the accuracy of the readings taken with such sensors.

There is an ongoing need for improvement in systems and methods for detecting occlusions in ambulatory infusion pumps.

SUMMARY OF THE INVENTION

Occlusions in a delivery line of an infusion pump can be detected by measuring pressure differentials in the pump over short periods of time in order to minimize the effects of long term systematic sensor changes. In a delivery mode such as basal insulin delivery where a small portion of a volume of fluid is delivered, pressure readings can be obtained before and after the motor move to deliver each portion and compared. The differentials after one or more motor moves can be compared to determine whether an occlusion is present. In a delivery mode such as bolus insulin delivery in which an entire volume of fluid is delivered, pressure differentials can be obtained for consecutive deliveries at a common point in the delivery cycle of each delivery. Comparison of these pressure values can be used to determine whether an occlusion is present.

In some embodiments, an ambulatory infusion system includes a disposable infusion cartridge having a collapsible reservoir for containing a fluid and an interior volume between an outer surface of the collapsible reservoir and an inner surface of a rigid shell disposed over the reservoir. A pump device can selectively receive the infusion cartridge and cooperate with the infusion cartridge to deliver fluid from the reservoir to the patient. A pressure sensor located in one of the infusion cartridge and the pump can obtain pressure readings in the interior volume of the cartridge. A processor can compare one or more pressure readings taken before, during or after operation of the pump and compare the readings to determine whether an occlusion is present.

In one embodiment, occlusions are detected while an ambulatory infusion pump is operating in a basal delivery mode. A pump motor is actuated to deliver a portion of fluid contained in a collapsible volume of the cartridge. A first pressure reading is obtained prior to actuating the motor and a second reading is obtained after actuating the motor. The pressure readings are compared and if the readings are not the same, or within a predetermined threshold of each other, an occlusion alarm is generated. In some embodiments, more than two pressure readings are compared.

In another embodiment, occlusions are detected while an ambulatory infusion pump is operated in a bolus delivery mode. In bolus delivery, the pump motor is actuated to deliver the entire contents of the collapsible volume. A pressure reading is obtained at a time prior to delivering all of the fluid, such as right before the fluid delivery is initiated, and a second pressure reading is obtained at a time after all of the fluid has been delivered and when the delivery mechanism is in the same position as in the previous cycle. The pressure readings are compared, and an occlusion alarm is generated if the pressure readings are the same.

Certain embodiments are described further in the following description, examples, claims, and drawings. These embodiments will become more apparent from the following detailed description when taken in conjunction with the accompanying exemplary drawings.

DETAILED DESCRIPTION

Provided herein are systems, devices and methods for detecting occlusions in an infusion pump and particularly in an insulin pump. Some embodiments may include advances in the internal components, the control circuitry, and improvements in a user interface of the systems and devices. The advances may allow for a safer and more accurate delivery of medicament to a patient than is currently attainable today from other devices, systems, and methods. Although embodiments described herein may be discussed in the context of the controlled delivery of insulin, delivery of other medicaments as well as other applications are also contemplated. Device and method embodiments discussed herein may be used for pain medication, chemotherapy, iron chelation, immunoglobulin treatment, dextrose or saline IV delivery, or any other suitable indication or application. Non-medical applications are also contemplated.

Figure 1A:
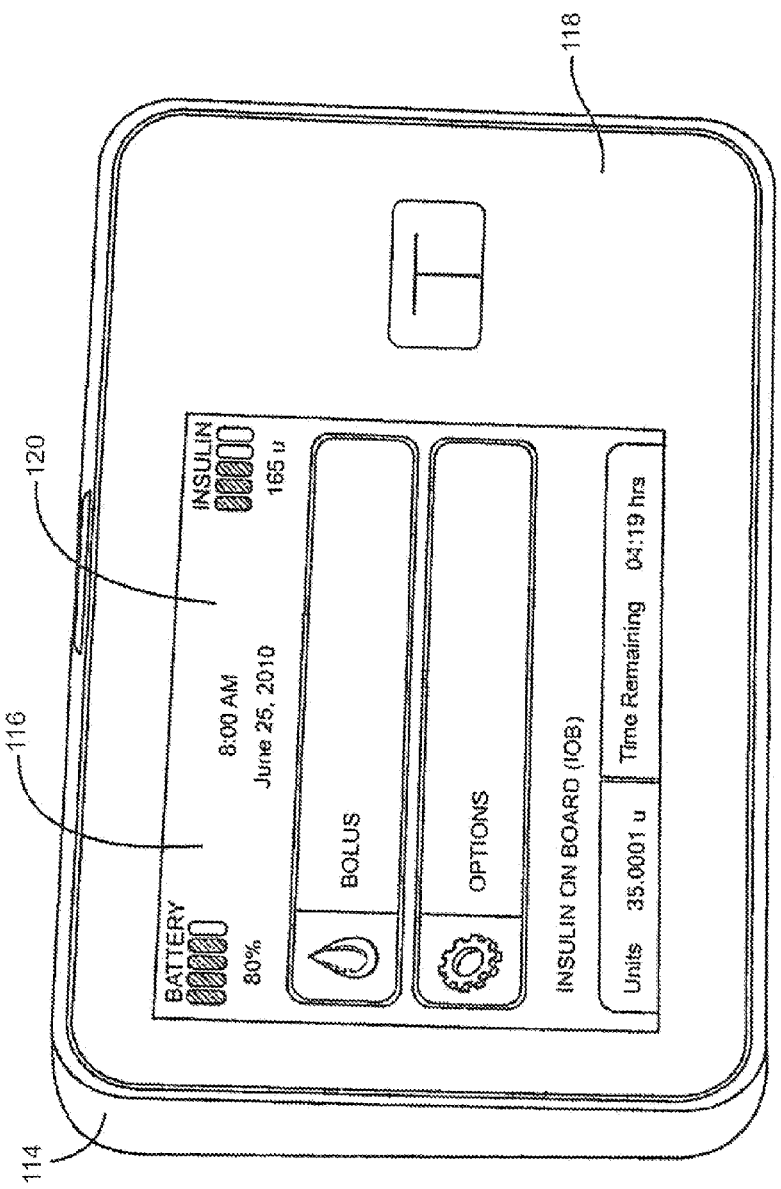
FIG. 1A is a front perspective view of an embodiment of a portable infusion pump system.
Figure 1B:
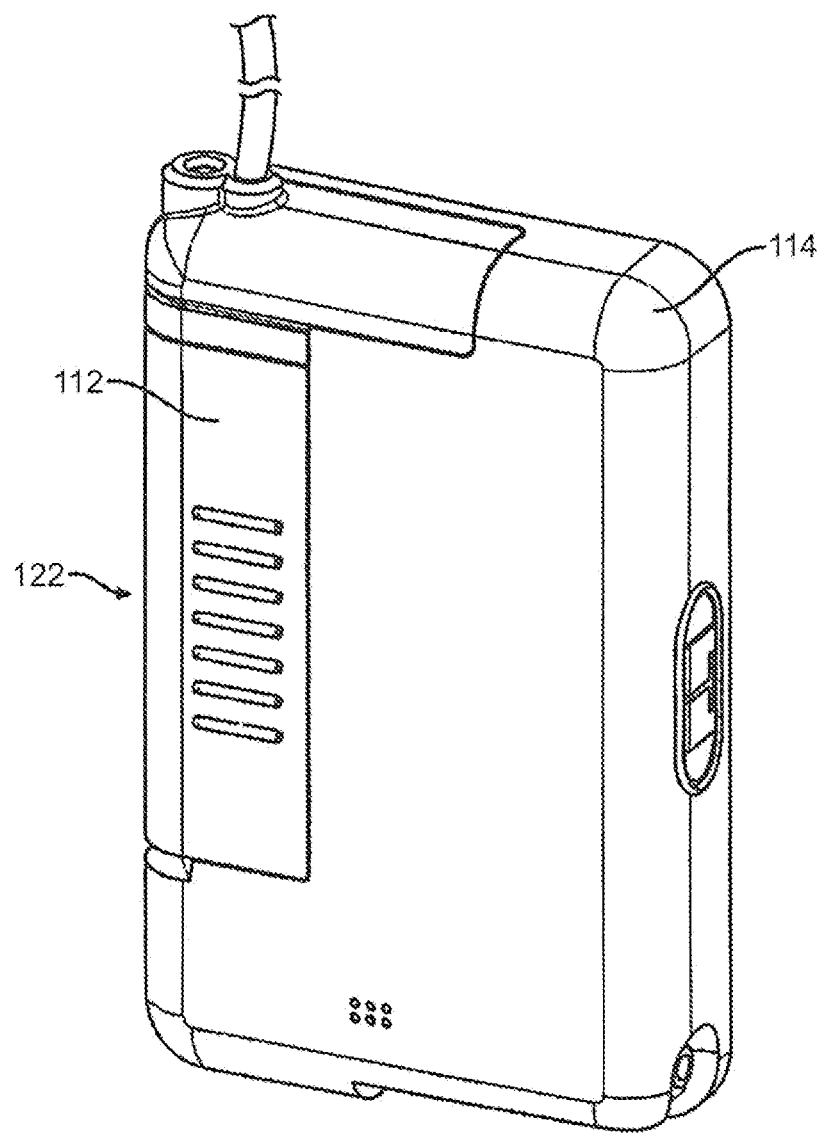
FIG. 1B is a rear perspective view of the infusion pump of FIG. 1A, including an attached infusion cartridge.

FIGS. 1A-1D depict an embodiment of a portable infusion pump system 110 including an infusion cartridge 112 and pump device 114. Infusion cartridge 112 can be a reversibly removable and interchangeable element that may be inserted into different pump devices. Referring to FIG. 1A, a front view of the pump device 114 is depicted and includes a user friendly user interface 116 on a front surface 118 of the pump device 114. The user interface 116 includes a touch sensitive screen 120 that may be configured to display a variety of screens used for displaying data, facilitating data entry by a patient, providing visual tutorials, as well as other interface features that may be useful to a patient operating the pump device 114. FIG. 1B is a rear view of the pump device 114 and illustrates the detachable installment of the infusion cartridge 112 in a slot 122 of the pump device 114 which is configured to accept the cartridge 112.

Figure 1C:
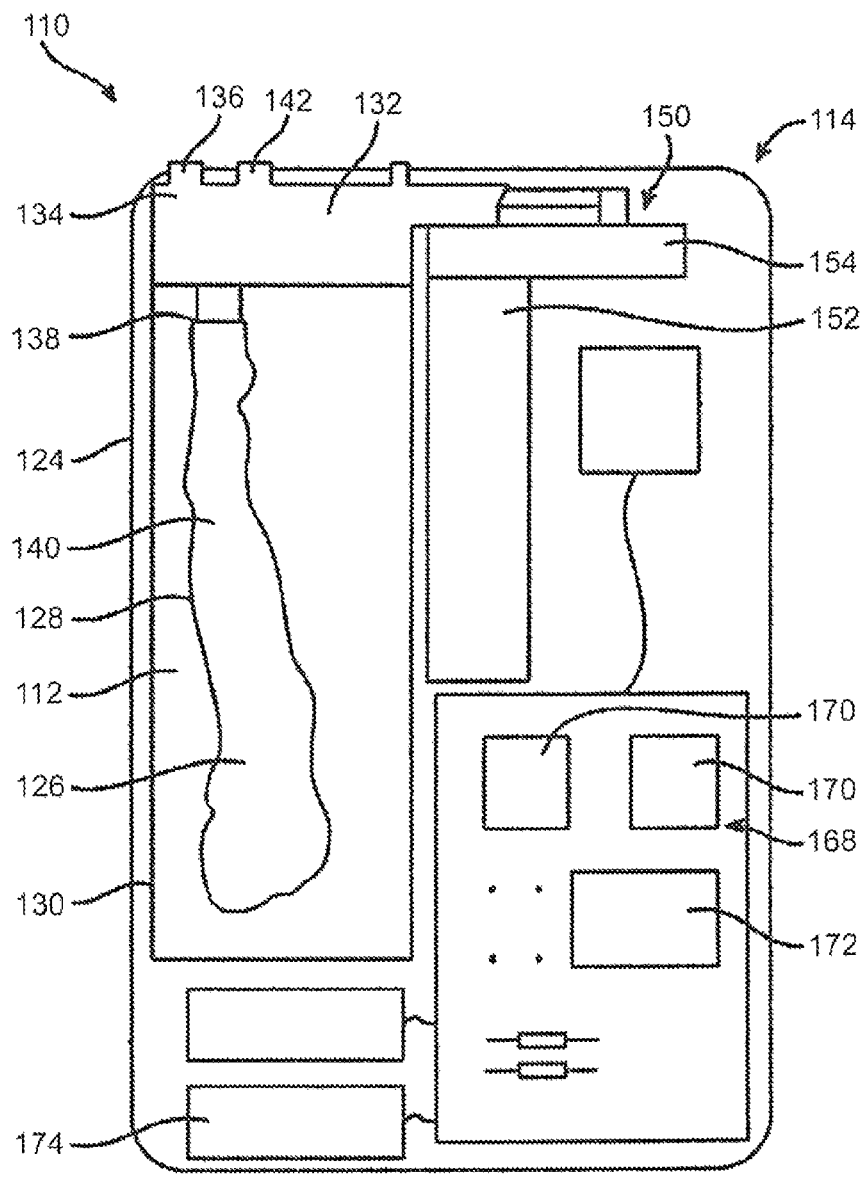
FIG. 1C is a rear schematic view of an interior of the infusion pump and cartridge embodiments of FIGS. 1A and 1B.

FIG. 1C is a schematic view of an open housing 124 of the pump device 114 depicting components that may be included in embodiments of the pump device 114. The cartridge 112 may include a fluid interface configured to receive a fluid such as collapsible reservoir 126. The collapsible reservoir 126 may be formed from a flexible material or membrane 128 that is disposed about an interior volume of the reservoir 126. The cartridge 112 also includes a substantially rigid container 130 sealed around the flexible material of the collapsible reservoir 126. A disposable delivery mechanism 132 is disposed within the disposable cartridge 112 and may have a fill port 134 with a re-sealable septum 136 sealed over the fill port 134, a reservoir inlet port 138 in fluid communication with an interior volume 140 of the collapsible reservoir 126, a fluid dispense port 142 in fluid communication with a bore 144 of the delivery mechanism 132, a vent inlet port 146 and a vent outlet port 148 both in fluid communication with the bore 144. The collapsible reservoir 126 may have a bag-like structure with flexible walls that can collapse and expand depending upon the amount of material in the volume of the reservoir. The interior volume of the reservoir may be in fluid isolation from the remaining interior volume of the rigid container 130.

The cartridge 112 may be releasably and operatively secured to a housing 124 of the pump device 114. The housing 124 may be configured to house a drive mechanism 150 including a motor 152 and gear box 154 disposed in the housing 124 and detachably coupled to a spool member 156 of the delivery mechanism 132. At least one pressure sensor 158 may be disposed in a volume 160 between an outside surface 162 of the flexible material or membrane 128 of the collapsible reservoir 126 and an inside surface 164 of the substantially rigid shell or case 130. This interior volume 160 is typically sealed but can be selectively vented to the atmosphere. The graphic user interface 116 may be operatively coupled to a controller 168, which may include at least one processor 170, a memory device 172 and connective circuitry or other data conduits that couple the data generating or data managing components of the device. A power storage cell in the form of a battery 174 that may be rechargeable may also be disposed within the housing 124. Data generating or managing components of the device may include the processor(s) 170, the memory device 172, sensors 158, including any pressure or temperature sensors, the GUI 166 and the like.

Figure 1D:
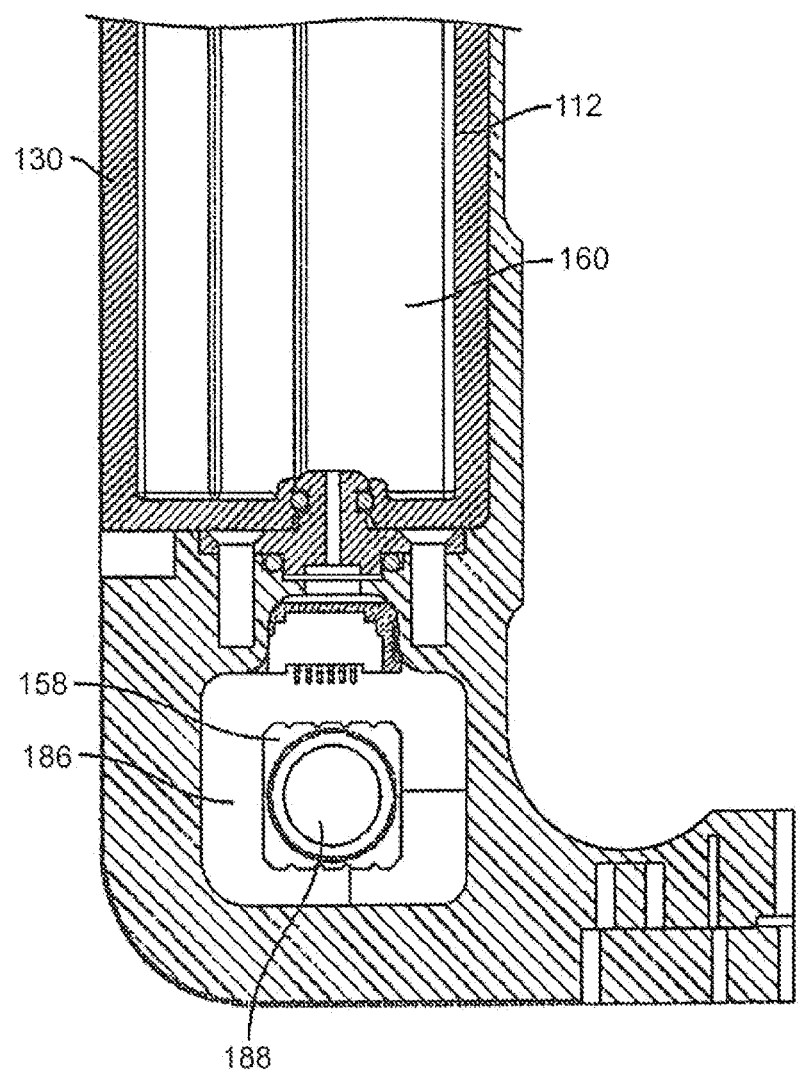
FIG. 1D is a partial sectional view of the infusion cartridge and pump device of FIGS. 1A and 1B.

The pressure inside the infusion cartridge 112, and particularly the interior volume 160 of the infusion cartridge 112, may be measured by a pressure sensor 158 disposed in the infusion cartridge 112 or in the pump device 114 in a volume, such as pocket 186 as shown in FIG. 1D. Pocket 186 is an interior volume disposed within the pump device 114 and in fluid communication with an interior volume of the fluid cartridge 112. The pocket 186 is in sealed relation with the interior volume 160 of the cartridge. As such, a pressure sensor 158 disposed within the volume of the pocket 186 will read the pressure of the volume 160 in the cartridge, but can remain with the pump device 114 after disposal of the disposable cartridge 112. This configuration lowers the cost of the cartridge while providing for pressure measurement within the cartridge 112. In some embodiments, data from the pressure sensor 158 may be used to provide a measurement of how much insulin or other medicament is being delivered by the first pump device 114. Alternatively, the pressure sensor 158 can be disposed within the cartridge directly in the sealed volume 160.

The pump device 114 can also include a thermistor or other temperature sensor 188 including an optical or infrared sensor that measures the temperature of the insulin or other medicament within the reservoir 126 upon coupling the infusion cartridge 112 with the pump device 114. Taking the temperature of the air may be important in measuring how much insulin or other medicament is in the fluid reservoir. In some embodiments, the thermistor or other temperature sensor 188 is positioned in the pocket 186 such that it can measure the temperature of the air in the pocket 186 as shown in FIG. 1D. As noted above, the pocket 186 may also include a pressure sensor 158 coupled to the controller 168 for measuring pressure within the pocket 186 and volume 160. Because the air in the pocket 186 is in fluid communication with the residual air within the chamber 160, the temperature and pressure of the air in the infusion cartridge 112 surrounding the fluid reservoir 126 may be equal or approximately equal to the temperature and pressure of the air in contact with the temperature sensor 188 and pressure sensor 158. In turn, the temperature sensor 188 may provide a relatively accurate measurement of the temperature of the insulin or other medicament within the reservoir 126.

Referring to FIGS. 2-7, an embodiment of the delivery mechanism 132 is depicted in a fluid delivery cycle sequence wherein fluid from the interior volume of the reservoir 126 is drawn into the bore 220 of the delivery mechanism 132 and dispensed from the dispense outlet port 142.

Referring again to FIG. 2, a portion of the fluid reservoir cartridge 112 including a delivery mechanism 132 is shown in section as well as a portion of a drive mechanism 150 of an infusion pump. The disposable fluid cartridge 112 includes the delivery mechanism 132 which has a delivery mechanism body 236 and a bore 220 disposed in the delivery mechanism body 236. The bore 220, which may have a substantially round transverse cross section, includes a distal end 238, a proximal end 240 disposed towards the drive mechanism 150 of the infusion pump 114, an interior volume 242, a reservoir inlet port 138, a fluid dispense port 142, a vent inlet port 146 and a vent outlet port 148. The spool 156, which may also have a substantially round transverse cross section, is slidingly disposed within the bore 220 and forms a collapsible first volume 244 and a vent second volume 246 between the bore 220 and an outside surface 266 of the spool 156.

The collapsible first volume 244 of the delivery mechanism 132 may be positionable to overlap the reservoir inlet port 138 independent of an overlap of the fluid dispense port 142. The collapsible first volume 244 may be formed between a first seal 248 around the spool 156, a second seal 250 around the spool, an outer surface of the spool body between the first and second seal 250 and an interior surface 252 of the bore 220 between the first and second seal 248 and 250. The first and second seals 248 and 250 are axially moveable relative to each other so as to increase a volume of the collapsible volume 244 when the first and second seals 248 and 250 are moved away from each other and decrease the collapsible volume 244 when the seals 248 and 250 are moved closer together.

The second seal 250 is disposed on a main section 254 of the spool 156 of the delivery mechanism 132 and moves in conjunction with movement of the rest of the spool. A proximal end 196 of the spool 156 is coupled to a ball portion 194 of a drive shaft 190 of the drive mechanism 150 of the pump device 114. The drive mechanism 150 includes a rack and pinion 192 mechanism actuated by an electric motor 152 through a gear box 154. As such, the second seal 250 moves or translates axially in step with axial translation of the spool 156 and drive shaft 190. The first seal 248, however, is disposed on a distal section 258 of the spool 156 which is axially displaceable with respect to the main section 254 of the spool 156. The distal section of the spool 156 is coupled to the main section of the spool by an axial extension 260 that is mechanically captured by a cavity 261 in the main section 254 of the spool 156. This configuration allows a predetermined amount of relative free axial movement between the distal section 258 of the spool and the nominal main section 254 of the spool 156.

For some embodiments, a volume of a "bucket" of fluid dispensed by a complete and full dispense cycle of the spool 156 may be approximately equal to the cross section area of the bore 220 multiplied by the length of displacement of the captured axial extension of the spool 156 for the distal section 258. The complete bucket of fluid may also be dispensed in smaller sub-volumes in increments as small as a resolution of the drive mechanism 150 allows. For some embodiments, a dispense volume or bucket defined by the complete collapsible volume 244 of the delivery mechanism 132 may be divided into about 10 to about 100 sub-volumes to be delivered or dispensed. In some cases, the maximum axial displacement between the distal section and main section of the spool may be about 0.01 inch to about 0.04 inch, more specifically, about 0.018 inch, to about 0.022 inch.

Figure 2:
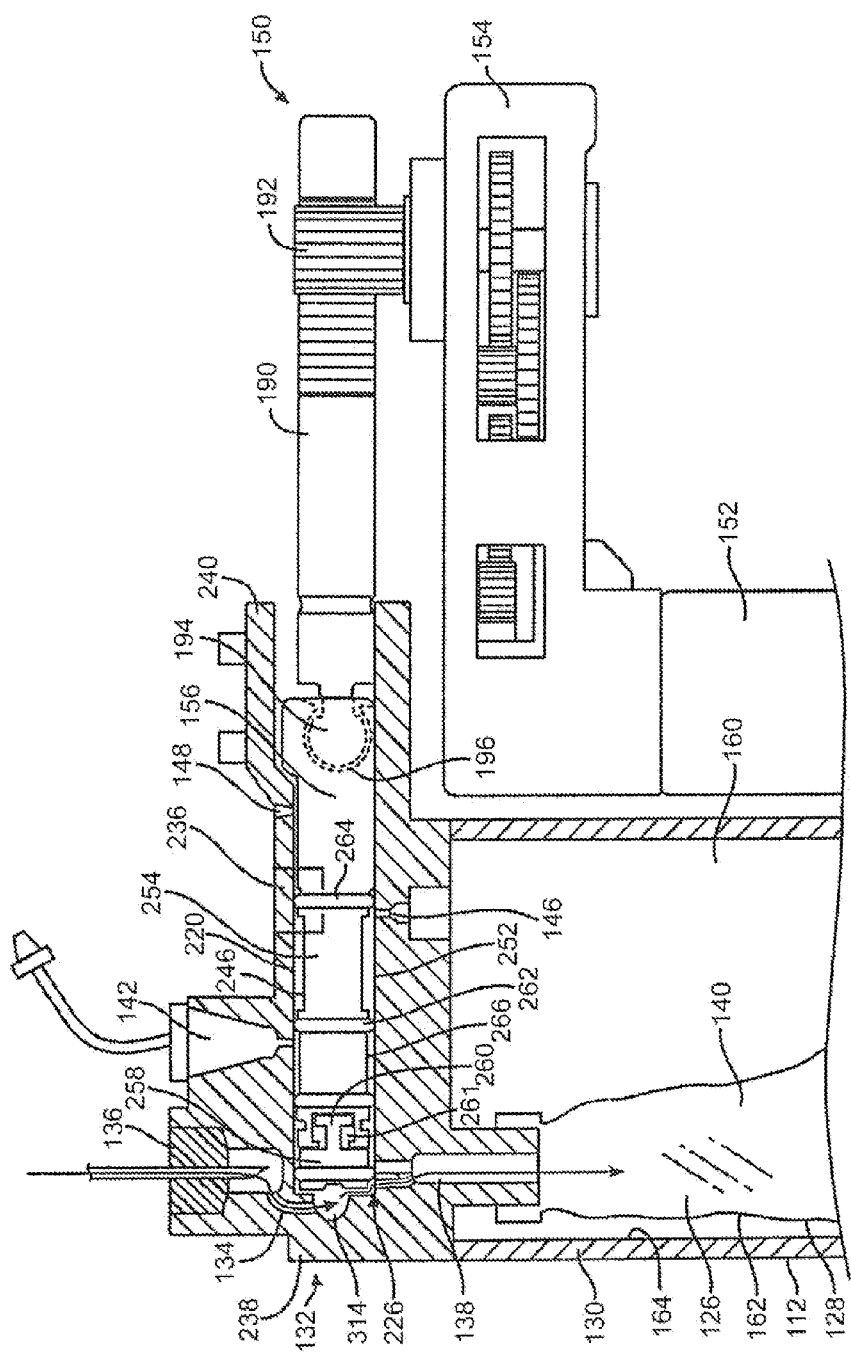
FIG. 2 is a partial sectional view of a delivery mechanism of an infusion pump with the spool of the delivery mechanism positioned at a distal hard stop for filling of the expandable reservoir according to an embodiment of the present invention.
Figure 3:
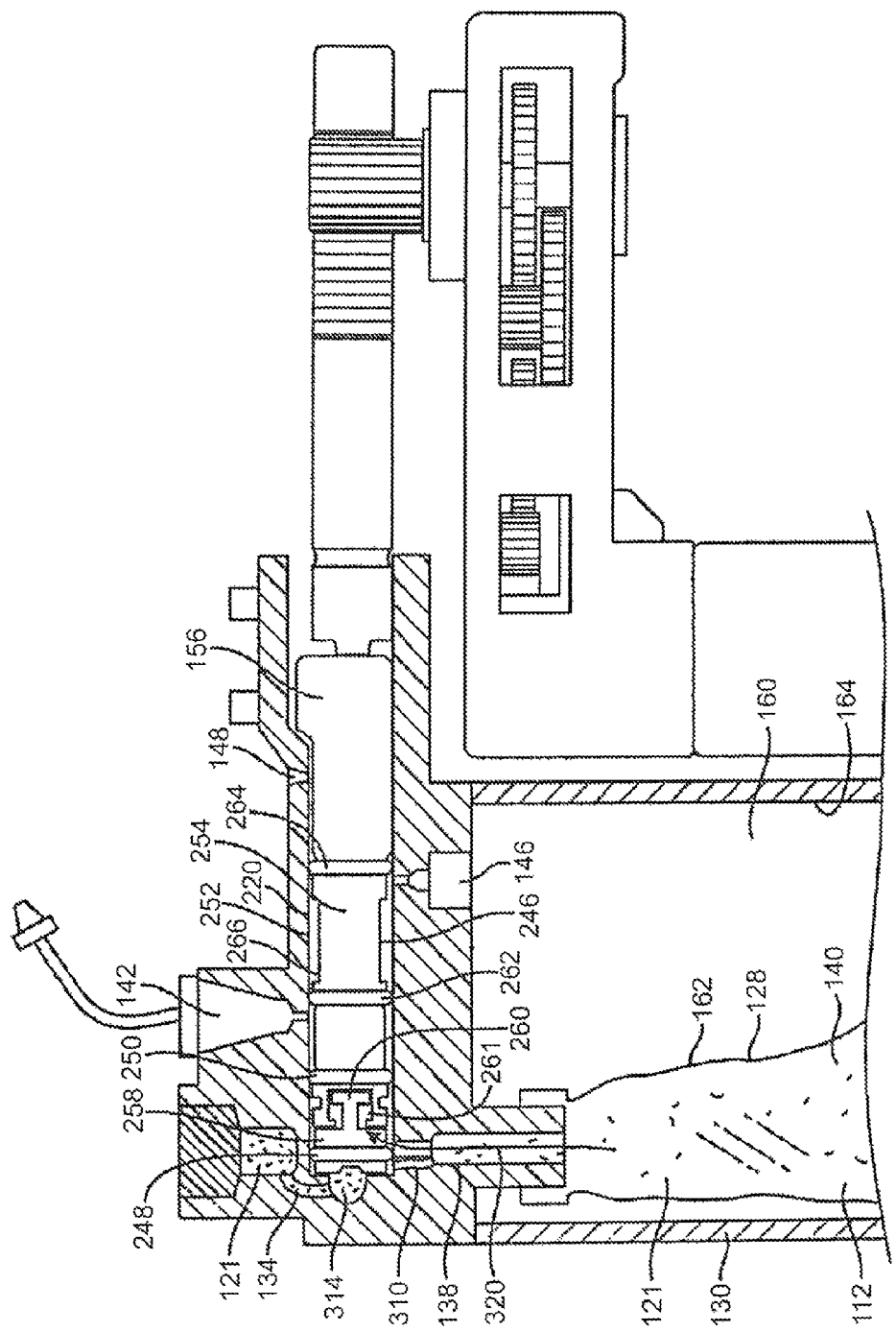
FIG. 3 is similar to FIG. 2, but with the spool of the delivery mechanism positioned for filling of a collapsible volume of the spool.

In use, once the reservoir cartridge 112 of the infusion pump system 110 has been installed or otherwise snapped into place in the slot 122 of the pump device 114, the interior volume 140 of the collapsible reservoir 126 may then be filled with a desired fluid 121 for dispensing. In order to fill the reservoir 126, the spool 156 may be translated by the drive mechanism 150 to a hard stop position 226 as shown in FIG. 2. In the hard stop position 226 the first seal 248 is disposed proximally of a relief port 310, the relief port 310 being disposed in fluid communication between a distal end 238 of the bore 220 and the reservoir volume 140. In the hard stop position, the first seal 248 is also disposed distally of the reservoir inlet port 138. In the hard stop position, a distal end 316 of the spool 156 is contacting the distal end 238 of the bore 220 or a shoulder portion 312 of the distal end 238 of the bore 220 to prevent any further distal displacement of the spool 156.

A reservoir fill port 134 is disposed on a top portion of the bore 220 substantially opposite the bore 220 of the reservoir inlet port 138. With the spool 156 and seals 248, 250, 262 and 264 thereof so positioned, a patient may then obtain an amount of a desired fluid to be dispensed. In some cases, if the desired fluid to be dispensed is insulin or other suitable medicament, the patient 127 typically stores the insulin in a refrigerated glass container. The insulin is then accessed with a hypodermic needle 222 of a syringe device and drawn into an interior volume of the syringe (not shown). The tip of the hypodermic needle 222 of the syringe may then be pushed through a septum membrane 136 that seals the reservoir fill port 134 as shown and fluid manually dispensed from the interior volume of the syringe, through the hypodermic needle 222, through a bubble trap volume 314 in the bore 220 of the delivery mechanism 132 and into the interior volume 140 of the collapsible reservoir 126 of the cartridge 112 as shown by the arrow 318 in FIG. 2.

As discussed above with regard to other embodiments of the delivery mechanism 132, the volume 160 of the cartridge 112 disposed between an outside surface 162 of the flexible membrane 128 of the collapsible reservoir 126 and an inside surface 164 of the rigid shell 130 may include or be in operative communication with a pressure sensor 158. The pressure sensor 158 may be used to monitor the pressure within the volume 160 during the filling of the collapsible reservoir 126. The controller 168 of the pump system 114 may be programmed with information regarding the fixed volume of the rigid shell 130 of the cartridge 112 and configured to calculate the volume of fluid loaded into the collapsible reservoir 126 based on the pressure rise within the rigid shell 130 upon filling of the collapsible reservoir 126. The data regarding the volume of fluid loaded into the collapsible reservoir 126 may be stored and used to calculate and display data later in the use cycle such as fluid remaining in the collapsible reservoir 126 and the like.

Once the collapsible reservoir 126 contains a desired amount of a fluid 121 to be dispensed, a dispense cycle may be initiated by driving the spool 156 with the drive mechanism 150 based on commands from a controller 168 of the pump device to a position with the collapsible first volume 244 in communication with the reservoir inlet port 138. The hard stop position depicted in FIG. 2 is such a position. If the spool 156 has been driven to this hard stop position 226 in a distal direction from previous proximal position, the friction generated between the first seal 248 of the spool 156 and the inside surface 252 of the bore 220 will have collapsed the collapsible volume 244 of the delivery mechanism 132 with the first seal 248 and second seal 250 in a least axially separated state. In this state, the collapsible volume 244 has a minimum volume. Such a state of the delivery mechanism 132 is shown in FIG. 2. Once in this pre-fill position, the spool 156 may then be driven so as to axially separate the first and second seals 248 and 250 (and the main section 254 of the spool 156 and distal section 258 of the spool 156) of the collapsible first volume 244 and draw fluid into the first volume 244 through the reservoir inlet port 138 from the reservoir 126 as shown by the arrow 320 in FIG. 3. As the fluid 121 is drawn into the collapsible volume 244, the pressure within the volume 160 decreases. As previously discussed, this drop in pressure may be used in accordance with the ideal gas law to determine the amount of material taken from the collapsible reservoir 126. An unexpected reading based on the magnitude of the translation of the main section 254 of the spool 156 may also be used to detect a failure of a portion of the delivery mechanism 132 in some cases.

Figure 4:
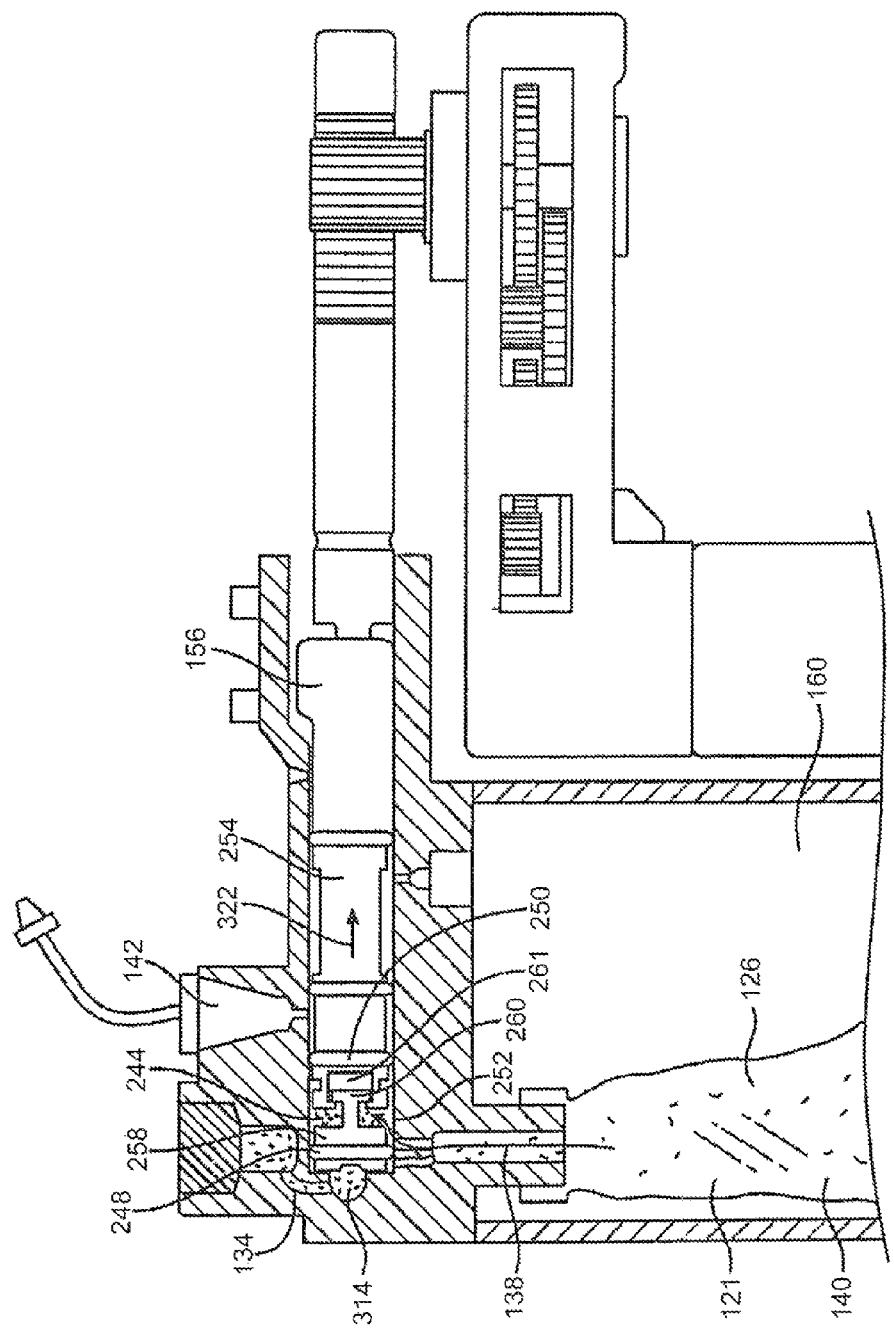
FIG. 4 is similar to FIG. 2, but with the spool of the delivery mechanism positioned after filling of the collapsible volume of the spool.
Figure 5:
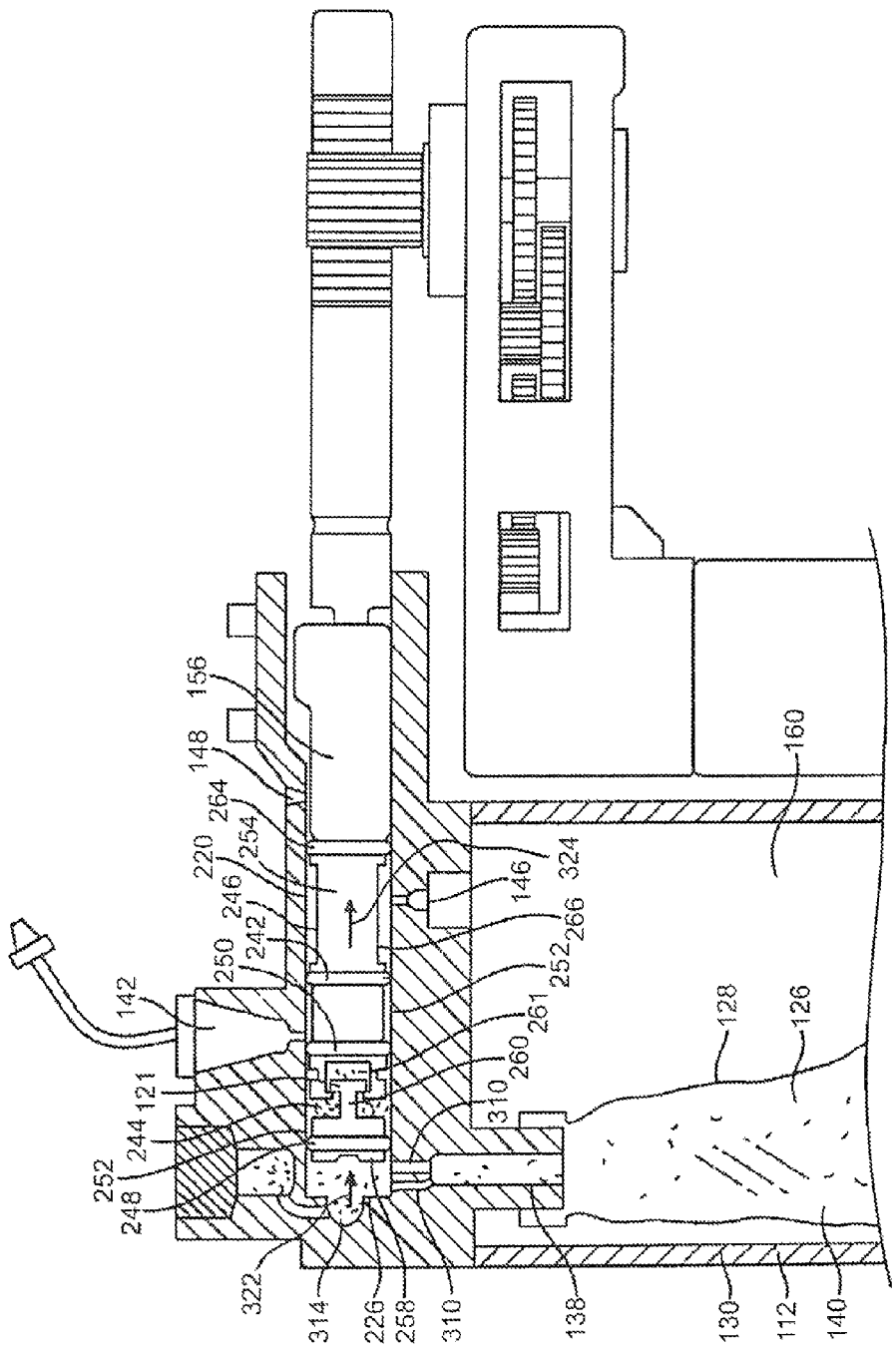
FIG. 5 is similar to FIG. 2, but with the collapsible volume of the device full of fluid being displaced proximally towards the dispense port of the device.

The collapsible volume 244 of the delivery mechanism 132 may be completely filled by proximally retracting the main section 254 and second seal 250 of the spool 156 relative to the first seal 248 and distal section 258 of the spool 156 as shown by arrow 322 on spool 156 in FIG. 4. Once filled, the spool 156 may then be driven in a proximal direction as shown in FIG. 5 wherein there are two seals 248 and 250 disposed in the bore 220 between the reservoir inlet port 138 and relief port 310 and the dispense port 142. As shown by arrow 323 and arrow 324 in FIG. 5, both the main section 254 and distal section 258 of the spool 156 are proximally retracted together. The captured axial extension of the distal section 258 by the main section 254 pulls the distal section along without axial displacement between the main section 254 and distal section 258 of the spool 156. The dispense port may be in fluid communication with a subcutaneous portion of a patient's body. The delivery mechanism 132 always includes at least one seal 248 or 250 disposed in the bore 220 between the reservoir volume 140 and material 121 disposed therein and the dispense port 142 in order to prevent a free flow condition wherein the material 121 in the reservoir 126 is in uninterrupted communication with the patient's body.

Figure 6:
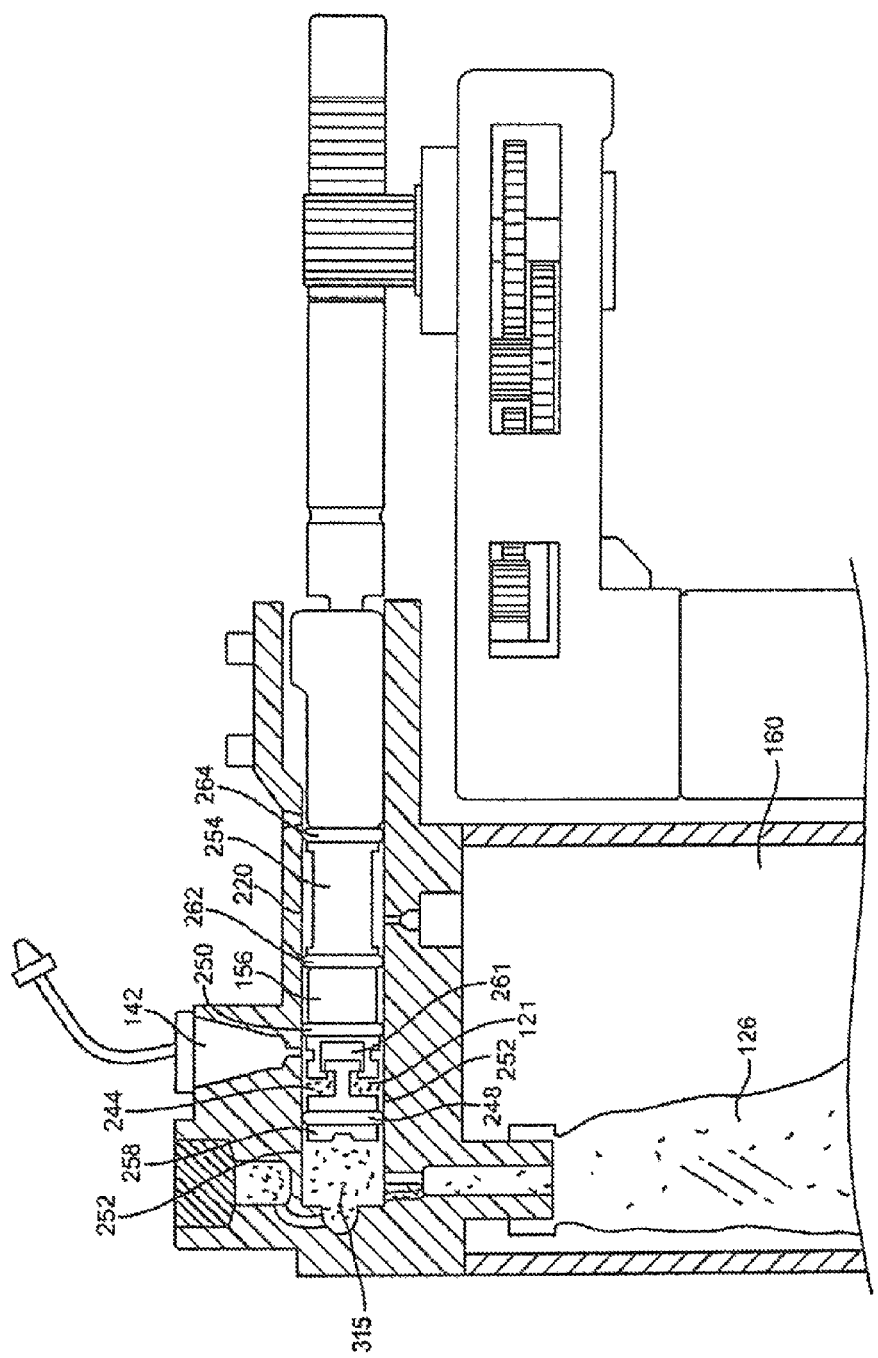
FIG. 6 is similar to FIG. 2, but with the spool of the delivery mechanism positioned prior to delivery of fluid into the dispense port from the collapsible volume of the spool.
Figure 7:
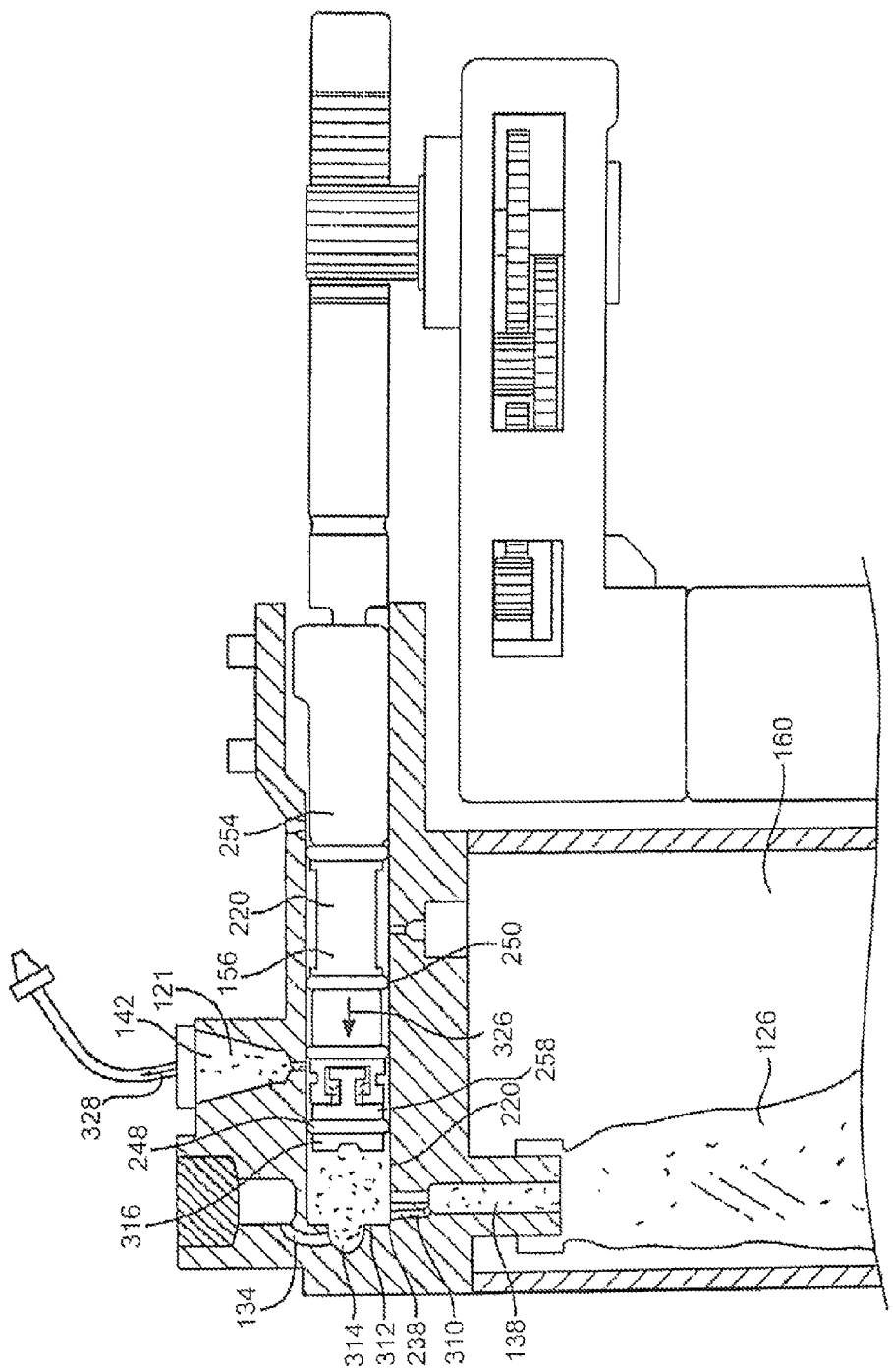
FIG. 7 is similar to FIG. 2, but with the spool of the delivery mechanism positioned after delivery of fluid from the collapsible volume of the spool into the dispense port.

Once filled, the spool 156 and filled collapsible volume 244 may be proximally displaced with the drive mechanism 150 to a position with the collapsible first volume 244 in communication with the fluid dispense port 142 of the bore 220 as shown in FIG. 6. Once the spool 156 is positioned as depicted in FIG. 6, the main section of the spool 156 may then be axially driven in a distal direction by the drive mechanism 150 with the distal section 258 of the spool remaining stationary or substantially stationary. This axial distal movement of the main section 254 as indicated by arrow 326 on the spool 156 depicted in FIG. 7, serves to at least partially collapse the collapsible first volume 244. Collapsing the first volume 244 of the delivery mechanism 132 dispenses fluid from the collapsible first volume 244 through the fluid dispense port 142 as shown by the arrow 328 in FIG. 7. Once all fluid from the collapsible first volume 244 is dispensed in this manner, additional cycles as described above can be completed to provide additional insulin to the patient. Further details on the operation and configuration of such an infusion pump can be found in U.S. Patent Application Publication No. 2011/0144586, which is hereby incorporated by reference herein.

Figure 8:
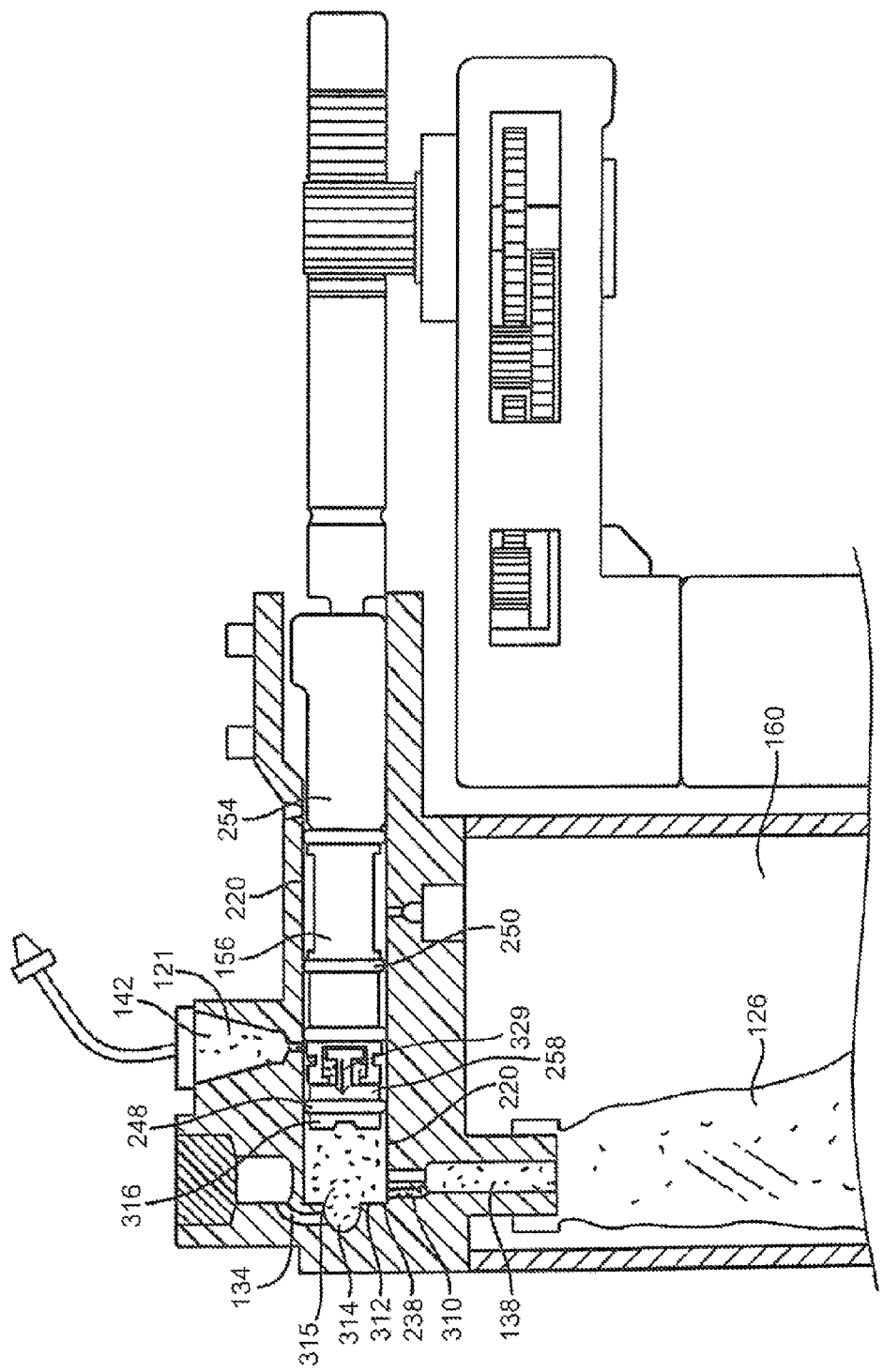
FIG. 8 is similar to FIG. 2, but depicting a condition of an occlusion present in the delivery line.

The above description relates to the use of a portable or ambulatory pump device 114 and cartridge 112 when properly operating to draw fluid from the reservoir 126 and dispense it to a patient. As described above with reference to FIG. 7, when the main section 254 of the spool 156 is moved distally to collapse the first volume 244 to dispense the fluid, the distal section 256 of the spool 156 is stationary. However, there are certain conditions that will prevent the device 114 from operating properly. For example, an occlusion in the line delivering the fluid from the device to the patient will prevent the fluid from traveling along path 328 to the patient depicted in FIG. 7. Thus, as the main section 254 of the spool 156 is advanced distally, rather than propelling the fluid out the fluid dispense port 142, pressure builds up in the patient line and ultimately the pressure is exerted on the distal section 258 of the spool. When this pressure exceeds the frictional force of the seal 248, the distal section 258 of the spool 156 is also moved distally as shown by arrow 329 in FIG. 8.

This movement of the distal section 258 of the spool 156 can used to determine whether or not an occlusion is present in the patient line because the movement will cause the pressure in the reservoir to react differently indicating that an occlusion is present. Pressure readings taken during certain predetermined times of either basal insulin delivery or bolus delivery can be used by the processor 170 to identify an occlusion based on movement of the distal section 258.

During basal insulin delivery, typically the "bucket" of insulin is filled as shown in FIGS. 2-5 and then the insulin in the bucket is slowly delivered to the patient a portion at a time. For example, the motor may be activated to move the main portion 254 of the spool 156 to deliver a portion of the insulin every five minutes over the course of one or several hours. Thus, the bucket may only be filled once every few hours. As described above, if there is an occlusion in the line, the force of the motor 152 advancing the spool 156 will, instead of dispensing fluid, cause the distal section 258 of the spool 156 to move distally in the bore 220 as shown by the arrow 329 in FIG. 8. This movement will force some of the fluid in the space 315 back into the reservoir 126. This change in volume of the reservoir 126 will correspondingly alter the pressure in the interior volume 160 of the cartridge 112.

Thus, pressure measurements of the interior volume 160 made by the pressure sensor 158 can be utilized by the processor 170 to determine if there is an occlusion in the patient line as reflected by a change in pressure. In one embodiment, the pressure is monitored immediately before and immediately after the motor 152 is activated to move the spool 156 to dispense a portion of insulin for the basal insulin delivery. If the pressure readings are the same, then the insulin was delivered through the patient line and there is no occlusion. If there is an occlusion that prevented insulin from being delivered to the patient and caused the distal section 258 to move during the operation, then the pressure readings will change. These changed readings, or accumulation of readings, indicate that an occlusion is present due to movement of the distal section causing additional insulin to be forced back into the reservoir 126.

If the pressure readings indicate that an occlusion is present, the processor 170 can cause an alarm indicating the presence of an occlusion to be generated and displayed to the user on the GUI 166. The pump may also automatically cease operation upon generation of such an alarm until the user indicates that the occlusion has been corrected. Because the pressure readings taken before and after the motor move to deliver a portion of the bucket are taken with only a short period of time elapsing—as opposed to being taken each time the bucket is filled or completely emptied—any effects from long term systematic sensor changes are minimized. In one embodiment, an occlusion alarm can be generated when the before and after pressure readings are different for a single motor move. In other embodiments, the processor 170 may require that the pressure readings be different for two or more consecutive motor moves before indicating an occlusion in order to reduce signal noise. In addition, if a sensor has been inactive for a period of time, it may take some time for the measurements of the sensor to reach a desired degree of accuracy, so it may be desirable to begin comparing pressure values only after the sensor has been operating for a certain period of time. Same or constant pressure in this context may mean exactly the same pressure. Same or constant pressure can also mean pressures within a defined threshold of each other.

Figure 9:
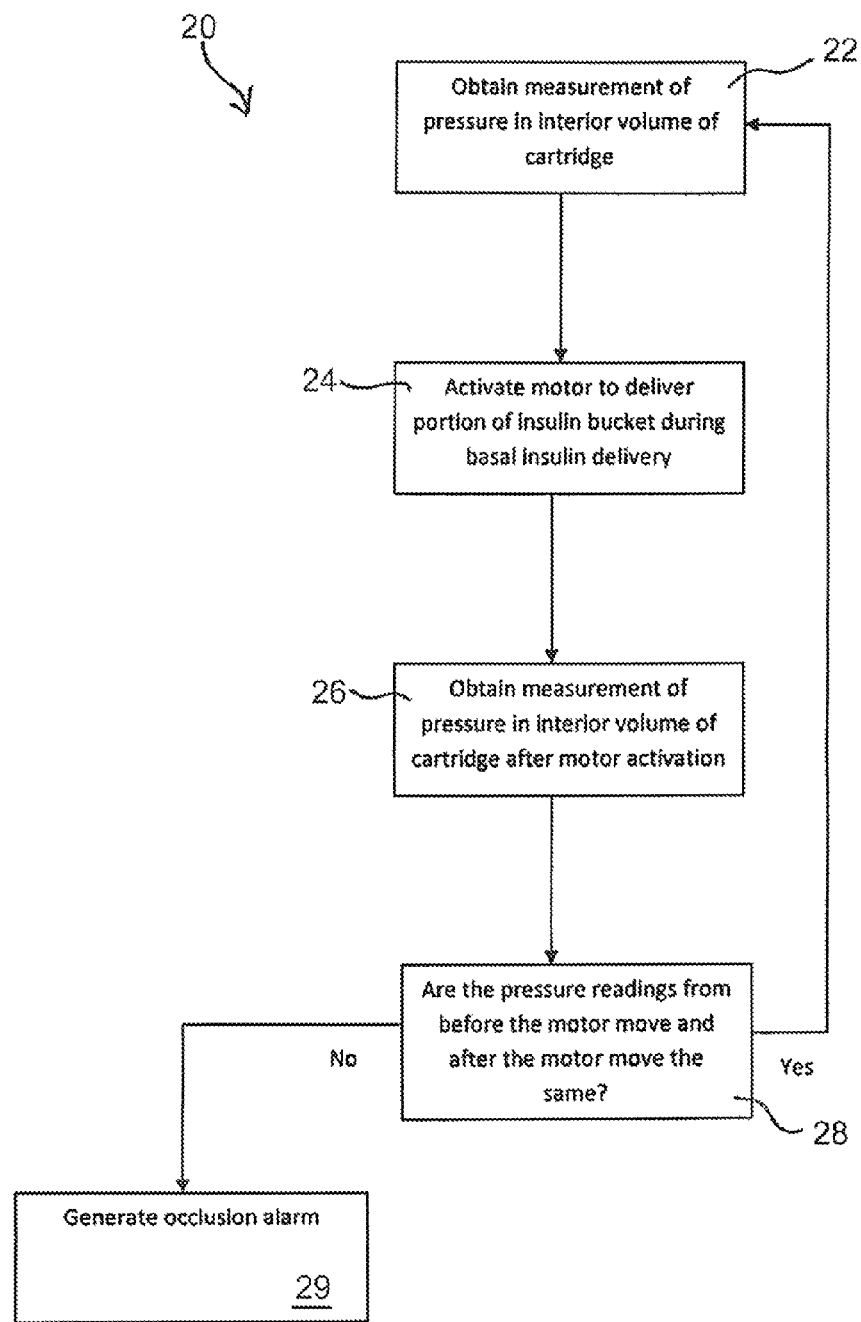
FIG. 9 is a flowchart of a method for detecting occlusions in a portable infusion device during basal insulin delivery according to an embodiment of the present invention.

FIG. 9 depicts a flowchart of a method of detecting occlusions in a portable infusion pump during basal insulin delivery 20 according to an embodiment of the present invention. At step 22, a measurement of pressure in the interior volume of an insulin cartridge is made prior to activating a motor to deliver a portion of a bucket of insulin to a patient. The motor is then activated at step 24 to deliver the portion of insulin to the patient. At step 26, a measurement of the pressure in the interior volume of the cartridge is obtained after the motor move. Preferably, this measurement is taken immediately following the motor being powered down. The pressure readings before and after the motor move are compared by the processor at step 28. If the pressure readings are the same, this is indicative of there being no occlusion in the patient delivery line and the method reverts back to step 22 for a subsequent motor move. If the pressure readings are not the same, the comparison indicates that there is an occlusion in the patient line. An occlusion alarm can then be generated at step 29. The occlusion alarm can be an audio alarm, visual alarm, tactile alarm, or some combination of these. In some embodiments, the process will not proceed to step 29 to generate the alarm unless the pressure readings are different for more than one consecutive motor move. As noted above, the pressure readings being the "same" can mean that the pressure readings are exactly the same when rounded to a desired degree of precision or that the values are within a predefined threshold amount or percentage of each other.

In some embodiments, the pressure readings accumulated during motor moves are compared to a baseline value. For example, the difference between each pressure reading and the baseline is calculated. The differences can be summed and/or averaged, and if the difference is greater than a threshold amount from the baseline, an occlusion is detected. The baseline and/or threshold values can be varied based on the relative volume of air in the cartridge. When there is a greater amount of air in the cartridge, the pressure reading is smaller. Thus, a lower threshold deviation from the baseline can trigger an occlusion detection. In this manner, the threshold and baseline values can be determined based on the ideal gas law. In other embodiments, rather than comparing pressure readings to a baseline, the pressure readings are compared directly to each other and a threshold difference between readings, or an accumulation of readings, that indicates an occlusion can be calculated as described above.

In bolus delivery, the volume of fluid in the reservoir decreases by a fixed amount with each subsequent cycle of the delivery mechanism to draw fluid from the reservoir 126 into the bore 220 and then deliver it to the patient. Correspondingly, the pressure in the interior volume 160 of the cartridge 112, as measured by the pressure sensor 158, drops by a fixed amount with each subsequent cycle as shown by line 12 in FIG. 10. In contrast, when an occlusion is present in the patient line, fluid is not being dispensed out of the device and therefore each subsequent operation of the motor does not draw additional fluid from the reservoir. Therefore, the pressure in the interior volume 160 of the cartridge after each subsequent operation remains constant as shown by the line 14 in FIG. 10. Line 14 reflects that the pressure will drop when the frictional force holding the distal section 258 of the spool 156 in place is overcome moving the distal section 258 distally, but will build back up again each time the main section 254 of the spool 156 is advanced for the operation intended to dispense fluid out of the dispense port 142.

Figure 10:
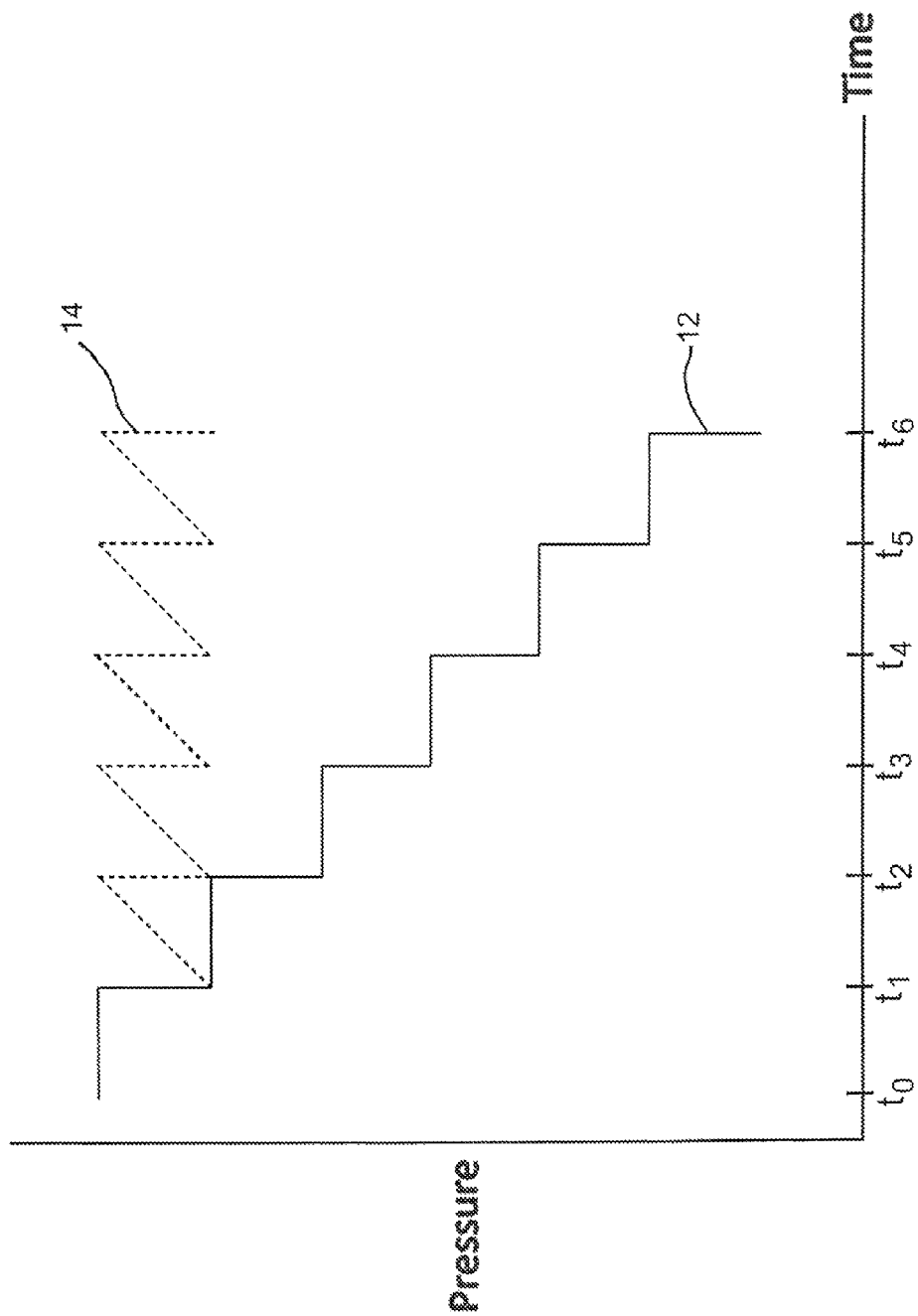
FIG. 10 is a graph of cartridge pressure versus time for an infusion device such as the infusion device of FIG. 2 according to an embodiment of the invention.

In FIG. 10, the time markings $t_0$ through $t_6$ indicate times at which pressure readings are taken that are each taken at an identical stage in the bolus delivery process. In one embodiment, the pressure readings are taken after the bolus has been delivered and the device is in the "ready to fill" position such as in FIG. 2 and/or FIG. 3. In other embodiments, pressure readings can be taken at different times during the operational sequence of the pump. Preferably, however, the readings are all taken at the same time during each subsequent cycle to allow for more accurate comparison of readings.

Thus, by monitoring pressure in the interior volume 160 of the cartridge 112 during subsequent bolus cycles, it can be determined by the processor 170 whether an occlusion is present in the line delivering fluid to the patient. If each subsequent pressure reading is dropping by a constant amount, there is no occlusion and the system is operating normally. If the pressure readings remain constant at each of two or more subsequent time intervals, then an occlusion is present. Long term systematic effects on the sensors are minimized because all of the insulin in the bucket is delivered immediately, so there is not a significant time gap between readings. This is particularly true when the measurements are taken at the "ready to fill" position of the delivery mechanism, because the mechanism will again be in the ready to fill position upon completing the bolus.

If the pressure readings indicate that an occlusion is present, an alarm indicating the presence of an occlusion can be generated and displayed to the user on the GUI 166 by the processor 170. The pump may also automatically cease operation upon generation of such an alarm until the user indicates that the occlusion has been corrected. In one embodiment, an occlusion alarm can be generated when two consecutive pressure readings are constant. In other embodiments, the pump may require more than two pressure readings before indicating an occlusion in order to reduce signal noise. Constant pressure in this context may mean exactly the same pressure. Constant pressure can also mean pressures within a defined threshold of each other.

Figure 11:
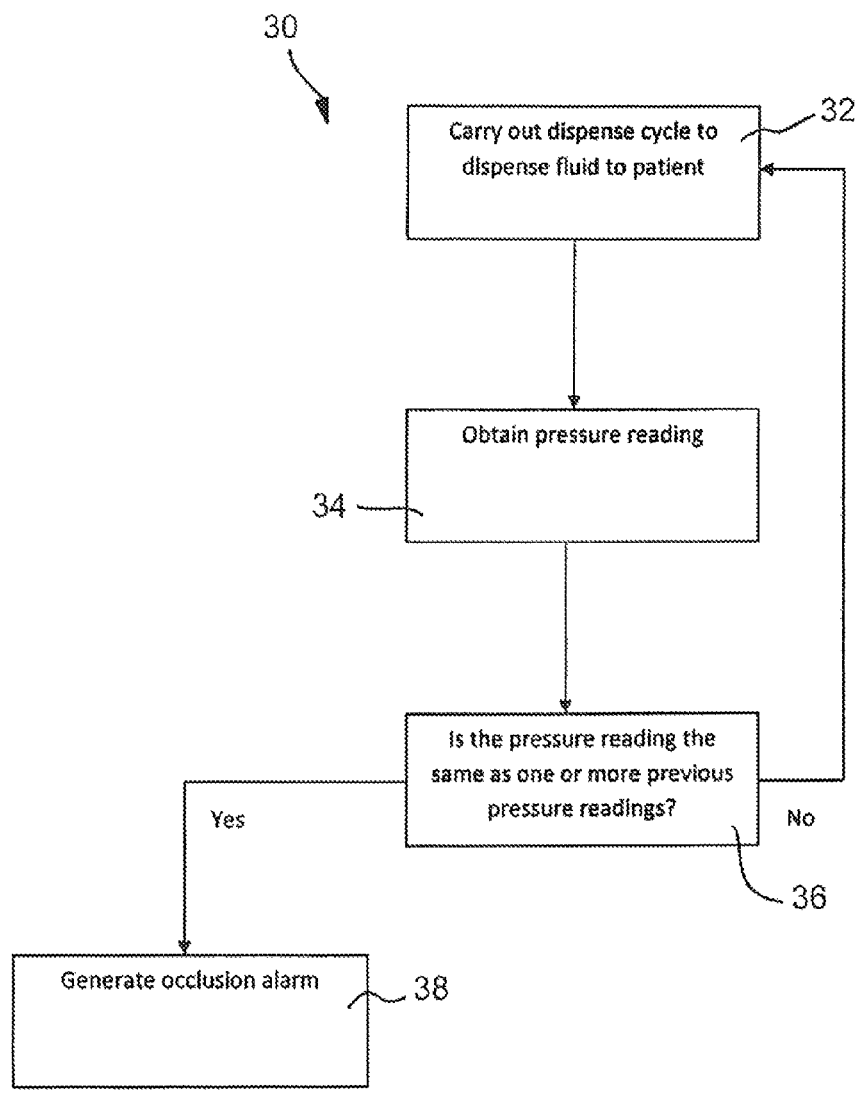
FIG. 11 is a flowchart of a method for detecting occlusions in a portable infusion device during bolus insulin delivery according to an embodiment of the present invention.

FIG. 11 depicts a flowchart of a method of detecting an occlusion in an infusion pump system 30 according to an embodiment of the present invention. At step 32, a dispense cycle for delivering a bolus of fluid to a patient, such as described herein, is carried out. A pressure reading is obtained at some point before, during or after the dispense cycle at step 34. In one embodiment, the pressure reading is immediately following dispensing the fluid to the patient so that the delivery mechanism is once again in the "ready to fill" position. The pressure can be the pressure in a housing of a cartridge of the portable infusion system containing the fluid reservoir, At step 36, the pressure reading is compared to one or more previous pressure readings by the processor 170. Typically, each compared pressure reading will be taken at the same stage of the dispense cycle as previous readings. For example, the previous pressure reading may have been taken immediately prior to filling the bucket of insulin. If the pressure readings are not the same, an occlusion alarm can be generated at step 38. Occlusion alarm can be an audio alarm, visual alarm, tactile alarm, or some combination of these. In some embodiments, the process will not proceed to step 38 to generate the alarm unless the current pressure reading is the same as more than one previous pressure reading. As noted above, the pressure readings being the "same" can mean that the pressure readings are exactly the same when rounded to a desired degree of precision or that the values are within a predefined threshold amount or percentage of each other.

In some embodiments, an occlusion detection system and method as described herein can account for physical conditions of the pump that falsely indicated an occlusion. Thus, if a single reading or limited number of readings indicates that an occlusion is present, the system can determine whether or not the reading is a false reading based on a condition of the device. Examples of such conditions include the cartridge reservoir being empty, the cartridge being dislodged or otherwise removed between readings or rapid changes in ambient temperature or pressure.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. A method of detecting occlusions in an infusion pump comprising a disposable infusion cartridge and a pump device, the infusion cartridge including a collapsible reservoir for containing a fluid and a substantially rigid shell disposed over the collapsible reservoir and forming an interior volume between an outside surface of the collapsible reservoir and an inside surface of the shell, the infusion cartridge further including a delivery mechanism having a spool slidingly disposed in a bore, the spool including a main section and a distal section axially displaceable relative to the main section with a collapsible volume formed between a seal on the main section and a seal on the distal section, the pump device configured to selectively receive the infusion cartridge and cooperate with the infusion cartridge to deliver fluid from the reservoir into the collapsible volume and to a patient, the pump device including a drive mechanism powered by a motor and selectively engageable with the spool to impart controlled axial movements to the spool to deliver fluid to the patient, wherein the method comprises:
   actuating an operation to deliver fluid stored in the collapsible volume to a patient;
   determining whether the distal section of the spool moved axially at a time during the operation configured to deliver fluid from the collapsible volume to the patient when the distal section should have remained stationary; and
   selectively generating an occlusion alarm if it is determined that the distal section of the spool moved at the time it should have remained stationary.

2. The method of claim 1, wherein the infusion pump further comprises a pressure sensor in communication with the interior volume of the infusion cartridge located in one of the infusion cartridge and the pump device, wherein the method further comprises:
   obtaining a first pressure reading of the pressure in the interior volume of the infusion cartridge from the pressure sensor;
   obtaining a second pressure reading of the pressure in the interior volume of the infusion cartridge from the pressure sensor following the operation configured to deliver fluid from the collapsible volume to the patient;

comparing the first pressure reading to the second pressure reading; and determining whether the distal section of the spool moved axially at a time during the operation configured to deliver fluid from the collapsible volume to the patient when the distal section should have remained stationary based on the comparison.

3. The method of claim 2, wherein the operation delivers a portion of the fluid in the collapsible volume and determining whether the distal section of the spool moved axially at a time during the operation configured to deliver fluid from the collapsible volume to the patient when the distal section should have remained stationary includes determining that the distal section of the spool moved if the second pressure reading is not the same as the first pressure reading.

4. The method of claim 2, wherein the operation delivers all of the fluid in the collapsible volume and determining whether the distal section of the spool moved axially at a time during the operation configured to deliver fluid from the collapsible volume to the patient when the distal section should have remained stationary includes determining that the distal section of the spool moved if the second pressure reading is the same as the first pressure reading.

5. The method of claim 2, wherein the pressure sensor is disposed in the pump device.

6. The method of claim 1, wherein selectively generating the occlusion alarm includes ceasing all delivery of fluid from the reservoir.

7. A method of detecting occlusions in an infusion pump comprising a disposable infusion cartridge and a pump device, the infusion cartridge including a collapsible reservoir for containing a fluid and a substantially rigid shell disposed over the collapsible reservoir and forming an interior volume between an outside surface of the collapsible reservoir and an inside surface of the shell, the infusion cartridge further including a delivery mechanism having a spool slidingly disposed in a bore, the spool including a main section and a distal section axially displaceable relative to the main section with a collapsible volume formed between a seal on the main section and a seal on the distal section, the pump device configured to selectively receive the infusion cartridge and cooperate with the infusion cartridge to deliver fluid from the reservoir into the collapsible volume and to a patient, the pump device including a drive mechanism powered by a motor and selectively engageable with the spool to impart controlled axial movements to the spool to deliver fluid to the patient, the infusion pump further comprising a pressure sensor in communication with the interior volume of the infusion cartridge and located in one of the infusion cartridge and the pump device, wherein the method comprises:

actuating the motor to deliver a portion of fluid contained in the collapsible volume;

obtaining a first pressure reading of the pressure in the interior volume of the infusion cartridge from the pressure sensor prior to actuating the motor;

obtaining a second pressure reading of the pressure in the interior volume of the infusion cartridge from the pressure sensor after the motor is powered down following actuation;

comparing the first pressure reading to the second pressure reading; and selectively generating an occlusion alarm based on the comparison of the first pressure reading to the second pressure reading if the second pressure reading is not the same as the first pressure reading.

8. The method of claim 7, wherein the first pressure reading is obtained immediately prior to actuating the motor and the second pressure reading is obtained immediately after the motor is powered down following actuation.

9. The method of claim 7, wherein selectively generating an occlusion alarm includes only generating the occlusion alarm if the second pressure reading is not the same as the first pressure reading and at least one previously obtained pressure reading.

10. The method of claim 7, wherein the second pressure reading is not the same as the first pressure reading if it is not within a predetermined threshold of the first pressure reading.

11. The method of claim 7, wherein the pressure sensor is disposed in the pump device.

12. The method of claim 7, wherein selectively generating an occlusion alarm includes ceasing all delivery of fluid from the reservoir.

13. A method of detecting occlusions in an infusion pump comprising a disposable infusion cartridge and a pump device, the infusion cartridge including a collapsible reservoir for containing a fluid and a substantially rigid shell disposed over the collapsible reservoir and forming an interior volume between an outside surface of the collapsible reservoir and an inside surface of the shell, the infusion cartridge further including a delivery mechanism having a spool slidingly disposed in a bore, the spool including a main section and a distal section axially displaceable relative to the main section with a collapsible volume formed between a seal on the main section and a seal on the distal section, the pump device configured to selectively receive the infusion cartridge and cooperate with the infusion cartridge to deliver fluid from the reservoir into the collapsible volume and to a patient, the pump device including a drive mechanism powered by a motor and selectively engageable with the spool to impart controlled axial movements to the spool to deliver fluid to the patient, the infusion pump further comprising a pressure sensor in communication with the interior volume of the infusion cartridge and located in one of the infusion cartridge and the pump device, wherein the method comprises:

actuating the motor to deliver all fluid contained in the collapsible volume to a patient;

obtaining a first pressure reading of the pressure in the interior volume of the infusion cartridge form the pressure sensor at a time prior to all of the fluid being delivered;

obtaining a second pressure sensor reading of the pressure in the interior volume of the infusion cartridge from the pressure sensor at a time after all of the fluid had been delivered;

comparing the first pressure reading to the second pressure reading; and selectively generating an occlusion alarm based on the comparison of the first pressure reading to the second pressure reading if the second pressure reading is the same as the first pressure reading.

14. The method of claim 13, wherein the first pressure reading is obtained prior to delivering any of the fluid and the second pressure reading is obtained prior to a subsequent actuation of the motor to deliver a subsequent amount of fluid that has been drawn from the collapsible reservoir into the collapsible volume.

15. The method of claim 13, wherein the first pressure reading is obtained during a first fluid delivery cycle and the second pressure reading is made during a subsequent fluid delivery cycle, and each reading is taken at a common point in the respective delivery cycle.

16. The method of claim 13, wherein selectively generating an occlusion alarm includes only generating the occlusion alarm if the second pressure reading is the same as the first pressure reading and at least one previously obtained pressure reading.

17. The method of claim 13, wherein the second pressure reading is the same as the first pressure reading if it is within a predetermined threshold of the first pressure reading.

18. The method of claim 13, wherein the pressure sensor is disposed in the pump device.

19. The method of claim 13, wherein selectively generating an occlusion alarm includes ceasing all delivery of fluid from the reservoir.

* * * * *